(12) United States Patent
Park et al.

(10) Patent No.: US 10,919,966 B2
(45) Date of Patent: Feb. 16, 2021

(54) ANTIBODY TO PROGRAMMED DEATH-LIGAND 1 (PD-L1) AND USE THEREOF

(71) Applicant: Y-BIOLOGICS INC., Daejeon (KR)

(72) Inventors: Jae Eun Park, Daejeon (KR); Soo A Choi, Jeollabuk-do (KR); Jisu Lee, Sejong (KR); Hyun Mi Lee, Daejeon (KR); Si Hyung Lee, Daejeon (KR); Gi Sun Baek, Daejeon (KR); Yeung Chul Kim, Daejeon (KR); Bum-chan Park, Daejeon (KR); Jung Chae Lim, Daejeon (KR); Young-Gyu Cho, Daejeon (KR); Young Woo Park, Daejeon (KR)

(73) Assignee: Y-BIOLOGICS INC., Daejeon (KR)

( * ) Notice: Subject to any disclaimer, the term of this patent is extended or adjusted under 35 U.S.C. 154(b) by 186 days.

(21) Appl. No.: 16/321,412

(22) PCT Filed: Aug. 7, 2017

(86) PCT No.: PCT/KR2017/008495
§ 371 (c)(1),
(2) Date: Jan. 28, 2019

(87) PCT Pub. No.: WO2018/026249
PCT Pub. Date: Feb. 8, 2018

(65) Prior Publication Data
US 2019/0322750 A1    Oct. 24, 2019

(30) Foreign Application Priority Data

Aug. 5, 2016 (KR) .................. 10-2016-0100211
Aug. 7, 2017 (KR) .................. 10-2017-0099673

(51) Int. Cl.
*A61K 39/00*    (2006.01)
*C07K 16/28*    (2006.01)

(52) U.S. Cl.
CPC .... *C07K 16/2827* (2013.01); *C07K 2317/565* (2013.01); *C07K 2317/567* (2013.01); *C07K 2319/33* (2013.01)

(58) Field of Classification Search
CPC .......... C07K 16/2827; C07K 2317/565; C07K 2317/567; C07K 2319/33; C07K 2317/76; A61P 35/00; A61K 2039/505
See application file for complete search history.

(56) References Cited

U.S. PATENT DOCUMENTS

2009/0055944 A1    2/2009    Korman et al.
2011/0209230 A1    8/2011    Korman et al.

FOREIGN PATENT DOCUMENTS

| CA | 2920173 A1 | 2/2015 |
|---|---|---|
| JP | 2008544755 | 12/2008 |
| WO | 8801649 A1 | 3/1988 |
| WO | 8806630 A1 | 9/1988 |
| WO | 8807085 A1 | 9/1988 |
| WO | 8807086 A1 | 9/1988 |
| WO | 8809344 A1 | 12/1988 |
| WO | WO2010077634 A1 | 7/2010 |
| WO | WO2015061668 A1 | 4/2015 |
| WO | 2015097536 A2 | 7/2015 |
| WO | 2016000619 A1 | 1/2016 |
| WO | 2016007235 A1 | 1/2016 |
| WO | WO2016061142 A1 | 4/2016 |
| WO | 2016090312 A1 | 6/2016 |

OTHER PUBLICATIONS

Brown et al J. Immunol. May 1996; 156(9):3285-3291 (Year: 1996).*
Vajdos et al (J. Mol. Biol. Jul. 5, 2002;320(2); 415-428) (Year: 2002).*
Paul, Fundamental Immunology, 3rd Edition, 1993, pp. 292-295 (Year: 1993).*
Strome et al., The Oncologist, 2007; 12:1084-95 (Year: 2007).*
Brand et al., Anticancer Res. 2006; 26:463-70 (Year: 2006).*
Kataja et al., Ann Oncol 2009; 20(sup 4): iv10-14 (Year: 2009).*
Nelson et al., Ann. Intern Med. 2009; 151:727-737 (Year: 2009).*
Balmana et al. Ann Oncol 2009; 20(supp 4):iv19-20 (Year: 2009).*
Dyck et al Eur. J. Immununol. 47:765 (2017) (Year: 2017).*
Jager, V., et al., "High level transient production of recombinant antibodies and antibody fusion proteins in HEK293 cells", "BMC biotechnology", 2013, Page(s) http://www.bomedcentral.com/1472-6750/13/52, vol. 13, No. 52, Publisher: BioMed Central.
Kuhn, P., et al., "Recombinant antibodies for diagnostics and therapy against pathogens and toxins generated by phage display", "Proteomics Clin. Appl.", 2016, pp. 922-948, vol. 10, Publisher: Wiley-VCH.
Rudikoff, S., et al., "Single amino acid substitutions altering antigen-binding specificity", "Proc. Natl. Acad. Sci. USA: Immunology", 1982, pp. 1979-1983, vol. 79.
Tamura, M., et al., "Structural Correlates of an Anticarcinoma Antibody: Identification of Specificity-Determining Residues (SDRs) and Development of a Minimally Immunogenic Antibody Variant by Retention of SDRs Only", "The Journal of Immunology", Feb. 2000, pp. 1432-1441, vol. 164, No. 3, Publisher: The American Association of Immunologists.
Panka, D., et al., "Variable region framework differences result in decreased or increased affinity of variant anti-digoxin antibodies", "Immunology", May 1988, pp. 3080-3084, vol. 85.
Xiang, J., et al., "Modificiation in Framework Region I Results in a Decreased Affinity of Chimeric Anti-Tag72 Antibody", "Molecular Immunology", 1991, pp. 141-148, vol. 28, No. ½.

(Continued)

*Primary Examiner* — Sheela J. Huff
(74) *Attorney, Agent, or Firm* — Hultquist, PLLC; Steven J. Hultquist

(57) ABSTRACT

Disclosed are an antibody to human programmed cell death-ligand 1 (PD-L1) or an antigen-binding fragment thereof, a nucleic acid encoding the same, a vector including the nucleic acid, a cell transformed with the vector, a method for producing the antibody or an antigen-binding fragment thereof, and a composition for preventing or treating cancer or infectious diseases containing the same.

10 Claims, 13 Drawing Sheets
(13 of 13 Drawing Sheet(s) Filed in Color)
Specification includes a Sequence Listing.

(56) References Cited

OTHER PUBLICATIONS

Caldas, C., et al., "Humanization of the anti-CD18 antibody 6.7: an unexpected effect of a framework residue in binding to antigen, Molecular Immunology", 2003, pp. 941-952, vol. 39, No. 15, Publisher: Pergamon.

Du, J., et al., "Molecular Basis of Recognition of Human Osteopontin by 23C3, a Potential Therapeutic Antibody for Treatment of Rheumatoid Arthritis", "Journal of Molecular Biology", 2008, pp. 835-842, vol. 382, No. 4, Publisher: Elsevier.

* cited by examiner

[Figure 1]
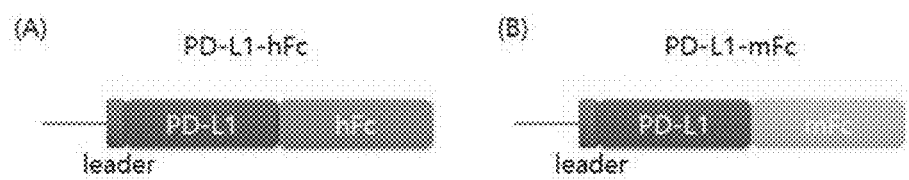
[Figure 2a]
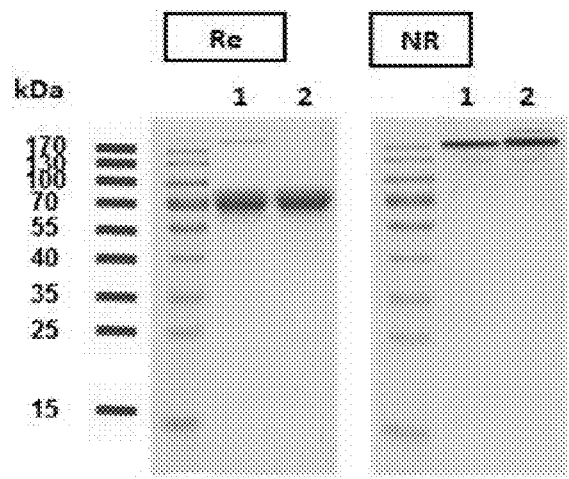

[Figure 2b]
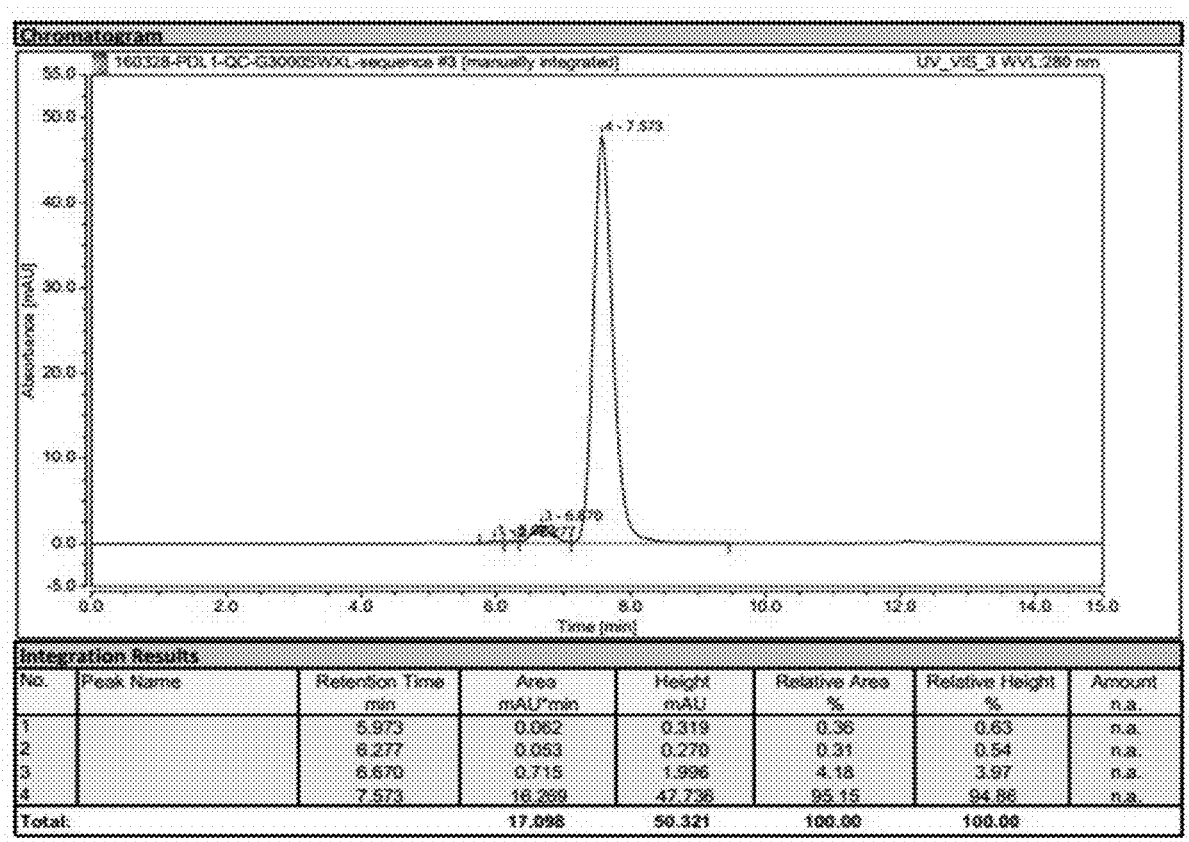

【Figure 2c】
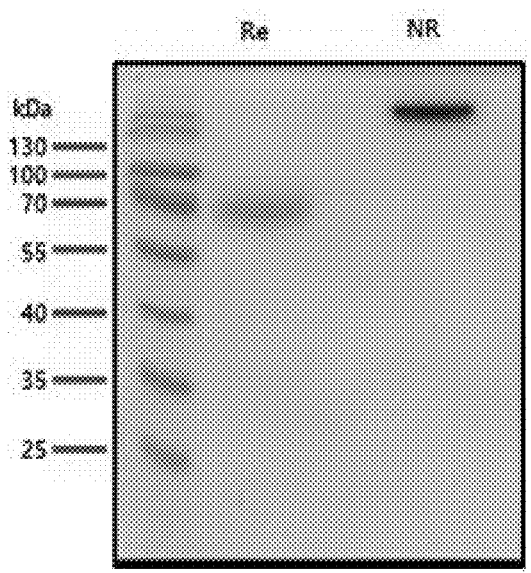
【Figure 2d】
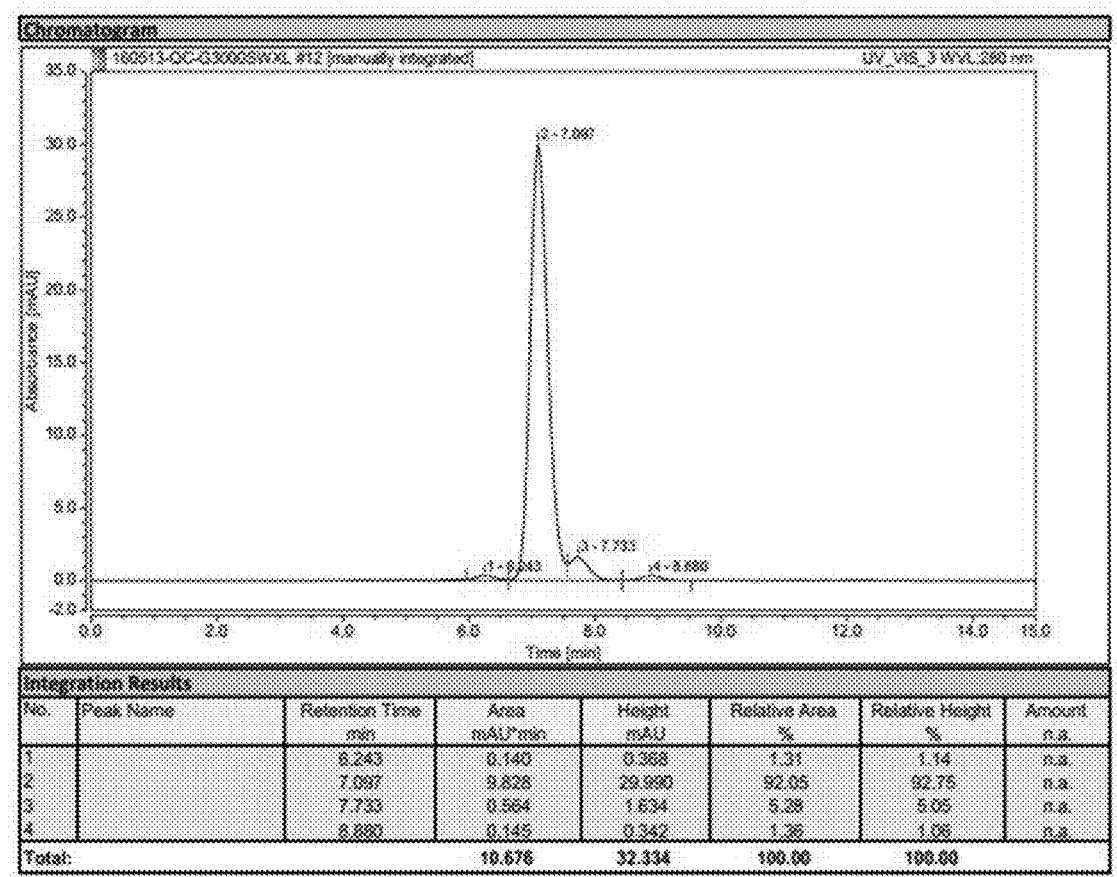

[Figure 3]
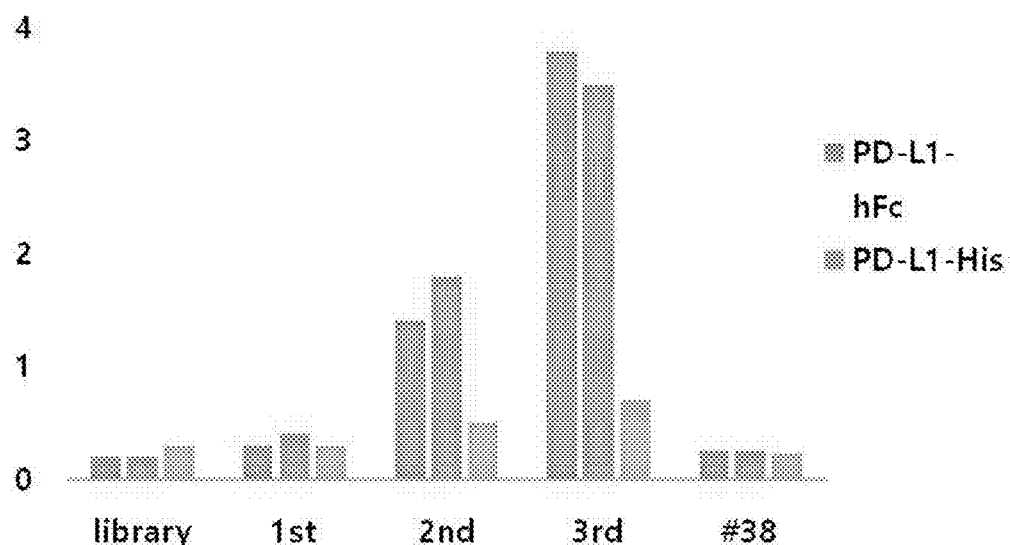
[Figure 4]
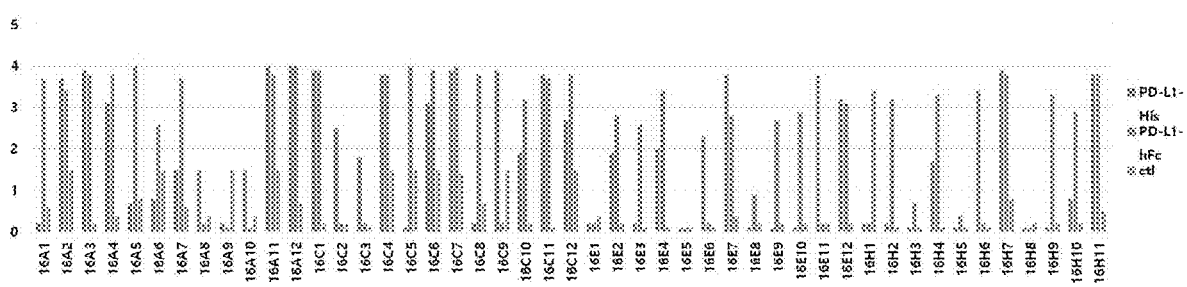

[Figure 5]
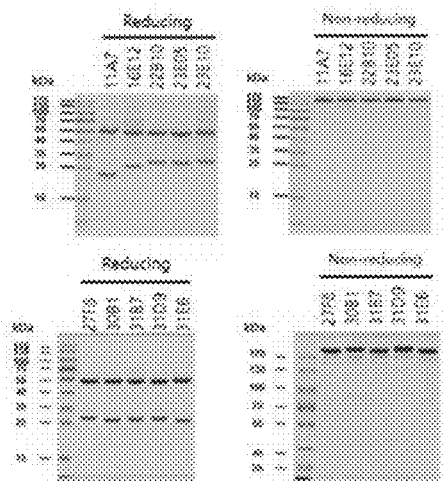
[Figure 6]
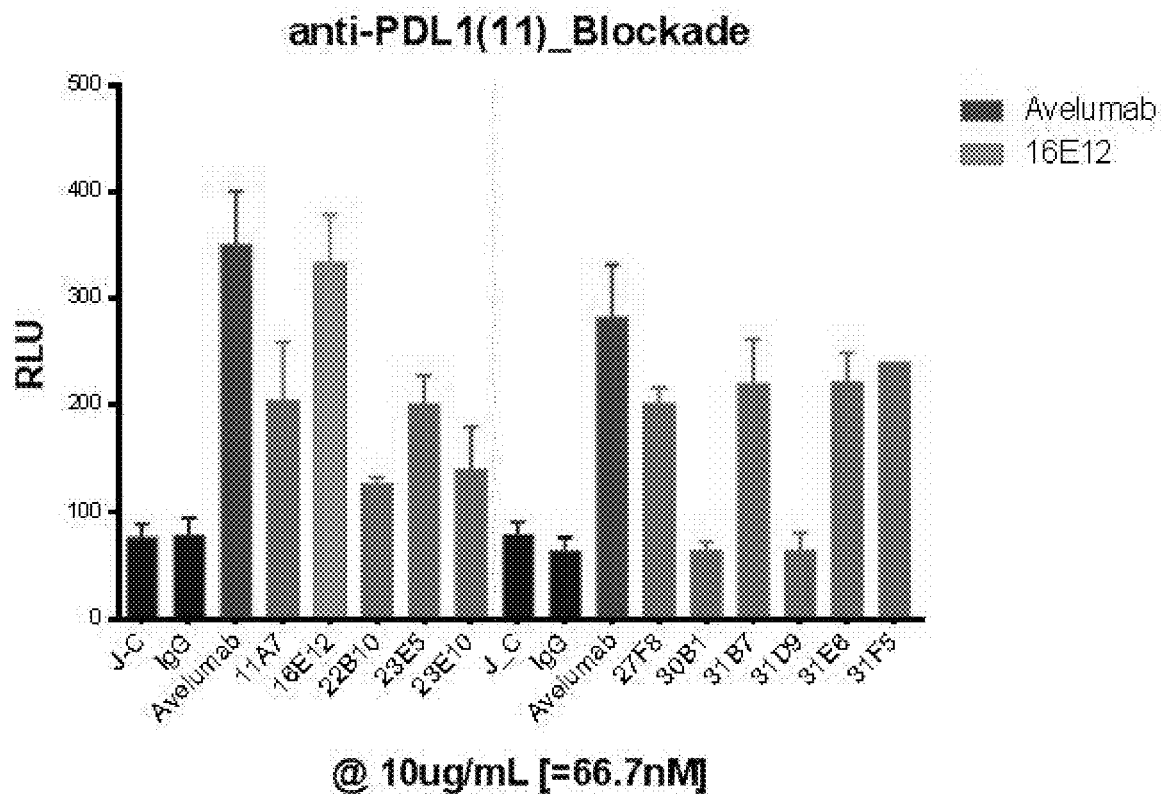

【Figure 7】
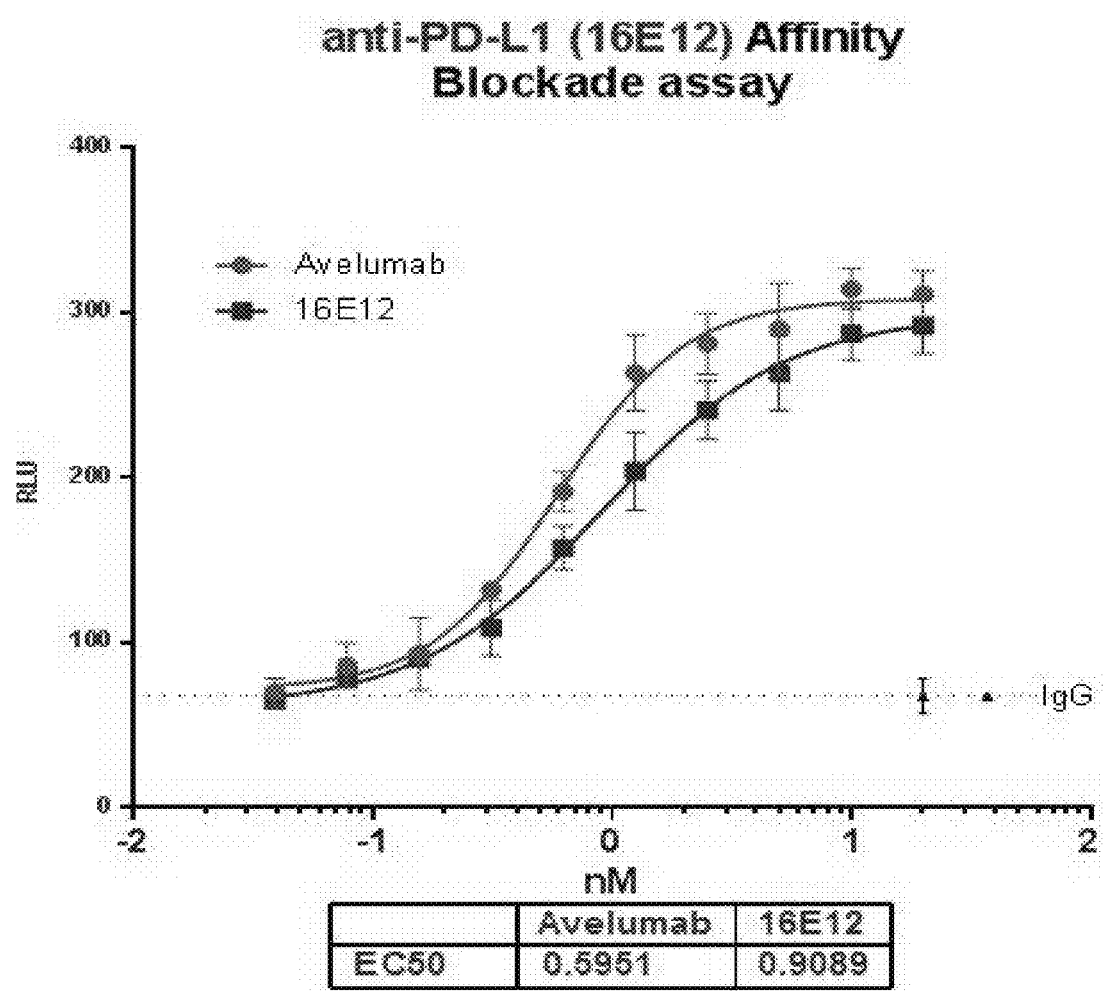

[Figure 8]
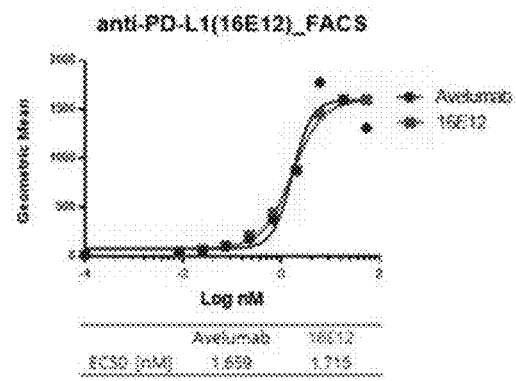
[Figure 9]
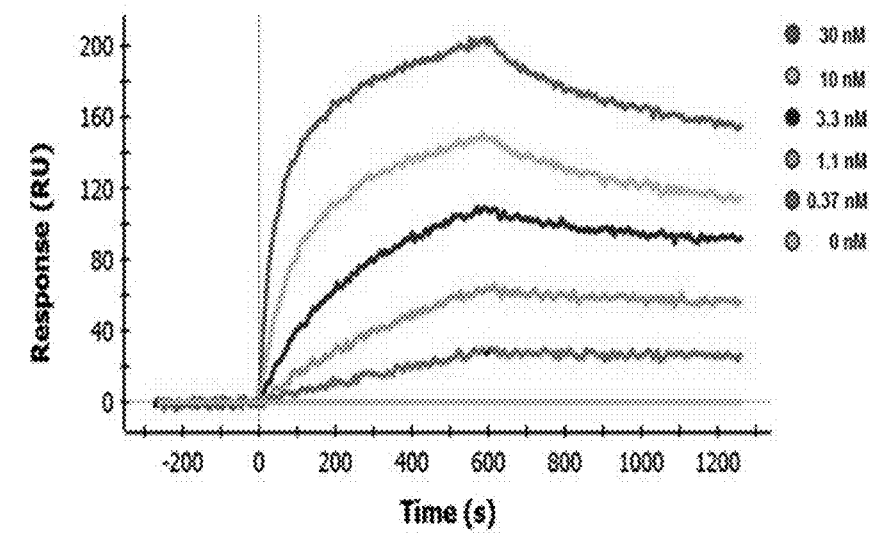

[Figure 10]
[Figure 11]
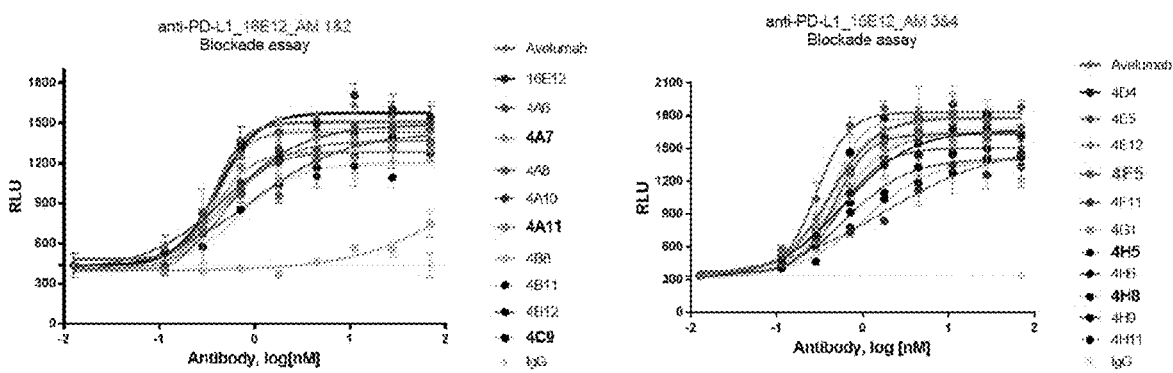

[Figure 12]
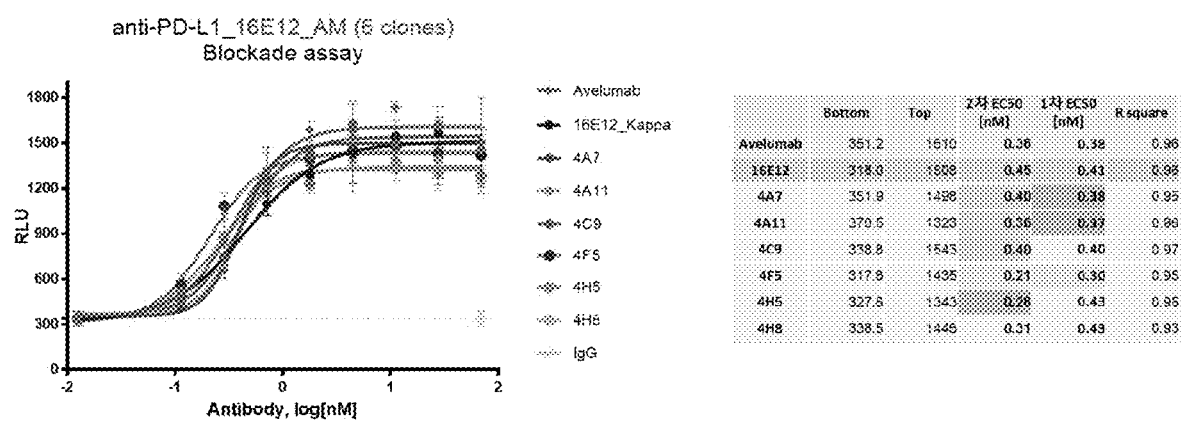
[Figure 13]
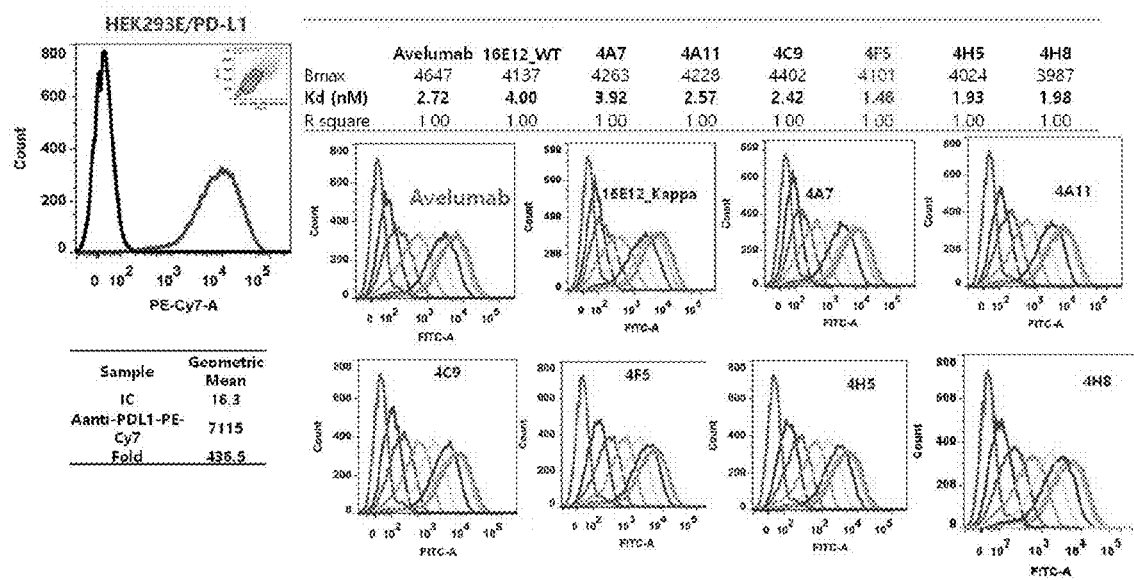

【Figure 14】
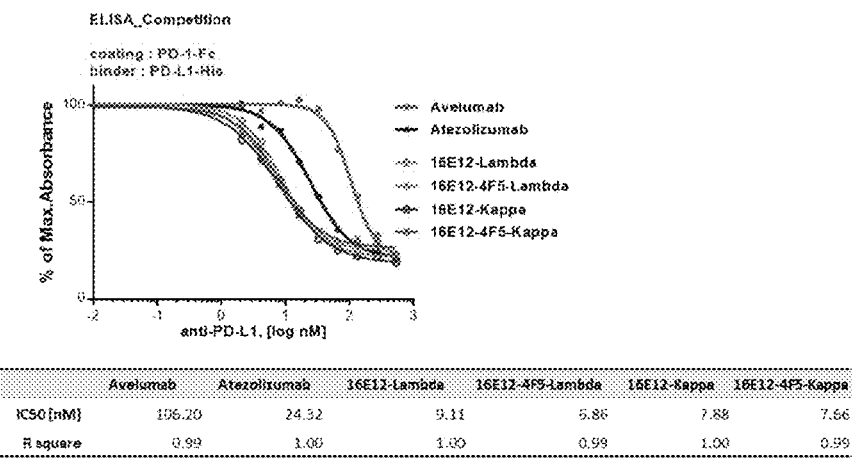
【Figure 15】
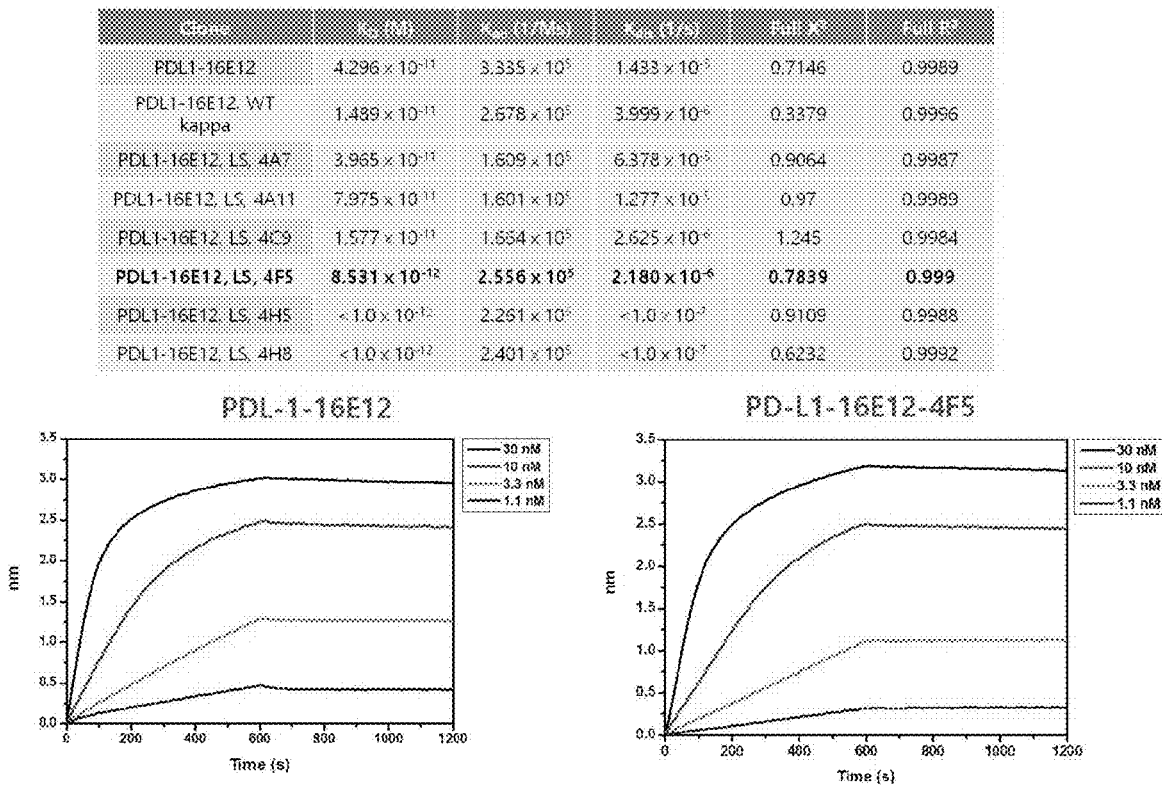

[Figure 16]

*Mutated Amino acid marked with Red

Showing lower value if the binidng ability gets lower

[Figure 17]
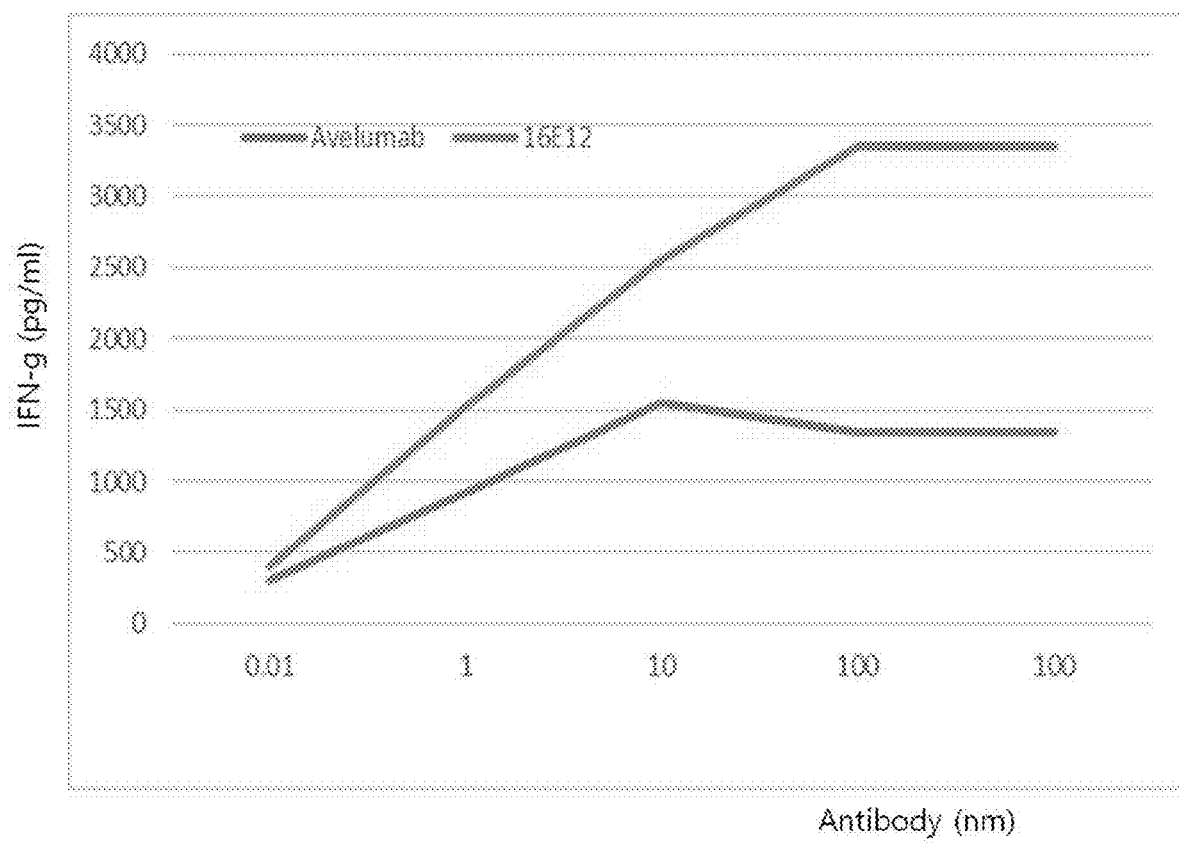
[Figure 18]
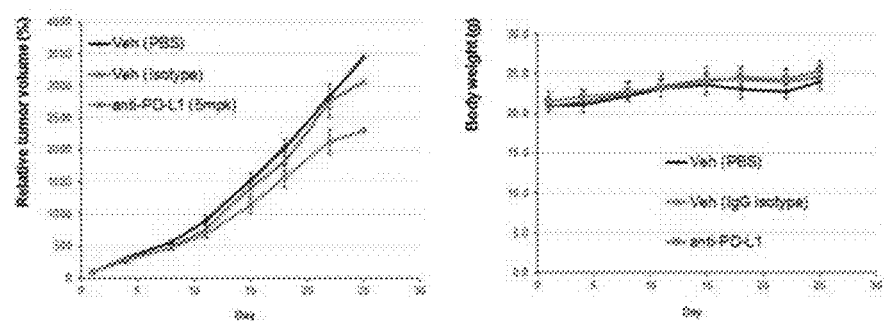

[Figure 19]
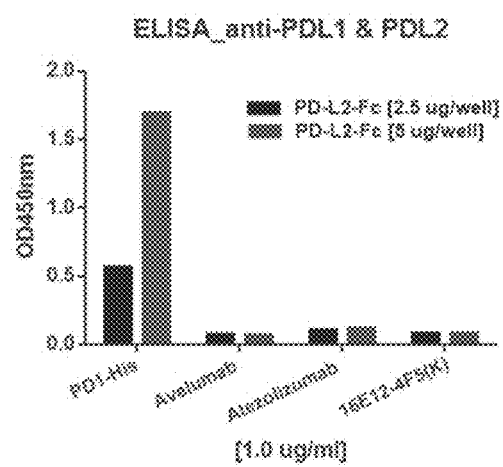

SEQUENCE LISTING

```
<160> NUMBER OF SEQ ID NOS: 260

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Leu Thr Glu Leu Ser
1               5

<210> SEQ ID NO 2
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Gly Gly Thr Phe Ser Ser Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Gly Asp Thr Phe Ser Arg Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Gly Glu Asn Phe Arg Ser His Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Gly Gly Thr Phe Ser Ser Ser Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Gly Phe Thr Phe Ser Ser Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gly Phe Thr Phe Ser Ser Tyr Val
1               5

<210> SEQ ID NO 8
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 8

Phe Asp Pro Glu Asp Gly Glu Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ile Ile Pro Ile Leu Gly Ile Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ile Ile Pro Val Leu Gly Ala Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

Ile Ile Pro Ile Val Gly Leu Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Ile Ile Pro Met Phe Asp Met Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Ile Ser Tyr Asp Gly Ser Asn Glu
1               5

<210> SEQ ID NO 14
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 14

Ile Ser Ser Asn Gly Gly Ser Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ile Ile Pro Ile Phe Gly Thr Ala
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Ala Arg Asp Pro Trp Gly Gly Tyr Tyr Gly Met Asp Val
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Ala Lys Pro Arg Asp Gly Tyr Asn Leu Val Ala Phe Asp Ile
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Ala Arg Asp Phe Val Leu Ser Gly Ser Ala Thr Val Phe Asp Pro
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Ala Arg Ser Leu Ser Gly Tyr Ser Leu Gly Ala Phe Asp Val
1               5                   10

<210> SEQ ID NO 20
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 20

Val Thr Gly Arg Pro Pro Trp His
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Ala Arg Ser Asn Pro His Tyr Met Asp Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Ala Arg Gly Asp Tyr Asn Gly Val Tyr Met Asp Val
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic Construct

<400> SEQUENCE: 23

Ala Arg Ala Ser Ser Gly Tyr Ser Val Gly Ala Phe Asp Ile
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Ala Arg Glu His Phe Ser Thr Tyr Ser Tyr Gly Val Asp Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Ala Arg Gly Gly Arg Ser Phe Gly Ala Phe Asp Ser
1               5                   10

<210> SEQ ID NO 26
<211> LENGTH: 25
<212> TYPE: PRT
<213> ORGANISM: Artificial Sequence
<220> FEATURE:
```

```
<223> OTHER INFORMATION: Synthetic Construct

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Val Ser
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic Construct

<400> SEQUENCE: 27

Gln Met Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Ala Glu Val Lys Lys Pro Gly Ser
1               5                   10                  15

Ser Val Lys Val Ser Cys Arg Ala Ser
            20                  25

<210> SEQ ID NO 29
<211> LENGTH: 25
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Val Lys Pro Gly Ser
1               5                   10                  15

Ser Val Lys Val Ser Cys Lys Ala Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic Construct

<400> SEQUENCE: 30

Gln Met Gln Leu Val Glu Ser Gly Ala Glu Val Lys Lys Pro Gly Ser
1               5                   10                  15

Ser Val Lys Val Ser Cys Lys Val Ser
            20                  25

<210> SEQ ID NO 31
<211> LENGTH: 25
<212> TYPE: PRT
<213> ORGANISM: Artificial Sequence
```

<220> FEATURE:
<223> OTHER INFORMATION: Synthetic Construct

<400> SEQUENCE: 31

Gln Val Gln Leu Val Gln Ser Gly Ala Glu Val Lys Pro Gly Ser
1               5                   10                  15

Ser Val Lys Val Ser Cys Lys Ala Ser
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Val Glu Ser Gly Ala Glu Val Lys Lys Pro Gly Ser
1               5                   10                  15

Ser Val Lys Val Ser Cys Lys Ala Ser
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic Construct

<400> SEQUENCE: 34

Gln Met Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 35
<211> LENGTH: 17
<212> TYPE: PRT
<213> ORGANISM: Artificial Sequence
<220> FEATURE:
<223> OTHER INFORMATION: Synthetic Construct

<400> SEQUENCE: 35

Met His Trp Val Arg Gln Ala Pro Gly Lys Gly Leu Glu Trp Met Gly
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Ile Ser Trp Val Arg Gln Ala Pro Gly Gln Gly Leu Glu Trp Met Gly
1               5                   10                  15
Arg

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Ile Ser Trp Val Arg Gln Ala Pro Gly Gln Ala Pro Glu Trp Met Gly
1               5                   10                  15
Arg

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38

Phe Ser Trp Val Arg Gln Ala Pro Gly His Gly Leu Glu Trp Met Gly
1               5                   10                  15
Arg

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Met His Trp Val Arg Gln Gly Pro Gly Lys Gly Leu Glu Trp Val Ala
1               5                   10                  15
Val

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Met His Trp Val Arg Gln Ala Pro Gly Lys Gly Leu Glu Tyr Val Ser
1               5                   10                  15
Ala

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Ile Ser Trp Val Arg Gln Ala Pro Gly Gln Gly Leu Glu Trp Met Gly
1               5                   10                  15

Gly

<210> SEQ ID NO 42
<211> LENGTH: 38
<212> TYPE: PRT
<213> ORGANISM: Artificial Sequence
<220> FEATURE:
<223> OTHER INFORMATION: Synthetic Construct

<400> SEQUENCE: 42

Ile Tyr Ala Gln Lys Phe Gln Gly Arg Val Thr Met Thr Glu Asp Thr
1               5                   10                  15

Ser Thr Asp Thr Ala Tyr Met Glu Leu Ser Ser Leu Arg Ser Glu Asp
            20                  25                  30

Thr Ala Val Tyr Tyr Cys
        35

<210> SEQ ID NO 43
<211> LENGTH: 38
<212> TYPE: PRT
<213> ORGANISM: Artificial Sequence
<220> FEATURE:
<223> OTHER INFORMATION: Synthetic Construct

<400> SEQUENCE: 43

Asn Tyr Ala Gln Lys Phe Gln Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 44
<211> LENGTH: 38
<212> TYPE: PRT
<213> ORGANISM: Artificial Sequence
<220> FEATURE:
<223> OTHER INFORMATION: Synthetic Construct

<400> SEQUENCE: 44

Asn Tyr Ala Arg Lys Phe Gln Asp Arg Val Thr Ile Thr Ala Asp Ile
1               5                   10                  15

Ser Thr Thr Thr Ala Phe Met Glu Leu Thr Ser Leu Arg Ser Glu Asp
            20                  25                  30

Thr Ala Val Tyr Tyr Cys
        35

<210> SEQ ID NO 45
<211> LENGTH: 38
<212> TYPE: PRT
<213> ORGANISM: Artificial Sequence
<220> FEATURE:
<223> OTHER INFORMATION: Synthetic Construct

<400> SEQUENCE: 45

Asp Tyr Pro Gln Lys Phe Gln Gly Arg Val Thr Ile Ser Ala Asp Glu
1               5                   10                  15

Ser Thr Gly Thr Ala Tyr Met Asp Leu Ser Ser Leu Arg Ser Glu Asp
            20                  25                  30

-continued

Thr Ala Val Tyr Tyr Cys
        35

<210> SEQ ID NO 46
<211> LENGTH: 38
<212> TYPE: PRT
<213> ORGANISM: Artificial Sequence
<220> FEATURE:
<223> OTHER INFORMATION: Synthetic Construct

<400> SEQUENCE: 46

Asp Tyr Ala Gln Arg Phe Gln Gly Arg Leu Thr Ile Ile Ala Asp Glu
1               5                   10                  15

Ser Ser Ser Thr Ala Tyr Met Glu Leu Ser Ser Leu Arg Ser Glu Asp
            20                  25                  30

Thr Ala Val Tyr Tyr Cys
        35

<210> SEQ ID NO 47
<211> LENGTH: 38
<212> TYPE: PRT
<213> ORGANISM: Artificial Sequence
<220> FEATURE:
<223> OTHER INFORMATION: Synthetic Construct

<400> SEQUENCE: 47

Phe Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 48
<211> LENGTH: 38
<212> TYPE: PRT
<213> ORGANISM: Artificial Sequence
<220> FEATURE:
<223> OTHER INFORMATION: Synthetic Construct

<400> SEQUENCE: 48

Tyr Tyr Ala Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ser Glu Asp
            20                  25                  30

Thr Ala Val Tyr Tyr Cys
        35

<210> SEQ ID NO 49
<211> LENGTH: 38
<212> TYPE: PRT
<213> ORGANISM: Artificial Sequence
<220> FEATURE:
<223> OTHER INFORMATION: Synthetic Construct

<400> SEQUENCE: 49

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

```
<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Trp Gly Gln Gly Thr Thr Val Thr Val Ser Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Trp Gly Gln Gly Thr Met Val Thr Val Ser Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Trp Gly Gln Gly Thr Leu Val Thr Val Ser Ser
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Trp Gly Pro Gly Thr Leu Val Thr Val Ser Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Trp Gly Gln Gly Ile Leu Ile Thr Val Ser Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Trp Gly Pro Gly Thr Thr Val Thr Val Ser Ser
1               5                   10
```

```
<210> SEQ ID NO 56
<211> LENGTH: 11
<212> TYPE: PRT
<213> ORGANISM: Artificial Sequence
<220> FEATURE:
<223> OTHER INFORMATION: Synthetic Construct

<400> SEQUENCE: 56

Trp Gly Gln Gly Ala Leu Val Thr Val Ser Ser
1               5                   10

<210> SEQ ID NO 57
<211> LENGTH: 120
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Trp Gly Gly Tyr Tyr Gly Met Asp Val Trp Gly Gln
            100                 105                 110

Gly Thr Thr Val Thr Val Ser Ser
        115                 120

<210> SEQ ID NO 58
<211> LENGTH: 121
<212> TYPE: PRT
<213> ORGANISM: Artificial Sequence
<220> FEATURE:
<223> OTHER INFORMATION: Synthetic Construct

<400> SEQUENCE: 58

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120
```

<210> SEQ ID NO 59
<211> LENGTH: 122
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Val Gln Ser Gly Ala Glu Val Lys Lys Pro Gly Ser
1               5                   10                  15

Ser Val Lys Val Ser Cys Arg Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Val Leu Ser Gly Ser Ala Thr Val Phe Asp Pro Trp
            100                 105                 110

Gly Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Val Lys Pro Gly Ser
1               5                   10                  15

Ser Val Lys Val Ser Cys Lys Ala Ser Gly Asp Thr Phe Ser Arg Tyr
            20                  25                  30

Ala Ile Ser Trp Val Arg Gln Ala Pro Gly Gln Ala Pro Glu Trp Met
        35                  40                  45

Gly Arg Ile Ile Pro Val Leu Gly Ala Ala Asn Tyr Ala Arg Lys Phe
    50                  55                  60

Gln Asp Arg Val Thr Ile Thr Ala Asp Ile Ser Thr Thr Thr Ala Phe
65                  70                  75                  80

Met Glu Leu Thr Ser Leu Arg Ser Glu Asp Thr Ala Val Tyr Tyr Cys
                85                  90                  95

Ala Arg Ser Leu Ser Gly Tyr Ser Leu Gly Ala Phe Asp Val Trp Gly
            100                 105                 110

Pro Gly Thr Leu Val Thr Val Ser Ser
        115                 120

<210> SEQ ID NO 61
<211> LENGTH: 115
<212> TYPE: PRT
<213> ORGANISM: Artificial Sequence
<220> FEATURE:
<223> OTHER INFORMATION: Synthetic Construct

<400> SEQUENCE: 61

Gln Met Gln Leu Val Glu Ser Gly Ala Glu Val Lys Lys Pro Gly Ser
1               5                   10                  15

Ser Val Lys Val Ser Cys Lys Val Ser Gly Glu Asn Phe Arg Ser His
            20                  25                  30

Ala Ile Ser Trp Val Arg Gln Ala Pro Gly Gln Gly Leu Glu Trp Met
        35                  40                  45

Gly Arg Ile Ile Pro Ile Val Gly Leu Ala Asp Tyr Pro Gln Lys Phe
50                  55                  60

Gln Gly Arg Val Thr Ile Ser Ala Asp Glu Ser Thr Gly Thr Ala Tyr
65                  70                  75                  80

Met Asp Leu Ser Ser Leu Arg Ser Glu Asp Thr Ala Val Tyr Tyr Cys
                85                  90                  95

Val Thr Gly Arg Pro Pro Trp His Trp Gly Gln Gly Ile Leu Ile Thr
            100                 105                 110

Val Ser Ser
        115

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Phe Ser Trp Val Arg Gln Ala Pro Gly His Gly Leu Glu Trp Met
        35                  40                  45

Gly Arg Ile Ile Pro Met Phe Asp Met Thr Asp Tyr Ala Gln Arg Phe
50                  55                  60

Gln Gly Arg Leu Thr Ile Ile Ala Asp Glu Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Pro His Tyr Met Asp Val Trp Gly Gln Gly Thr Thr
            100                 105                 110

Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ser Gly Phe Thr Phe Ser Ser Tyr
            20                  25                  30

Ala Met His Trp Val Arg Gln Gly Pro Gly Lys Gly Leu Glu Trp Val
        35                  40                  45

Ala Val Ile Ser Tyr Asp Gly Ser Asn Glu Phe Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Tyr Asn Gly Val Tyr Met Asp Val Trp Gly Gln Gly
            100                 105                 110

Thr Thr Val Thr Val Ser Ser
        115

<210> SEQ ID NO 64
<211> LENGTH: 121
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Glu Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Ser Ser Gly Tyr Ser Val Gly Ala Phe Asp Ile Trp Gly
            100                 105                 110

Gln Gly Thr Met Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Synthetic Construct

<400> SEQUENCE: 65

Gln Met Gln Leu Val Glu Ser Gly Gly Gly Leu Val Gln Pro Gly Gly
 1               5                  10                  15

Ser Leu Arg Leu Ser Cys Ser Ala Ser Gly Phe Thr Phe Ser Ser Tyr
                 20                  25                  30

Val Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ser Glu Asp Thr Ala Val Tyr Tyr Cys
                 85                  90                  95

Ala Arg Glu His Phe Ser Thr Tyr Ser Tyr Gly Val Asp Val Trp Gly
            100                 105                 110

Pro Gly Thr Thr Val Thr Val Ser Ser
```

<210> SEQ ID NO 66
<211> LENGTH: 119
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ser Phe Gly Ala Phe Asp Ser Trp Gly Gln Gly
            100                 105                 110

Ala Leu Val Thr Val Ser Ser
        115

<210> SEQ ID NO 67
<211> LENGTH: 121
<212> TYPE: PRT
<213> ORGANISM: Artificial Sequence
<220> FEATURE:
<223> OTHER INFORMATION: Synthetic Construct

<400> SEQUENCE: 67

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Synthetic Construct

<400> SEQUENCE: 68

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
                100                 105                 110

Gln Gly Thr Met Val Thr Val Ser Ser
            115                 120

<210> SEQ ID NO 69
<211> LENGTH: 121
<212> TYPE: PRT
<213> ORGANISM: Artificial Sequence
<220> FEATURE:
<223> OTHER INFORMATION: Synthetic Construct

<400> SEQUENCE: 69

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
                100                 105                 110

Gln Gly Thr Met Val Thr Val Ser Ser
            115                 120

<210> SEQ ID NO 70
<211> LENGTH: 121
<212> TYPE: PRT
<213> ORGANISM: Artificial Sequence
<220> FEATURE:
<223> OTHER INFORMATION: Synthetic Construct

<400> SEQUENCE: 70

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe

```
                50                  55                  60
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Pro Arg Asp Gly Tyr Asn Leu Val Ala Phe Asp Ile Trp Gly
                100                 105                 110

Gln Gly Thr Met Val Thr Val Ser Ser
                115                 120

<210> SEQ ID NO 71
<211> LENGTH: 121
<212> TYPE: PRT
<213> ORGANISM: Artificial Sequence
<220> FEATURE:
<223> OTHER INFORMATION: Synthetic Construct

<400> SEQUENCE: 71

Gln Met Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
                 35                  40                  45

Gly Arg Ile Ile Pro Ile Leu Gly Ile Ala Asn Tyr Ala Gln Lys Phe
             50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Pro Arg Asp Gly Tyr Asn Leu Val Ala Phe Asp Ile Trp Gly
                100                 105                 110

Gln Gly Thr Met Val Thr Val Ser Ser
                115                 120

<210> SEQ ID NO 72
<211> LENGTH: 121
<212> TYPE: PRT
<213> ORGANISM: Artificial Sequence
<220> FEATURE:
<223> OTHER INFORMATION: Synthetic Construct

<400> SEQUENCE: 72

Gln Met Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
                 35                  40                  45

Gly Arg Ile Ile Pro Ile Leu Gly Ile Ala Asn Tyr Ala Gln Lys Phe
             50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Pro Arg Asp Gly Tyr Asn Leu Val Ala Phe Asp Ile Trp Gly
                100                 105                 110
```

```
Gln Gly Thr Met Val Thr Val Ser Ser
        115                 120

<210> SEQ ID NO 73
<211> LENGTH: 121
<212> TYPE: PRT
<213> ORGANISM: Artificial Sequence
<220> FEATURE:
<223> OTHER INFORMATION: Synthetic Construct

<400> SEQUENCE: 73

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 74
<211> LENGTH: 121
<212> TYPE: PRT
<213> ORGANISM: Artificial Sequence
<220> FEATURE:
<223> OTHER INFORMATION: Synthetic Construct

<400> SEQUENCE: 74

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 75
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 75

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
            115                 120

<210> SEQ ID NO 76
<211> LENGTH: 121
<212> TYPE: PRT
<213> ORGANISM: Artificial Sequence
<220> FEATURE:
<223> OTHER INFORMATION: Synthetic Construct

<400> SEQUENCE: 76

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
            115                 120

<210> SEQ ID NO 77
<211> LENGTH: 121
<212> TYPE: PRT
<213> ORGANISM: Artificial Sequence
<220> FEATURE:
<223> OTHER INFORMATION: Synthetic Construct

<400> SEQUENCE: 77

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 78
<211> LENGTH: 121
<212> TYPE: PRT
<213> ORGANISM: Artificial Sequence
<220> FEATURE:
<223> OTHER INFORMATION: Synthetic Construct

<400> SEQUENCE: 78

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 79
<211> LENGTH: 121
<212> TYPE: PRT
<213> ORGANISM: Artificial Sequence
<220> FEATURE:
<223> OTHER INFORMATION: Synthetic Construct

<400> SEQUENCE: 79

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

```
Gln Gly Thr Met Val Thr Val Ser Ser
        115                 120

<210> SEQ ID NO 80
<211> LENGTH: 121
<212> TYPE: PRT
<213> ORGANISM: Artificial Sequence
<220> FEATURE:
<223> OTHER INFORMATION: Synthetic Construct

<400> SEQUENCE: 80

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 81
<211> LENGTH: 121
<212> TYPE: PRT
<213> ORGANISM: Artificial Sequence
<220> FEATURE:
<223> OTHER INFORMATION: Synthetic Construct

<400> SEQUENCE: 81

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 82
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 82

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 83
<211> LENGTH: 121
<212> TYPE: PRT
<213> ORGANISM: Artificial Sequence
<220> FEATURE:
<223> OTHER INFORMATION: Synthetic Construct

<400> SEQUENCE: 83

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 84
<211> LENGTH: 121
<212> TYPE: PRT
<213> ORGANISM: Artificial Sequence
<220> FEATURE:
<223> OTHER INFORMATION: Synthetic Construct

<400> SEQUENCE: 84

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
            115                 120

<210> SEQ ID NO 85
<211> LENGTH: 121
<212> TYPE: PRT
<213> ORGANISM: Artificial Sequence
<220> FEATURE:
<223> OTHER INFORMATION: Synthetic Construct

<400> SEQUENCE: 85

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
            115                 120

<210> SEQ ID NO 86
<211> LENGTH: 121
<212> TYPE: PRT
<213> ORGANISM: Artificial Sequence
<220> FEATURE:
<223> OTHER INFORMATION: Synthetic Construct

<400> SEQUENCE: 86

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly

```
                    100                 105                 110

Gln Gly Thr Met Val Thr Val Ser Ser
        115                 120

<210> SEQ ID NO 87
<211> LENGTH: 121
<212> TYPE: PRT
<213> ORGANISM: Artificial Sequence
<220> FEATURE:
<223> OTHER INFORMATION: Synthetic Construct

<400> SEQUENCE: 87

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120

<210> SEQ ID NO 88
<211> LENGTH: 6
<212> TYPE: PRT
<213> ORGANISM: Artificial Sequence
<220> FEATURE:
<223> OTHER INFORMATION: Synthetic Construct

<400> SEQUENCE: 88

Gln Gly Ile Arg Thr Trp
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Ser Ser Asn Ile Gly Ala Gly Tyr Asp
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Ser Thr Asn Ile Gly Ala Gly Tyr Asp
1               5
```

```
<210> SEQ ID NO 91
<211> LENGTH: 9
<212> TYPE: PRT
<213> ORGANISM: Artificial Sequence
<220> FEATURE:
<223> OTHER INFORMATION: Synthetic Construct

<400> SEQUENCE: 91

Asn Ser Asn Ile Gly Thr Pro Tyr Asp
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Asn Ser Asp Ile Gly Ala Gly His Asp
1               5

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct

<400> SEQUENCE: 93

Gln Ser Leu Leu His Ser Asp Gly Lys Thr Tyr
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Ser Ser Asn Ile Gly Asn Asn Tyr
1               5

<210> SEQ ID NO 95
<211> LENGTH: 12
<212> TYPE: PRT
<213> ORGANISM: Artificial Sequence
<220> FEATURE:
<223> OTHER INFORMATION: Synthetic Construct

<400> SEQUENCE: 95

Gln Ser Leu Leu Asp Ser Asp Asp Gly Asn Thr Tyr
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Synthetic Construct

<400> SEQUENCE: 96

Gln Ser Ile Ser Ser Tyr
1               5

<210> SEQ ID NO 97
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Asn Ser Asn Ile Gly Ala Gly Tyr Asp
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Construct

<400> SEQUENCE: 98

Asn Ser Asn Ile Gly Ala Gly His Asp
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Construct

<400> SEQUENCE: 99

Ser Ser Asn Leu Gly Ala Pro Tyr Asp
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Construct

<400> SEQUENCE: 100

Ser Ser Asn Ile Gly Ala Gly Ser Asp
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Arg Ser Asn Phe Gly Ala Gly His Asp
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct

<400> SEQUENCE: 102

Ser Ser Asn Val Gly Ala Gly Tyr Asp
1               5

<210> SEQ ID NO 103
<211> LENGTH: 3
```

```
<212> TYPE: PRT
<213> ORGANISM: Artificial Sequence
<220> FEATURE:
<223> OTHER INFORMATION: Synthetic Construct

<400> SEQUENCE: 103

Ala Ala Ser
1

<210> SEQ ID NO 104
<211> LENGTH: 3
<212> TYPE: PRT
<213> ORGANISM: Artificial Sequence
<220> FEATURE:
<223> OTHER INFORMATION: Synthetic Construct

<400> SEQUENCE: 104

Gly Asn Asn
1

<210> SEQ ID NO 105
<211> LENGTH: 3
<212> TYPE: PRT
<213> ORGANISM: Artificial Sequence
<220> FEATURE:
<223> OTHER INFORMATION: Synthetic Construct

<400> SEQUENCE: 105

Gly Asn Ser
1

<210> SEQ ID NO 106
<211> LENGTH: 3
<212> TYPE: PRT
<213> ORGANISM: Artificial Sequence
<220> FEATURE:
<223> OTHER INFORMATION: Synthetic Construct

<400> SEQUENCE: 106

Gly Ser Thr
1

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Ser Asn Arg
1

<210> SEQ ID NO 108
<211> LENGTH: 3
<212> TYPE: PRT
<213> ORGANISM: Artificial Sequence
<220> FEATURE:
<223> OTHER INFORMATION: Synthetic Construct

<400> SEQUENCE: 108

Gly Asn Thr
1

<210> SEQ ID NO 109
<211> LENGTH: 3
<212> TYPE: PRT
```

```
<213> ORGANISM: Artificial Sequence
<220> FEATURE:
<223> OTHER INFORMATION: Synthetic Construct

<400> SEQUENCE: 109

Glu Val Ser
1

<210> SEQ ID NO 110
<211> LENGTH: 3
<212> TYPE: PRT
<213> ORGANISM: Artificial Sequence
<220> FEATURE:
<223> OTHER INFORMATION: Synthetic Construct

<400> SEQUENCE: 110

Asp Asn Asn
1

<210> SEQ ID NO 111
<211> LENGTH: 3
<212> TYPE: PRT
<213> ORGANISM: Artificial Sequence
<220> FEATURE:
<223> OTHER INFORMATION: Synthetic Construct

<400> SEQUENCE: 111

Met Ile Ser
1

<210> SEQ ID NO 112
<211> LENGTH: 3
<212> TYPE: PRT
<213> ORGANISM: Artificial Sequence
<220> FEATURE:
<223> OTHER INFORMATION: Synthetic Construct

<400> SEQUENCE: 112

Asp Ser Ser
1

<210> SEQ ID NO 113
<211> LENGTH: 3
<212> TYPE: PRT
<213> ORGANISM: Artificial Sequence
<220> FEATURE:
<223> OTHER INFORMATION: Synthetic Construct

<400> SEQUENCE: 113

Gly Asp Asn
1

<210> SEQ ID NO 114
<211> LENGTH: 3
<212> TYPE: PRT
<213> ORGANISM: Artificial Sequence
<220> FEATURE:
<223> OTHER INFORMATION: Synthetic Construct

<400> SEQUENCE: 114

Thr Asn His
1

<210> SEQ ID NO 115
<211> LENGTH: 3
<212> TYPE: PRT
<213> ORGANISM: Artificial Sequence
```

```
<220> FEATURE:
<223> OTHER INFORMATION: Synthetic Construct

<400> SEQUENCE: 115

Gly Asp Arg
1

<210> SEQ ID NO 116
<211> LENGTH: 3
<212> TYPE: PRT
<213> ORGANISM: Artificial Sequence
<220> FEATURE:
<223> OTHER INFORMATION: Synthetic Construct

<400> SEQUENCE: 116

Gly Asp Thr
1

<210> SEQ ID NO 117
<211> LENGTH: 3
<212> TYPE: PRT
<213> ORGANISM: Artificial Sequence
<220> FEATURE:
<223> OTHER INFORMATION: Synthetic Construct

<400> SEQUENCE: 117

Glu Asn Ser
1

<210> SEQ ID NO 118
<211> LENGTH: 3
<212> TYPE: PRT
<213> ORGANISM: Artificial Sequence
<220> FEATURE:
<223> OTHER INFORMATION: Synthetic Construct

<400> SEQUENCE: 118

Ala Asn Thr
1

<210> SEQ ID NO 119
<211> LENGTH: 3
<212> TYPE: PRT
<213> ORGANISM: Artificial Sequence
<220> FEATURE:
<223> OTHER INFORMATION: Synthetic Construct

<400> SEQUENCE: 119

Gly Asp Ile
1

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct

<400> SEQUENCE: 120

Gln Gln Ala Asn Ser Phe Pro Leu Thr
1               5

<210> SEQ ID NO 121
<211> LENGTH: 12
<212> TYPE: PRT
<213> ORGANISM: Artificial Sequence
<220> FEATURE:
```

<223> OTHER INFORMATION: Synthetic Construct

<400> SEQUENCE: 121

Gln Ser Tyr Asp Asn Ser Leu Ser Ala His Ala Val
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic Construct

<400> SEQUENCE: 122

Gln Ser Tyr Asp Ser Ser Leu Ser Gly Tyr Val
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic Construct

<400> SEQUENCE: 123

Gln Ser Tyr Asp Arg Ser Leu Gly Val Ser Asp Val Val
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic Construct

<400> SEQUENCE: 124

Gln Ser Tyr Asp Ser Ser Leu Ser Gly Pro Asn Tyr Val
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Met Gln Gly Leu His Leu Pro Tyr Thr
1               5

<210> SEQ ID NO 126
<211> LENGTH: 11
<212> TYPE: PRT
<213> ORGANISM: Artificial Sequence
<220> FEATURE:
<223> OTHER INFORMATION: Synthetic Construct

<400> SEQUENCE: 126

Gly Thr Trp Asp Ser Ser Leu Ser Ala Gly Val
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Synthetic Construct

<400> SEQUENCE: 127

Met Gln Arg Val Glu Phe Pro Tyr Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Construct

<400> SEQUENCE: 128

Gln Gln Arg Gly Gln Trp Pro Leu Thr
1               5

<210> SEQ ID NO 129
<211> LENGTH: 12
<212> TYPE: PRT
<213> ORGANISM: Artificial Sequence
<220> FEATURE:
<223> OTHER INFORMATION: Synthetic Construct

<400> SEQUENCE: 129

Gln Ser Phe Asp Arg Ser Arg Ser Gly Ser Asn Val
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic Construct

<400> SEQUENCE: 130

His Ser Tyr Asp Gly Ser Leu Ser Glu Gly Val
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Gln Ser Phe Asp Ser Arg Leu Gly Val Val
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic Construct

<400> SEQUENCE: 132

Gln Ser Tyr Asp Asn Ser Leu Arg Gly Ser Val
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic Construct

<400> SEQUENCE: 133

Gln Ser Tyr Asp Asn Arg Leu Ser Gly Ser Leu
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic Construct

<400> SEQUENCE: 134

Gln Ser Tyr Asp Ser Arg Leu Ser Gly Pro Val
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic Construct

<400> SEQUENCE: 135

Gln Ser Tyr Asn Asn Ser Leu Arg Gly Ser Val
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Construct

<400> SEQUENCE: 136

Gln Ser Tyr Asp Ser Ser Leu Gly Gly Ser Val
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic Construct

<400> SEQUENCE: 137

Gln Ser Tyr Asp Ser Ser Leu Ser Ser Ser Val
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic Construct

<400> SEQUENCE: 138

Gln Ser Tyr Asp Ser Arg Leu Gly Ala Val
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Construct

<400> SEQUENCE: 139

```
Gln Ser Tyr Asp Ser Ser Leu Ser Gly Gly Val
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Construct

<400> SEQUENCE: 140

Gln Ser Tyr Asp Ser Ser Leu Asn Gly Val Val
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Construct

<400> SEQUENCE: 141

Gln Ser Tyr Asp Ser Ser Leu Ser Gly Ser Val
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic Construct

<400> SEQUENCE: 142

Gln Ser Tyr Asp Ser Ser Leu Arg Val Ser Ser Val
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic Construct

<400> SEQUENCE: 143

Gln Ser Tyr Asp Ser Ser Leu Ser Gly Ser Gly Val
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic Construct

<400> SEQUENCE: 144

Gln Ser Tyr Asp Ser Arg Leu Gly Val Val
1               5                   10

<210> SEQ ID NO 145
<211> LENGTH: 26
<212> TYPE: PRT
<213> ORGANISM: Artificial Sequence
<220> FEATURE:
<223> OTHER INFORMATION: Synthetic Construct

<400> SEQUENCE: 145
```

Asp Ile Gln Met Thr Gln Ser Pro Ser Ser Val Ser Ala Ser Val Gly
1               5                   10                  15

Asp Arg Val Thr Ile Asn Cys Arg Ala Ser
            20                  25

<210> SEQ ID NO 146
<211> LENGTH: 25
<212> TYPE: PRT
<213> ORGANISM: Artificial Sequence
<220> FEATURE:
<223> OTHER INFORMATION: Synthetic Construct

<400> SEQUENCE: 146

Gln Leu Val Leu Thr Gln Pro Pro Ser Val Ser Gly Ala Pro Gly Gln
1               5                   10                  15

Thr Val Thr Ile Ser Cys Thr Gly Ser
            20                  25

<210> SEQ ID NO 147
<211> LENGTH: 25
<212> TYPE: PRT
<213> ORGANISM: Artificial Sequence
<220> FEATURE:
<223> OTHER INFORMATION: Synthetic Construct

<400> SEQUENCE: 147

Gln Phe Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 148
<211> LENGTH: 25
<212> TYPE: PRT
<213> ORGANISM: Artificial Sequence
<220> FEATURE:
<223> OTHER INFORMATION: Synthetic Construct

<400> SEQUENCE: 148

Gln Leu Val Leu Thr Gln Pro Pro Ser Val Ser Gly Ala Pro Gly Gln
1               5                   10                  15

Ser Val Ser Ile Ser Cys Ile Gly Ser
            20                  25

<210> SEQ ID NO 149
<211> LENGTH: 25
<212> TYPE: PRT
<213> ORGANISM: Artificial Sequence
<220> FEATURE:
<223> OTHER INFORMATION: Synthetic Construct

<400> SEQUENCE: 149

Gln Leu Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 150
<211> LENGTH: 26
<212> TYPE: PRT
<213> ORGANISM: Artificial Sequence
<220> FEATURE:
<223> OTHER INFORMATION: Synthetic Construct

<400> SEQUENCE: 150

```
Asp Ile Val Met Thr Gln Thr Pro Leu Ser Leu Ser Val Thr Pro Gly
1               5                   10                  15

Gln Pro Ala Ser Ile Ser Cys Lys Ser Ser
            20                  25
```

<210> SEQ ID NO 151
<211> LENGTH: 25
<212> TYPE: PRT
<213> ORGANISM: Artificial Sequence
<220> FEATURE:
<223> OTHER INFORMATION: Synthetic Construct

<400> SEQUENCE: 151

```
Gln Leu Val Leu Thr Gln Pro Pro Ser Val Ser Ala Pro Pro Gly Gln
1               5                   10                  15

Lys Val Thr Ile Ser Cys Ser Gly Ser
            20                  25
```

<210> SEQ ID NO 152
<211> LENGTH: 26
<212> TYPE: PRT
<213> ORGANISM: Artificial Sequence
<220> FEATURE:
<223> OTHER INFORMATION: Synthetic Construct

<400> SEQUENCE: 152

```
Asp Ile Val Met Thr Gln Thr Pro Leu Ser Leu Pro Val Thr Pro Gly
1               5                   10                  15

Glu Pro Ala Ser Ile Ser Cys Arg Ser Ser
            20                  25
```

<210> SEQ ID NO 153
<211> LENGTH: 26
<212> TYPE: PRT
<213> ORGANISM: Artificial Sequence
<220> FEATURE:
<223> OTHER INFORMATION: Synthetic Construct

<400> SEQUENCE: 153

```
Asp Ile Gln Met Thr Gln Ser Pro Ala Thr Leu Ser Leu Ser Pro Gly
1               5                   10                  15

Glu Arg Ala Thr Leu Ser Cys Thr Ala Ser
            20                  25
```

<210> SEQ ID NO 154
<211> LENGTH: 25
<212> TYPE: PRT
<213> ORGANISM: Artificial Sequence
<220> FEATURE:
<223> OTHER INFORMATION: Synthetic Construct

<400> SEQUENCE: 154

```
Gln Leu Val Leu Thr Gln Pro Thr Ser Val Ser Gly Ala Pro Gly Gln
1               5                   10                  15

Arg Val Ile Ile Ser Cys Thr Gly Ser
            20                  25
```

<210> SEQ ID NO 155
<211> LENGTH: 25
<212> TYPE: PRT
<213> ORGANISM: Artificial Sequence
<220> FEATURE:
<223> OTHER INFORMATION: Synthetic Construct

```
<400> SEQUENCE: 155

Gln Leu Val Leu Thr Gln Pro Pro Ser Val Ser Gly Ala Pro Gly Gln
1               5                   10                  15

Arg Val Ile Ile Ser Cys Thr Gly Ser
            20                  25

<210> SEQ ID NO 156
<211> LENGTH: 25
<212> TYPE: PRT
<213> ORGANISM: Artificial Sequence
<220> FEATURE:
<223> OTHER INFORMATION: Synthetic Construct

<400> SEQUENCE: 156

Gln Leu Val Leu Thr Gln Pro Pro Ser Val Ser Gly Ala Pro Gly Gln
1               5                   10                  15

Arg Val Thr Ile Ser Cys Thr Gly Thr
            20                  25

<210> SEQ ID NO 157
<211> LENGTH: 25
<212> TYPE: PRT
<213> ORGANISM: Artificial Sequence
<220> FEATURE:
<223> OTHER INFORMATION: Synthetic Construct

<400> SEQUENCE: 157

Gln Leu Val Leu Thr Gln Pro Pro Ser Val Ser Gly Ala Pro Gly Gln
1               5                   10                  15

Arg Val Thr Ile Ser Cys Thr Gly Thr
            20                  25

<210> SEQ ID NO 158
<211> LENGTH: 25
<212> TYPE: PRT
<213> ORGANISM: Artificial Sequence
<220> FEATURE:
<223> OTHER INFORMATION: Synthetic Construct

<400> SEQUENCE: 158

Gln Leu Val Leu Thr Gln Pro Pro Ser Val Ser Gly Ala Pro Gly Gln
1               5                   10                  15

Ser Val Thr Ile Ser Cys Thr Gly Ser
            20                  25

<210> SEQ ID NO 159
<211> LENGTH: 25
<212> TYPE: PRT
<213> ORGANISM: Artificial Sequence
<220> FEATURE:
<223> OTHER INFORMATION: Synthetic Construct

<400> SEQUENCE: 159

Gln Leu Val Leu Thr Gln Pro Pro Ser Val Ser Gly Ala Pro Gly Gln
1               5                   10                  15

Arg Val Thr Ile Ser Cys Thr Gly Gly
            20                  25

<210> SEQ ID NO 160
<211> LENGTH: 25
<212> TYPE: PRT
<213> ORGANISM: Artificial Sequence
<220> FEATURE:
<223> OTHER INFORMATION: Synthetic Construct
```

```
<400> SEQUENCE: 160

Gln Leu Val Leu Thr Gln Pro Ser Ser Val Ser Gly Ala Pro Gly Gln
1               5                   10                  15

Arg Val Thr Ile Ser Cys Thr Gly Ser
            20                  25

<210> SEQ ID NO 161
<211> LENGTH: 25
<212> TYPE: PRT
<213> ORGANISM: Artificial Sequence
<220> FEATURE:
<223> OTHER INFORMATION: Synthetic Construct

<400> SEQUENCE: 161

Gln Leu Val Leu Thr Gln Pro Pro Ser Val Ser Gly Ala Pro Gly Gln
1               5                   10                  15

Gly Val Thr Ile Ser Cys Thr Gly Asp
            20                  25

<210> SEQ ID NO 162
<211> LENGTH: 25
<212> TYPE: PRT
<213> ORGANISM: Artificial Sequence
<220> FEATURE:
<223> OTHER INFORMATION: Synthetic Construct

<400> SEQUENCE: 162

Gln Leu Val Leu Thr Gln Pro Pro Ser Val Ser Ala Ala Pro Gly Gln
1               5                   10                  15

Lys Val Thr Phe Ser Cys Thr Gly Ser
            20                  25

<210> SEQ ID NO 163
<211> LENGTH: 25
<212> TYPE: PRT
<213> ORGANISM: Artificial Sequence
<220> FEATURE:
<223> OTHER INFORMATION: Synthetic Construct

<400> SEQUENCE: 163

Gln Leu Val Leu Thr Gln Pro Pro Ser Val Ser Ala Ala Pro Gly Gln
1               5                   10                  15

Thr Val Thr Ile Ser Cys Thr Gly Ser
            20                  25

<210> SEQ ID NO 164
<211> LENGTH: 17
<212> TYPE: PRT
<213> ORGANISM: Artificial Sequence
<220> FEATURE:
<223> OTHER INFORMATION: Synthetic Construct

<400> SEQUENCE: 164

Leu Ala Trp Tyr Gln Gln Lys Pro Gly Lys Ala Pro Lys Leu Leu Ile
1               5                   10                  15

Tyr

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 165

Val His Trp Tyr Gln Gln Leu Pro Gly Thr Ala Pro Lys Leu Leu Ile
1               5                   10                  15

Tyr

<210> SEQ ID NO 166
<211> LENGTH: 17
<212> TYPE: PRT
<213> ORGANISM: Artificial Sequence
<220> FEATURE:
<223> OTHER INFORMATION: Synthetic Construct

<400> SEQUENCE: 166

Val His Trp Tyr Gln Gln Leu Pro Gly Lys Ala Pro Lys Val Val Ile
1               5                   10                  15

Tyr

<210> SEQ ID NO 167
<211> LENGTH: 17
<212> TYPE: PRT
<213> ORGANISM: Artificial Sequence
<220> FEATURE:
<223> OTHER INFORMATION: Synthetic Construct

<400> SEQUENCE: 167

Val His Trp Tyr Gln Gln Ile Pro Gly Glu Ala Pro Lys Leu Leu Ile
1               5                   10                  15

Tyr

<210> SEQ ID NO 168
<211> LENGTH: 17
<212> TYPE: PRT
<213> ORGANISM: Artificial Sequence
<220> FEATURE:
<223> OTHER INFORMATION: Synthetic Construct

<400> SEQUENCE: 168

Val His Trp Tyr Gln Gln Ile Pro Gly Thr Ala Pro Lys Val Leu Ile
1               5                   10                  15

Tyr

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct

<400> SEQUENCE: 169

Leu Tyr Trp Tyr Leu Gln Lys Pro Gly Gln Ser Pro Gln Leu Leu Ile
1               5                   10                  15

Tyr

<210> SEQ ID NO 170
<211> LENGTH: 17
<212> TYPE: PRT
<213> ORGANISM: Artificial Sequence
<220> FEATURE:
<223> OTHER INFORMATION: Synthetic Construct

<400> SEQUENCE: 170

Val Ser Trp Tyr Gln Gln Leu Pro Gly Thr Ala Pro Lys Leu Leu Ile

```
1               5                   10                  15

Tyr

<210> SEQ ID NO 171
<211> LENGTH: 17
<212> TYPE: PRT
<213> ORGANISM: Artificial Sequence
<220> FEATURE:
<223> OTHER INFORMATION: Synthetic Construct

<400> SEQUENCE: 171

Leu Asp Trp Tyr Leu Gln Lys Pro Gly Gln Ser Pro Gln Leu Leu Ile
1               5                   10                  15

Tyr

<210> SEQ ID NO 172
<211> LENGTH: 17
<212> TYPE: PRT
<213> ORGANISM: Artificial Sequence
<220> FEATURE:
<223> OTHER INFORMATION: Synthetic Construct

<400> SEQUENCE: 172

Leu Ala Trp Tyr Gln Gln Lys Pro Gly Gln Ala Pro Arg Leu Leu Ile
1               5                   10                  15

Tyr

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct

<400> SEQUENCE: 173

Val His Trp Tyr Gln Ser Leu Pro Gly Thr Val Pro Lys Leu Leu Ile
1               5                   10                  15

Ser

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Val His Trp Tyr Gln His Arg Pro Gly Lys Ala Pro Gln Leu Leu Ile
1               5                   10                  15

Tyr

<210> SEQ ID NO 175
<211> LENGTH: 17
<212> TYPE: PRT
<213> ORGANISM: Artificial Sequence
<220> FEATURE:
<223> OTHER INFORMATION: Synthetic Construct

<400> SEQUENCE: 175

Val His Trp Tyr Gln Gln Leu Pro Gly Thr Ala Pro Lys Leu Leu Ile
1               5                   10                  15

His
```

```
<210> SEQ ID NO 176
<211> LENGTH: 17
<212> TYPE: PRT
<213> ORGANISM: Artificial Sequence
<220> FEATURE:
<223> OTHER INFORMATION: Synthetic Construct

<400> SEQUENCE: 176

Val His Trp Tyr Gln Gln Val Pro Gly Thr Ala Pro Lys Leu Leu Ile
1               5                   10                  15

Tyr

<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Val His Trp Tyr Gln Gln Leu Pro Gly Thr Ala Pro Lys Leu Leu Ile
1               5                   10                  15

Val

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Val His Trp Tyr Gln Gln Leu Pro Gly Ala Ala Pro Lys Leu Leu Ile
1               5                   10                  15

His

<210> SEQ ID NO 179
<211> LENGTH: 17
<212> TYPE: PRT
<213> ORGANISM: Artificial Sequence
<220> FEATURE:
<223> OTHER INFORMATION: Synthetic Construct

<400> SEQUENCE: 179

Val Gln Trp Tyr Gln Gln Ile Pro Gly Thr Ala Pro Lys Leu Leu Ile
1               5                   10                  15

Tyr

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Val His Trp Tyr Gln Gln Leu Pro Gly Thr Ala Pro Lys Leu Ile Ile
1               5                   10                  15

Tyr

<210> SEQ ID NO 181
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 181

Val His Trp Tyr Gln Gln Leu Pro Gly Thr Ala Pro Lys Leu Leu
1               5                   10                  15

Phe

<210> SEQ ID NO 182
<211> LENGTH: 17
<212> TYPE: PRT
<213> ORGANISM: Artificial Sequence
<220> FEATURE:
<223> OTHER INFORMATION: Synthetic Construct

<400> SEQUENCE: 182

Val His Trp Tyr Gln Gln Phe Pro Gly Thr Ala Pro Lys Leu Leu Ile
1               5                   10                  15

Tyr

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Val His Trp Tyr Gln His Leu Pro Gly Ala Ala Pro Arg Leu Leu Ile
1               5                   10                  15

Tyr

<210> SEQ ID NO 184
<211> LENGTH: 17
<212> TYPE: PRT
<213> ORGANISM: Artificial Sequence
<220> FEATURE:
<223> OTHER INFORMATION: Synthetic Construct

<400> SEQUENCE: 184

Val His Trp Tyr Gln Gln Leu Pro Gly Ala Ala Pro Lys Leu Leu Ile
1               5                   10                  15

Tyr

<210> SEQ ID NO 185
<211> LENGTH: 36
<212> TYPE: PRT
<213> ORGANISM: Artificial Sequence
<220> FEATURE:
<223> OTHER INFORMATION: Synthetic Construct

<400> SEQUENCE: 185

Asn Leu Gln Ser Gly Val Pro Ser Arg Phe Ser Gly Ser Gly Ser Gly
1               5                   10                  15

Thr Asp Phe Thr Leu Thr Ile Ala Ser Leu Gln Pro Glu Asp Phe Ala
            20                  25                  30

Thr Tyr Tyr Cys
        35

<210> SEQ ID NO 186
<211> LENGTH: 36
<212> TYPE: PRT
```

<213> ORGANISM: Artificial Sequence
<220> FEATURE:
<223> OTHER INFORMATION: Synthetic Construct

<400> SEQUENCE: 186

Asn Arg Pro Ser Gly Val Pro Asp Arg Phe Ser Gly Ser Lys Ser Gly
1               5                   10                  15

Ala Leu Ala Ser Leu Ala Ile Thr Gly Leu Gln Ala Glu Asp Gly Ala
            20                  25                  30

Asp Tyr His Cys
        35

<210> SEQ ID NO 187
<211> LENGTH: 36
<212> TYPE: PRT
<213> ORGANISM: Artificial Sequence
<220> FEATURE:
<223> OTHER INFORMATION: Synthetic Construct

<400> SEQUENCE: 187

Asn Arg Pro Ser Gly Val Leu Asp Arg Phe Ser Ala Ser Lys Ser Ala
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 188
<211> LENGTH: 36
<212> TYPE: PRT
<213> ORGANISM: Artificial Sequence
<220> FEATURE:
<223> OTHER INFORMATION: Synthetic Construct

<400> SEQUENCE: 188

Asn Arg Pro Ser Gly Val Pro Asp Arg Phe Ser Gly Ser Arg Ser Gly
1               5                   10                  15

Ser Ser Ala Ser Leu Asp Ile Thr Gly Leu Gln Ala Asp Asp Glu Ala
            20                  25                  30

Tyr Tyr Tyr Cys
        35

<210> SEQ ID NO 189
<211> LENGTH: 36
<212> TYPE: PRT
<213> ORGANISM: Artificial Sequence
<220> FEATURE:
<223> OTHER INFORMATION: Synthetic Construct

<400> SEQUENCE: 189

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 190
<211> LENGTH: 36
<212> TYPE: PRT
<213> ORGANISM: Artificial Sequence
<220> FEATURE:
<223> OTHER INFORMATION: Synthetic Construct

<400> SEQUENCE: 190

Asp Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 191
<211> LENGTH: 36
<212> TYPE: PRT
<213> ORGANISM: Artificial Sequence
<220> FEATURE:
<223> OTHER INFORMATION: Synthetic Construct

<400> SEQUENCE: 191

Lys Arg Phe Ser Gly Val Pro Asp Arg Phe Ser Gly Ser Gly Ser Gly
1               5                   10                  15

Thr Asp Phe Thr Leu Lys Ile Gly Arg Val Glu Ala Glu Asp Val Gly
            20                  25                  30

Val Tyr Tyr Cys
        35

<210> SEQ ID NO 192
<211> LENGTH: 36
<212> TYPE: PRT
<213> ORGANISM: Artificial Sequence
<220> FEATURE:
<223> OTHER INFORMATION: Synthetic Construct

<400> SEQUENCE: 192

Glu Arg Pro Ser Gly Ile Pro Asp Arg Phe Ser Ala Ser Lys Ser Gly
1               5                   10                  15

Thr Ser Ala Thr Leu Gly Ile Ser Gly Leu Gln Thr Gly Asp Glu Ala
            20                  25                  30

Asp Tyr Tyr Cys
        35

<210> SEQ ID NO 193
<211> LENGTH: 36
<212> TYPE: PRT
<213> ORGANISM: Artificial Sequence
<220> FEATURE:
<223> OTHER INFORMATION: Synthetic Construct

<400> SEQUENCE: 193

Phe Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Ser Gly
            20                  25                  30

Ile Tyr Tyr Cys
        35

<210> SEQ ID NO 194
<211> LENGTH: 36
<212> TYPE: PRT
<213> ORGANISM: Artificial Sequence
<220> FEATURE:
<223> OTHER INFORMATION: Synthetic Construct

<400> SEQUENCE: 194

```
Asn Arg Ala Thr Gly Ile Pro Ala Arg Phe Ser Gly Ser Gly Ser Gly
1               5                   10                  15

Thr Ala Phe Thr Leu Thr Ile Ser Ser Leu Glu Pro Glu Asp Phe Ala
            20                  25                  30

Val Tyr Phe Cys
        35

<210> SEQ ID NO 195
<211> LENGTH: 36
<212> TYPE: PRT
<213> ORGANISM: Artificial Sequence
<220> FEATURE:
<223> OTHER INFORMATION: Synthetic Construct

<400> SEQUENCE: 195

Asn Arg Pro Ser Gly Val Pro Asp Arg Phe Ser Gly Ser Lys Ser Gly
1               5                   10                  15

Thr Ala Ala Ser Leu Ala Ile Thr Gly Leu Gln Ala Glu Asp Glu Ala
            20                  25                  30

Asp Tyr Tyr Cys
        35

<210> SEQ ID NO 196
<211> LENGTH: 36
<212> TYPE: PRT
<213> ORGANISM: Artificial Sequence
<220> FEATURE:
<223> OTHER INFORMATION: Synthetic Construct

<400> SEQUENCE: 196

Asn Arg Pro Pro Gly Val Pro Asp Arg Phe Ser Gly Ser Lys Ser Gly
1               5                   10                  15

Thr Ser Ala Ser Leu Ala Ile Ser Leu Gln Ser Glu Asp Glu Ala
            20                  25                  30

Asp Tyr Tyr Cys
        35

<210> SEQ ID NO 197
<211> LENGTH: 36
<212> TYPE: PRT
<213> ORGANISM: Artificial Sequence
<220> FEATURE:
<223> OTHER INFORMATION: Synthetic Construct

<400> SEQUENCE: 197

Asn Arg Pro Ser Gly Ile Pro Asp Arg Phe Ser Gly Ser Lys Ser Gly
1               5                   10                  15

Thr Ser Ala Ser Leu Ala Ile Thr Gly Leu Gln Pro Glu Asp Glu Ala
            20                  25                  30

Asp Tyr Tyr Cys
        35

<210> SEQ ID NO 198
<211> LENGTH: 36
<212> TYPE: PRT
<213> ORGANISM: Artificial Sequence
<220> FEATURE:
<223> OTHER INFORMATION: Synthetic Construct

<400> SEQUENCE: 198

Ile Arg Pro Ser Gly Val Pro Asp Arg Phe Ser Gly Ser Arg Ser Gly
1               5                   10                  15
```

-continued

Thr Ser Ala Ser Leu Ala Ile Thr Gly Leu Gln Ala Asp Glu Ala
            20                  25                  30

Asn Tyr Phe Cys
        35

<210> SEQ ID NO 199
<211> LENGTH: 36
<212> TYPE: PRT
<213> ORGANISM: Artificial Sequence
<220> FEATURE:
<223> OTHER INFORMATION: Synthetic Construct

<400> SEQUENCE: 199

His Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Thr
            20                  25                  30

Asp Tyr Tyr Cys
        35

<210> SEQ ID NO 200
<211> LENGTH: 36
<212> TYPE: PRT
<213> ORGANISM: Artificial Sequence
<220> FEATURE:
<223> OTHER INFORMATION: Synthetic Construct

<400> SEQUENCE: 200

Asn Arg Pro Ser Gly Val Pro Asp Arg Phe Ser Gly Ser Lys Ser Asp
1               5                   10                  15

Thr Ser Ala Ser Leu Ala Leu Thr Gly Leu Gln Ala Glu Asp Glu Ala
            20                  25                  30

Thr Tyr Tyr Cys
        35

<210> SEQ ID NO 201
<211> LENGTH: 36
<212> TYPE: PRT
<213> ORGANISM: Artificial Sequence
<220> FEATURE:
<223> OTHER INFORMATION: Synthetic Construct

<400> SEQUENCE: 201

Asp Arg Pro Ser Gly Val Pro Asp Arg Phe Ser Gly Ser Lys Ser Gly
1               5                   10                  15

Thr Ser Ala Ser Leu Ala Ile Thr Gly Leu Gln Pro Glu Asp Glu Ala
            20                  25                  30

Asp Tyr Tyr Cys
        35

<210> SEQ ID NO 202
<211> LENGTH: 36
<212> TYPE: PRT
<213> ORGANISM: Artificial Sequence
<220> FEATURE:
<223> OTHER INFORMATION: Synthetic Construct

<400> SEQUENCE: 202

Asn Arg Pro Ser Gly Val Pro Asp Arg Phe Ser Gly Ser Lys Ser Gly
1               5                   10                  15

Thr Leu Ala Ser Leu Ala Ile Thr Gly Leu Gln Ser Glu Asp Glu Ala
            20                  25                  30

Asp Tyr Tyr Cys
        35

<210> SEQ ID NO 203
<211> LENGTH: 36
<212> TYPE: PRT
<213> ORGANISM: Artificial Sequence
<220> FEATURE:
<223> OTHER INFORMATION: Synthetic Construct

<400> SEQUENCE: 203

Lys Arg Ala Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Gly Ala
            20                  25                  30

Asp Tyr Tyr Cys
        35

<210> SEQ ID NO 204
<211> LENGTH: 36
<212> TYPE: PRT
<213> ORGANISM: Artificial Sequence
<220> FEATURE:
<223> OTHER INFORMATION: Synthetic Construct

<400> SEQUENCE: 204

Asn Arg Pro Ser Gly Val Pro Gly Arg Phe Ser Gly Ser Lys Ser Gly
1               5                   10                  15

Ser Ser Ala Ser Leu Ala Ile Thr Gly Leu Gln Ser Asp Asp Glu Ala
            20                  25                  30

Asp Tyr Tyr Cys
        35

<210> SEQ ID NO 205
<211> LENGTH: 36
<212> TYPE: PRT
<213> ORGANISM: Artificial Sequence
<220> FEATURE:
<223> OTHER INFORMATION: Synthetic Construct

<400> SEQUENCE: 205

Asn Arg Pro Ser Gly Val Pro Asp Arg Phe Ser Val Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 206
<211> LENGTH: 36
<212> TYPE: PRT
<213> ORGANISM: Artificial Sequence
<220> FEATURE:
<223> OTHER INFORMATION: Synthetic Construct

<400> SEQUENCE: 206

Asn Arg Pro Leu Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 207
<211> LENGTH: 36
<212> TYPE: PRT
<213> ORGANISM: Artificial Sequence
<220> FEATURE:
<223> OTHER INFORMATION: Synthetic Construct

<400> SEQUENCE: 207

Asn Arg Pro Ser Gly Val Pro Asp Arg Phe Ser Gly Ser Lys Ser Gly
1               5                   10                  15

Ile Ser Ala Ser Leu Ala Ile Thr Gly Leu Gln Ala Glu Asp Glu Ala
            20                  25                  30

Asp Tyr Tyr Cys
        35

<210> SEQ ID NO 208
<211> LENGTH: 36
<212> TYPE: PRT
<213> ORGANISM: Artificial Sequence
<220> FEATURE:
<223> OTHER INFORMATION: Synthetic Construct

<400> SEQUENCE: 208

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Thr Asp Asp Glu Ala
            20                  25                  30

Asp Tyr Phe Cys
        35

<210> SEQ ID NO 209
<211> LENGTH: 36
<212> TYPE: PRT
<213> ORGANISM: Artificial Sequence
<220> FEATURE:
<223> OTHER INFORMATION: Synthetic Construct

<400> SEQUENCE: 209

Asn Arg Pro Ser Gly Val Pro Asp Arg Phe Ser Gly Ser Lys Ser Gly
1               5                   10                  15

Thr Ser Ala Ser Leu Ala Ile Ala Gly Leu Gln Ser Asp Asp Glu Ala
            20                  25                  30

Asp Tyr Tyr Cys
        35

<210> SEQ ID NO 210
<211> LENGTH: 36
<212> TYPE: PRT
<213> ORGANISM: Artificial Sequence
<220> FEATURE:
<223> OTHER INFORMATION: Synthetic Construct

<400> SEQUENCE: 210

Asn Arg Pro Ser Gly Val Pro Ala Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 211
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 211

Phe Gly Gly Gly Thr Lys Val Glu Ile Lys
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic Construct

<400> SEQUENCE: 212

Phe Gly Thr Gly Thr Lys Val Thr Val Leu
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic Construct

<400> SEQUENCE: 213

Phe Gly Gly Gly Thr Lys Leu Thr Val Leu
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic Construct

<400> SEQUENCE: 214

Phe Gly Gln Gly Thr Lys Leu Glu Ile Lys
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic Construct

<400> SEQUENCE: 215

Phe Gly Gly Gly Thr Lys Val Asp Ile Lys
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Ile Gly Thr Gly Thr Lys Val Thr Val Leu
1               5                   10

<210> SEQ ID NO 217
<211> LENGTH: 107
<212> TYPE: PRT
```

<213> ORGANISM: Artificial Sequence
<220> FEATURE:
<223> OTHER INFORMATION: Synthetic Construct

<400> SEQUENCE: 217

```
Asp Ile Gln Met Thr Gln Ser Pro Ser Ser Val Ser Ala Ser Val Gly
1               5                   10                  15

Asp Arg Val Thr Ile Asn Cys Arg Ala Ser Gln Gly Ile Arg Thr Trp
                20                  25                  30

Leu Ala Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
50                      55                  60

Ser Gly Ser Gly Thr Asp Phe Thr Leu Thr Ile Ala Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 218
<211> LENGTH: 112
<212> TYPE: PRT
<213> ORGANISM: Artificial Sequence
<220> FEATURE:
<223> OTHER INFORMATION: Synthetic Construct

<400> SEQUENCE: 218

```
Gln Leu Val Leu Thr Gln Pro Pro Ser Val Ser Gly Ala Pro Gly Gln
1               5                   10                  15

Thr Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Asn Asn Arg Pro Ser Gly Val Pro Asp Arg Phe
50                      55                  60

Ser Gly Ser Lys Ser Gly Ala Leu Ala Ser Leu Ala Ile Thr Gly Leu
65                  70                  75                  80

Gln Ala Glu Asp Gly Ala Asp Tyr His Cys Gln Ser Tyr Asp Asn Ser
                85                  90                  95

Leu Ser Ala His Ala Val Phe Gly Thr Gly Thr Lys Val Thr Val Leu
            100                 105                 110
```

<210> SEQ ID NO 219
<211> LENGTH: 111
<212> TYPE: PRT
<213> ORGANISM: Artificial Sequence
<220> FEATURE:
<223> OTHER INFORMATION: Synthetic Construct

<400> SEQUENCE: 219

```
Gln Phe Val Leu Thr Gln Pro Pro Ser Val Ser Gly Ala Pro Gly Gln
1               5                   10                  15

Arg Val Thr Ile Ser Cys Thr Gly Ser Ser Thr Asn Ile Gly Ala Gly
                20                  25                  30

Tyr Asp Val His Trp Tyr Gln Gln Leu Pro Gly Lys Ala Pro Lys Val
            35                  40                  45

Val Ile Tyr Gly Asn Ser Asn Arg Pro Ser Gly Val Leu Asp Arg Phe
50                      55                  60
```

```
Ser Ala Ser Lys Ser Ala Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Thr Gly Thr Lys Val Thr Val Leu
            100                 105                 110

<210> SEQ ID NO 220
<211> LENGTH: 113
<212> TYPE: PRT
<213> ORGANISM: Artificial Sequence
<220> FEATURE:
<223> OTHER INFORMATION: Synthetic Construct

<400> SEQUENCE: 220

Gln Leu Val Leu Thr Gln Pro Pro Ser Val Ser Gly Ala Pro Gly Gln
 1               5                  10                  15

Ser Val Ser Ile Ser Cys Ile Gly Ser Asn Ser Asn Ile Gly Thr Pro
                20                  25                  30

Tyr Asp Val His Trp Tyr Gln Gln Ile Pro Gly Glu Ala Pro Lys Leu
             35                  40                  45

Leu Ile Tyr Gly Ser Thr Asn Arg Pro Ser Gly Val Pro Asp Arg Phe
 50                  55                  60

Ser Gly Ser Arg Ser Gly Ser Ser Ala Ser Leu Asp Ile Thr Gly Leu
 65                  70                  75                  80

Gln Ala Asp Asp Glu Ala Tyr Tyr Tyr Cys Gln Ser Tyr Asp Arg Ser
                 85                  90                  95

Leu Gly Val Ser Asp Val Val Phe Gly Gly Thr Lys Leu Thr Val
            100                 105                 110

Leu

<210> SEQ ID NO 221
<211> LENGTH: 113
<212> TYPE: PRT
<213> ORGANISM: Artificial Sequence
<220> FEATURE:
<223> OTHER INFORMATION: Synthetic Construct

<400> SEQUENCE: 221

Gln Leu Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
             35                  40                  45

Leu Ile Tyr Ser Asn Arg Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Pro Asn Tyr Val Phe Gly Thr Gly Thr Lys Val Thr Val
            100                 105                 110

Leu

<210> SEQ ID NO 222
<211> LENGTH: 111
```

<212> TYPE: PRT
<213> ORGANISM: Artificial Sequence
<220> FEATURE:
<223> OTHER INFORMATION: Synthetic Construct

<400> SEQUENCE: 222

Gln Leu Val Leu Thr Gln Pro Pro Ser Val Ser Gly Ala Pro Gly Gln
1               5                   10                  15

Arg Val Thr Ile Ser Cys Thr Gly Ser Asn Ser Asp Ile Gly Ala Gly
            20                  25                  30

His Asp Val His Trp Tyr Gln Gln Ile Pro Gly Thr Ala Pro Lys Val
        35                  40                  45

Leu Ile Tyr Gly Asn Thr Asp Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu
            100                 105                 110

<210> SEQ ID NO 223
<211> LENGTH: 112
<212> TYPE: PRT
<213> ORGANISM: Artificial Sequence
<220> FEATURE:
<223> OTHER INFORMATION: Synthetic Construct

<400> SEQUENCE: 223

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Gly Arg Val Glu Ala Glu Asp Val Gly Val Tyr Tyr Cys Met Gln Gly
                85                  90                  95

Leu His Leu Pro Tyr Thr Phe Gly Gln Gly Thr Lys Leu Glu Ile Lys
            100                 105                 110

<210> SEQ ID NO 224
<211> LENGTH: 110
<212> TYPE: PRT
<213> ORGANISM: Artificial Sequence
<220> FEATURE:
<223> OTHER INFORMATION: Synthetic Construct

<400> SEQUENCE: 224

Gln Leu Val Leu Thr Gln Pro Pro Ser Val Ser Ala Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser

```
                 50                  55                  60

Ala Ser Lys Ser Gly Thr Ser Ala Thr Leu Gly Ile Ser Leu Gln
 65                  70                  75                  80

Thr Gly Asp Glu Ala Asp Tyr Tyr Cys Gly Thr Trp Asp Ser Ser Leu
                     85                  90                  95

Ser Ala Gly Val Phe Gly Gly Gly Thr Lys Leu Thr Val Leu
                100                 105                 110

<210> SEQ ID NO 225
<211> LENGTH: 113
<212> TYPE: PRT
<213> ORGANISM: Artificial Sequence
<220> FEATURE:
<223> OTHER INFORMATION: Synthetic Construct

<400> SEQUENCE: 225

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Met Ile Ser Phe Arg Ala Ser Gly Val
        50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Ser Gly Ile Tyr Tyr Cys Met Gln
                 85                  90                  95

Arg Val Glu Phe Pro Tyr Thr Phe Gly Gln Gly Thr Lys Leu Glu Ile
            100                 105                 110

Lys

<210> SEQ ID NO 226
<211> LENGTH: 107
<212> TYPE: PRT
<213> ORGANISM: Artificial Sequence
<220> FEATURE:
<223> OTHER INFORMATION: Synthetic Construct

<400> SEQUENCE: 226

Asp Ile Gln Met Thr Gln Ser Pro Ala Thr Leu Ser Leu Ser Pro Gly
 1               5                  10                  15

Glu Arg Ala Thr Leu Ser Cys Thr Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Tyr Asp Ser Ser Asn Arg Ala Thr Gly Ile Pro Ala Arg Phe Ser Gly
        50                  55                  60

Ser Gly Ser Gly Thr Ala Phe Thr Leu Thr Ile Ser Ser Leu Glu Pro
 65                  70                  75                  80

Glu Asp Phe Ala Val Tyr Phe Cys Gln Gln Arg Gly Gln Trp Pro Leu
                 85                  90                  95

Thr Phe Gly Gly Gly Thr Lys Val Asp Ile Lys
            100                 105

<210> SEQ ID NO 227
<211> LENGTH: 112
<212> TYPE: PRT
```

```
<213> ORGANISM: Artificial Sequence
<220> FEATURE:
<223> OTHER INFORMATION: Synthetic Construct

<400> SEQUENCE: 227

Gln Leu Val Leu Thr Gln Pro Thr Ser Val Ser Gly Ala Pro Gly Gln
1               5                   10                  15

Arg Val Ile Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ala Ala Ser Leu Ala Ile Thr Gly Leu
65                  70                  75                  80

Gln Ala Glu Asp Glu Ala Asp Tyr Tyr Cys Gln Ser Phe Asp Arg Ser
                85                  90                  95

Arg Ser Gly Ser Asn Val Phe Gly Thr Gly Thr Lys Val Thr Val Leu
            100                 105                 110

<210> SEQ ID NO 228
<211> LENGTH: 111
<212> TYPE: PRT
<213> ORGANISM: Artificial Sequence
<220> FEATURE:
<223> OTHER INFORMATION: Synthetic Construct

<400> SEQUENCE: 228

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Ser Leu Pro Gly Thr Val Pro Lys Leu
        35                  40                  45

Leu Ile Ser Gly Asn Ser Asn Arg Pro Pro Gly Val Pro Asp Arg Phe
    50                  55                  60

Ser Gly Ser Lys Ser Gly Thr Ser Ala Ser Leu Ala Ile Thr Ser Leu
65                  70                  75                  80

Gln Ser Glu Asp Glu Ala Asp Tyr Tyr Cys His Ser Tyr Asp Gly Ser
                85                  90                  95

Leu Ser Glu Gly Val Phe Gly Thr Gly Thr Lys Val Thr Val Leu
            100                 105                 110

<210> SEQ ID NO 229
<211> LENGTH: 110
<212> TYPE: PRT
<213> ORGANISM: Artificial Sequence
<220> FEATURE:
<223> OTHER INFORMATION: Synthetic Construct

<400> SEQUENCE: 229

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln His Arg Pro Gly Lys Ala Pro Gln Leu
        35                  40                  45

Leu Ile Tyr Gly Asp Asn Asn Arg Pro Ser Gly Ile Pro Asp Arg Phe
    50                  55                  60
```

Ser Gly Ser Lys Ser Gly Thr Ser Ala Ser Leu Ala Ile Thr Gly Leu
65                  70                  75                  80

Gln Pro Glu Asp Glu Ala Asp Tyr Tyr Cys Gln Ser Phe Asp Ser Arg
                85                  90                  95

Leu Gly Val Val Phe Gly Gly Gly Thr Lys Leu Thr Val Leu
            100                 105                 110

<210> SEQ ID NO 230
<211> LENGTH: 111
<212> TYPE: PRT
<213> ORGANISM: Artificial Sequence
<220> FEATURE:
<223> OTHER INFORMATION: Synthetic Construct

<400> SEQUENCE: 230

Gln Leu Val Leu Thr Gln Pro Pro Ser Val Ser Gly Ala Pro Gly Gln
1               5                   10                  15

Arg Val Thr Ile Ser Cys Thr Gly Ser Asn Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile His Gly Asn Asn Ile Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Asp Asp Glu Ala Asn Tyr Phe Cys Gln Ser Tyr Asp Asn Ser
                85                  90                  95

Leu Arg Gly Ser Val Phe Gly Thr Gly Thr Lys Val Thr Val Leu
            100                 105                 110

<210> SEQ ID NO 231
<211> LENGTH: 111
<212> TYPE: PRT
<213> ORGANISM: Artificial Sequence
<220> FEATURE:
<223> OTHER INFORMATION: Synthetic Construct

<400> SEQUENCE: 231

Gln Leu Val Leu Thr Gln Pro Pro Ser Val Ser Gly Ala Pro Gly Gln
1               5                   10                  15

Arg Val Ile Ile Ser Cys Thr Gly Ser Ser Ser Asn Ile Gly Ala Gly
            20                  25                  30

Tyr Asp Val His Trp Tyr Gln Gln Val Pro Gly Thr Ala Pro Lys Leu
        35                  40                  45

Leu Ile Tyr Gly Asn Asn His Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Asn Arg
                85                  90                  95

Leu Ser Gly Ser Leu Phe Gly Gly Gly Thr Lys Leu Thr Val Leu
            100                 105                 110

<210> SEQ ID NO 232
<211> LENGTH: 111
<212> TYPE: PRT
<213> ORGANISM: Artificial Sequence
<220> FEATURE:
<223> OTHER INFORMATION: Synthetic Construct

<400> SEQUENCE: 232

Gln Leu Val Leu Thr Gln Pro Pro Ser Val Ser Gly Ala Pro Gly Gln
1               5                   10                  15

Arg Val Thr Ile Ser Cys Thr Gly Thr Asn Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Val Thr Asn His Asn Arg Pro Ser Gly Val Pro Asp Arg Phe
    50                  55                  60

Ser Gly Ser Lys Ser Asp Thr Ser Ala Ser Leu Ala Leu Thr Gly Leu
65                  70                  75                  80

Gln Ala Glu Asp Glu Ala Thr Tyr Tyr Cys Gln Ser Tyr Asp Ser Arg
                85                  90                  95

Leu Ser Gly Pro Val Phe Gly Thr Gly Thr Lys Val Thr Val Leu
            100                 105                 110

<210> SEQ ID NO 233
<211> LENGTH: 111
<212> TYPE: PRT
<213> ORGANISM: Artificial Sequence
<220> FEATURE:
<223> OTHER INFORMATION: Synthetic Construct

<400> SEQUENCE: 233

Gln Leu Val Leu Thr Gln Pro Pro Ser Val Ser Gly Ala Pro Gly Gln
1               5                   10                  15

Ser Val Thr Ile Ser Cys Thr Gly Ser Asn Ser Asp Ile Gly Ala Gly
            20                  25                  30

His Asp Val His Trp Tyr Gln Gln Leu Pro Gly Ala Ala Pro Lys Leu
        35                  40                  45

Leu Ile His Gly Asp Arg Asp Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Pro Glu Asp Glu Ala Asp Tyr Tyr Cys Gln Ser Tyr Asn Asn Ser
                85                  90                  95

Leu Arg Gly Ser Val Phe Gly Thr Gly Thr Lys Val Thr Val Leu
            100                 105                 110

<210> SEQ ID NO 234
<211> LENGTH: 111
<212> TYPE: PRT
<213> ORGANISM: Artificial Sequence
<220> FEATURE:
<223> OTHER INFORMATION: Synthetic Construct

<400> SEQUENCE: 234

Gln Leu Val Leu Thr Gln Pro Pro Ser Val Ser Gly Ala Pro Gly Gln
1               5                   10                  15

Arg Val Thr Ile Ser Cys Thr Gly Thr Asn Ser Asn Ile Gly Ala Gly
            20                  25                  30

His Asp Val Gln Trp Tyr Gln Gln Ile Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Leu Ala Ser Leu Ala Ile Thr Gly Leu
65                  70                  75                  80

Gln Ser Glu Asp Glu Ala Asp Tyr Tyr Cys His Ser Tyr Asp Gly Ser
                85                  90                  95

Leu Ser Glu Gly Val Phe Gly Thr Gly Thr Lys Val Thr Val Leu
            100                 105                 110

<210> SEQ ID NO 235
<211> LENGTH: 112
<212> TYPE: PRT
<213> ORGANISM: Artificial Sequence
<220> FEATURE:
<223> OTHER INFORMATION: Synthetic Construct

<400> SEQUENCE: 235

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Ile Ile Tyr Gly Asp Thr Lys Arg Ala Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Gly Ala Asp Tyr Tyr Cys Gln Ser Tyr Asp Asn Ser
                85                  90                  95

Leu Ser Ala His Ala Val Phe Gly Thr Gly Thr Lys Val Thr Val Leu
            100                 105                 110

<210> SEQ ID NO 236
<211> LENGTH: 111
<212> TYPE: PRT
<213> ORGANISM: Artificial Sequence
<220> FEATURE:
<223> OTHER INFORMATION: Synthetic Construct

<400> SEQUENCE: 236

Gln Leu Val Leu Thr Gln Pro Pro Ser Val Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Leu Phe Gly Asn Thr Asn Arg Pro Ser Gly Val Pro Gly Arg Phe
    50                  55                  60

Ser Gly Ser Lys Ser Gly Ser Ser Ala Ser Leu Ala Ile Thr Gly Leu
65                  70                  75                  80

Gln Ser Asp Asp Glu Ala Asp Tyr Tyr Cys Gln Ser Tyr Asp Ser Ser
                85                  90                  95

Leu Gly Gly Ser Val Ile Gly Thr Gly Thr Lys Val Thr Val Leu
            100                 105                 110

<210> SEQ ID NO 237
<211> LENGTH: 111
<212> TYPE: PRT
<213> ORGANISM: Artificial Sequence
<220> FEATURE:
<223> OTHER INFORMATION: Synthetic Construct

<400> SEQUENCE: 237

Gln Leu Val Leu Thr Gln Pro Ser Ser Val Ser Gly Ala Pro Gly Gln
1               5                   10                  15

Arg Val Thr Ile Ser Cys Thr Gly Ser Ser Asn Leu Gly Ala Pro
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Val Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ser Ser Val Phe Gly Gly Gly Thr Lys Leu Thr Val Leu
            100                 105                 110

<210> SEQ ID NO 238
<211> LENGTH: 110
<212> TYPE: PRT
<213> ORGANISM: Artificial Sequence
<220> FEATURE:
<223> OTHER INFORMATION: Synthetic Construct

<400> SEQUENCE: 238

Gln Leu Val Leu Thr Gln Pro Ser Val Ser Gly Ala Pro Gly Gln
1               5                   10                  15

Gly Val Thr Ile Ser Cys Thr Gly Asp Ser Ser Asn Ile Gly Ala Gly
            20                  25                  30

Tyr Asp Val His Trp Tyr Gln Gln Phe Pro Gly Thr Ala Pro Lys Leu
        35                  40                  45

Leu Ile Tyr Glu Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Gly Ala Val Phe Gly Gly Gly Thr Lys Leu Thr Val Leu
            100                 105                 110

<210> SEQ ID NO 239
<211> LENGTH: 111
<212> TYPE: PRT
<213> ORGANISM: Artificial Sequence
<220> FEATURE:
<223> OTHER INFORMATION: Synthetic Construct

<400> SEQUENCE: 239

Gln Leu Val Leu Thr Gln Pro Ser Val Ser Ala Ala Pro Gly Gln
1               5                   10                  15

Lys Val Thr Phe Ser Cys Thr Gly Ser Ser Ser Asn Ile Gly Ala Gly
            20                  25                  30

Tyr Asp Val His Trp Tyr Gln His Leu Pro Gly Ala Ala Pro Arg Leu
        35                  40                  45

Leu Ile Tyr Ala Asn Thr Asn Arg Pro Leu Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Arg
                85                  90                  95

```
Leu Ser Gly Ser Leu Phe Gly Gly Gly Thr Lys Leu Thr Val Leu
            100                 105                 110
```

<210> SEQ ID NO 240
<211> LENGTH: 111
<212> TYPE: PRT
<213> ORGANISM: Artificial Sequence
<220> FEATURE:
<223> OTHER INFORMATION: Synthetic Construct

<400> SEQUENCE: 240

```
Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Ala Ala Pro Lys Leu
        35                  40                  45

Leu Ile Tyr Gly Asp Ile Asn Arg Pro Ser Gly Val Pro Asp Arg Phe
    50                  55                  60

Ser Gly Ser Lys Ser Gly Ile Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu
            100                 105                 110
```

<210> SEQ ID NO 241
<211> LENGTH: 111
<212> TYPE: PRT
<213> ORGANISM: Artificial Sequence
<220> FEATURE:
<223> OTHER INFORMATION: Synthetic Construct

<400> SEQUENCE: 241

```
Gln Phe Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Ser Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Asn Gly Val Val Phe Gly Gly Gly Thr Lys Leu Thr Val Leu
            100                 105                 110
```

<210> SEQ ID NO 242
<211> LENGTH: 111
<212> TYPE: PRT
<213> ORGANISM: Artificial Sequence
<220> FEATURE:
<223> OTHER INFORMATION: Synthetic Construct

<400> SEQUENCE: 242

```
Gln Leu Val Leu Thr Gln Pro Pro Ser Val Ser Gly Ala Pro Gly Gln
1               5                   10                  15
```

Arg Val Thr Ile Ser Cys Thr Gly Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Leu Phe Gly Asn Thr Asn Arg Pro Ser Gly Val Pro Gly Arg Phe
50                  55                  60

Ser Gly Ser Lys Ser Gly Ser Ser Ala Ser Leu Ala Ile Thr Gly Leu
65                  70                  75                  80

Gln Ser Asp Asp Glu Ala Asp Tyr Tyr Cys Gln Ser Tyr Asp Ser Ser
                85                  90                  95

Leu Ser Gly Ser Val Phe Gly Thr Gly Thr Lys Val Thr Val Leu
            100                 105                 110

<210> SEQ ID NO 243
<211> LENGTH: 111
<212> TYPE: PRT
<213> ORGANISM: Artificial Sequence
<220> FEATURE:
<223> OTHER INFORMATION: Synthetic Construct

<400> SEQUENCE: 243

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu
            100                 105                 110

<210> SEQ ID NO 244
<211> LENGTH: 112
<212> TYPE: PRT
<213> ORGANISM: Artificial Sequence
<220> FEATURE:
<223> OTHER INFORMATION: Synthetic Construct

<400> SEQUENCE: 244

Gln Leu Val Leu Thr Gln Pro Pro Ser Val Ser Ala Ala Pro Gly Gln
1               5                   10                  15

Thr Val Thr Ile Ser Cys Thr Gly Ser Ser Ser Asn Ile Gly Ala Gly
            20                  25                  30

Tyr Asp Val His Trp Tyr Gln Gln Phe Pro Gly Thr Ala Pro Lys Leu
            35                  40                  45

Leu Ile Tyr Gly Asn Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Thr Asp Asp Glu Ala Asp Tyr Phe Cys Gln Ser Tyr Asp Ser Ser
                85                  90                  95

Leu Arg Val Ser Ser Val Phe Gly Thr Gly Thr Lys Val Thr Val Leu
            100                 105                 110

<210> SEQ ID NO 245
<211> LENGTH: 112
<212> TYPE: PRT
<213> ORGANISM: Artificial Sequence
<220> FEATURE:
<223> OTHER INFORMATION: Synthetic Construct

<400> SEQUENCE: 245

Gln Leu Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Thr Gly Thr Lys Val Thr Val Leu
            100                 105                 110

<210> SEQ ID NO 246
<211> LENGTH: 111
<212> TYPE: PRT
<213> ORGANISM: Artificial Sequence
<220> FEATURE:
<223> OTHER INFORMATION: Synthetic Construct

<400> SEQUENCE: 246

Gln Phe Val Leu Thr Gln Pro Pro Ser Val Ser Gly Ala Pro Gly Gln
1               5                   10                  15

Arg Val Thr Ile Ser Cys Thr Gly Ser Arg Ser Asn Phe Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Ala Gly Leu
65                  70                  75                  80

Gln Ser Asp Asp Glu Ala Asp Tyr Tyr Cys Gln Ser Tyr Asp Ser Ser
                85                  90                  95

Leu Ser Gly Ser Val Phe Gly Thr Gly Thr Lys Val Thr Val Leu
            100                 105                 110

<210> SEQ ID NO 247
<211> LENGTH: 110
<212> TYPE: PRT
<213> ORGANISM: Artificial Sequence
<220> FEATURE:
<223> OTHER INFORMATION: Synthetic Construct

<400> SEQUENCE: 247

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Val Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Asn Arg Pro Ser Gly Val Pro Ala Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Arg
            85                  90                  95

Leu Gly Val Val Phe Gly Gly Gly Thr Lys Leu Thr Val Leu
            100                 105                 110

<210> SEQ ID NO 248
<211> LENGTH: 232
<212> TYPE: PRT
<213> ORGANISM: Artificial Sequence
<220> FEATURE:
<223> OTHER INFORMATION: Synthetic Construct

<400> SEQUENCE: 248

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 249
<211> LENGTH: 233
<212> TYPE: PRT
<213> ORGANISM: Artificial Sequence
<220> FEATURE:
<223> OTHER INFORMATION: Synthetic Construct

<400> SEQUENCE: 249

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230

<210> SEQ ID NO 250
<211> LENGTH: 23
<212> TYPE: DNA
<213> ORGANISM: Artificial Sequence
<220> FEATURE:
<223> OTHER INFORMATION: Synthetic Construct

<400> SEQUENCE: 250
ccaggatggt tcttagactc ccc                                                 23

<210> SEQ ID NO 251
<211> LENGTH: 20
<212> TYPE: DNA
<213> ORGANISM: Artificial Sequence
<220> FEATURE:
<223> OTHER INFORMATION: Synthetic Construct

<400> SEQUENCE: 251
caccagggtt tggaactggc                                                     20

<210> SEQ ID NO 252
<211> LENGTH: 114
<212> TYPE: PRT
<213> ORGANISM: Artificial Sequence
<220> FEATURE:
<223> OTHER INFORMATION: Synthetic construct

<400> SEQUENCE: 252
```

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala

<210> SEQ ID NO 253
<211> LENGTH: 114
<212> TYPE: PRT
<213> ORGANISM: Artificial Sequence
<220> FEATURE:
<223> OTHER INFORMATION: Synthetic construct

<400> SEQUENCE: 253

Phe Ser Ile Thr Ala Ser Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala

<210> SEQ ID NO 254
<211> LENGTH: 114
<212> TYPE: PRT
<213> ORGANISM: Artificial Sequence
<220> FEATURE:
<223> OTHER INFORMATION: Synthetic construct

<400> SEQUENCE: 254

Phe Thr Val Thr Val Pro Lys Asp Leu Tyr Val Val Glu Tyr Gly Ser
1               5                   10                  15

Asn Val Thr Leu Glu Cys Arg Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 255
<211> LENGTH: 114
<212> TYPE: PRT
<213> ORGANISM: Artificial Sequence
<220> FEATURE:
<223> OTHER INFORMATION: Synthetic construct

<400> SEQUENCE: 255

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Arg Glu Leu Asn Leu
            20                  25                  30

Leu Val Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 256
<211> LENGTH: 114
<212> TYPE: PRT
<213> ORGANISM: Artificial Sequence
<220> FEATURE:
<223> OTHER INFORMATION: Synthetic construct

<400> SEQUENCE: 256

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Gly Lys Glu Asp Glu Gln Val Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 257

<211> LENGTH: 114
<212> TYPE: PRT
<213> ORGANISM: Artificial Sequence
<220> FEATURE:
<223> OTHER INFORMATION: Synthetic construct

<400> SEQUENCE: 257

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val Asn Gly Lys Glu Asp Pro Asn Pro Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 258
<211> LENGTH: 114
<212> TYPE: PRT
<213> ORGANISM: Artificial Sequence
<220> FEATURE:
<223> OTHER INFORMATION: Synthetic construct

<400> SEQUENCE: 258

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Asn Phe His
    50                  55                  60

Gly Arg Ala Gln Leu Pro Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala

<210> SEQ ID NO 259
<211> LENGTH: 114
<212> TYPE: PRT
<213> ORGANISM: Artificial Sequence
<220> FEATURE:
<223> OTHER INFORMATION: Synthetic construct

<400> SEQUENCE: 259

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

-continued

```
Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Leu Lys Gly Lys Ala Val
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala

<210> SEQ ID NO 260
<211> LENGTH: 114
<212> TYPE: PRT
<213> ORGANISM: Artificial Sequence
<220> FEATURE:
<223> OTHER INFORMATION: Synthetic construct

<400> SEQUENCE: 260

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Val Lys Val
                100                 105                 110

Asn Ala
```

ANTIBODY TO PROGRAMMED DEATH-LIGAND 1 (PD-L1) AND USE THEREOF

CROSS-REFERENCE TO RELATED APPLICATIONS

This application is a U.S. national phase under 35 U.S.C. § 371 of International Patent Application No. PCT/KR17/08495 filed Aug. 7, 2017, which in turn claims the priorities under 35 U.S.C. § 119 of Korean Patent Application No. 10-2016-0100211 filed Aug. 5, 2016 and Korean Patent Application 10-2017-0099673 filed Aug. 7, 2017. The disclosures of such International Patent Application No. PCT/KR17/08495, Korean Patent Application No. 10-2016-0100211, and Korean Patent Application 10-2017-0099673 are hereby incorporated herein by reference in their respective entireties, for all purposes.

TECHNICAL FIELD

The present disclosure relates to an antibody to human programmed cell death-ligand 1 (PD-L1) or an antigen-binding fragment thereof, a nucleic acid encoding the same, a vector including the nucleic acid, a cell transformed with the vector, a method for producing the antibody or an antigen-binding fragment thereof, and a composition for preventing or treating cancer or infectious diseases containing the same.

BACKGROUND ART

The immune response of antigen-specific T-lymphocyte cells is a process that is very complicated and regulated delicately. First of all, activation of T-lymphocytes begins when the T-cell antigen receptor (TCR) present on the surface of T-lymphocytes recognizes the major histocompatibility complex (MHC) of the antigen-presenting cells (APCs), and, in humans, antigens bound to class II molecules of HLA (human leucocyte antigen). In this case, for sufficient activation of T-lymphocytes, in addition to the recognition of antigens, co-stimulatory signals are required, which are obtained, when CD80, CD40 and the like expressed in antigen presenting cells simultaneously bind to CD28, CD40L and the like, which are ligands present on the surface of T-lymphocyte cells. As a result, the secretion of cytokines is activated. Activation of T-lymphocytes is not achieved in the absence of transfer of co-stimulatory signals, although the antigen is recognized by the binding of TCR-MHC/epitope.

However, co-inhibitory signals are also activated so that activated T-lymphocytes become inactive after a period of time. This can prevent tissue damage and the like due to excessive immune stimulation. There are a variety of co-inhibitory signals and representatively, cytotoxic T lymphocyte antigen (CTLA)-4 and programmed death-1 (PD-1) of T lymphocytes and antigen-presenting cell ligands corresponding thereto are involved in CD80 and CD86, and PD-L1 (programmed death-ligand 1). CTLA-4 functions to inactivate naive or memory T-lymphocytes by binding to the ligands, CD80 and CD86. PD-1 functions to regulate functions of T-lymphocytes in peripheral tissues through PD-L1 and PD-L2.

The immune function of the human body is to recognize antigens and, at the same time, to regulate the overall T lymphocyte functions through regulation of these co-stimulatory and co-inhibitory signals. This regulatory mechanism is called "immune checkpoint". The human immune function is to detect tumor-specific neo-antigens expressed by variations such as mutations occurring in tumor cells and thereby to eliminate tumor cells or virus infection sources.

On the other hand, in order to avoid such immune attacks, some tumor cells inhibit immune functions by altering the tumor microenvironments or perform immune escape by T-cell immunity tolerance or immuno-editing.

One of immune escape strategies is to inhibit the functions of tumor-specific T lymphocytes through changes in immune checkpoint functions. That is, the attack of tumor-specific T-lymphocyte cells is avoided by activating such an inhibitory immune checkpoint in tumor cells. In this regard, activities and effects of inhibited tumor-specific T-lymphocyte cells are improved by inhibiting functions thereof using monoclonal antibodies against PD-1 or a ligand thereof, PD-L1, so that antitumor effects can be obtained.

Under these technical backgrounds, the present inventors have made efforts to develop antibodies specifically binding to PD-L1. As a result, the present inventors have developed anti-PD-L1 antibodies that bind with a high affinity to PD-L1, and have found that the anti-PD-L1 antibody can serve as the desired immune anticancer agent or therapeutic agent for infectious diseases by inhibiting the formation of the PD-1/PD-L1 complex, thus completing the present disclosure.

DISCLOSURE

Technical Problem

Therefore, it is one object of the present disclosure to provide a novel antibody to PD-L1 or an antigen-binding fragment thereof.

It is another object of the present disclosure to provide a nucleic acid encoding the antibody or an antigen-binding fragment thereof.

It is another object of the present disclosure to provide a vector including the nucleic acid, a cell transformed with the vector, and a method for preparing the same.

It is another object of the present disclosure to provide a composition for preventing or treating cancer or infectious diseases containing the antibody or antigen-binding fragment thereof.

Technical Solution

In accordance with the present disclosure, the above and other objects can be accomplished by the provision of an antibody binding to PD-L1 or an antigen-binding fragment thereof including a heavy chain variable region including a heavy chain CDR1 including a sequence having a sequence identity of 90% or higher with a sequence selected from the group consisting of sequences as set forth in synthetic construct: 1 to 7, a heavy chain CDR2 including a sequence having a sequence identity of 90% or higher with a sequence selected from the group consisting of sequences as set forth in SEQ ID NOS: 8 to 15, and a heavy chain CDR3 including a sequence having a sequence identity of 90% or higher with a sequence selected from the group consisting of sequences as set forth in SEQ ID NOS: 16 to 25, and a light chain variable region including a light chain CDR1 including a sequence having a sequence identity of 90% or higher with a sequence selected from the group consisting of sequences as set forth in SEQ ID NOS: 88 to 102, a light chain CDR2 including a sequence having a sequence identity of 90% or higher with a sequence selected from the group consisting of sequences as set forth in SEQ ID NOS: 103 to 119, and a light chain CDR3 including a sequence having a sequence identity of 90% or higher with a sequence selected from the group consisting of sequences as set forth in SEQ ID NOS: 120 to 144.

In accordance with another aspect of the present disclosure, provided is a nucleic acid encoding the antibody or an antigen-binding fragment.

In accordance with another aspect of the present disclosure, provided is an expression vector including the nucleic acid.

In accordance with another aspect of the present disclosure, provided is a cell transformed with the expression vector.

In accordance with another aspect of the present disclosure, provided is a method for producing the antibody or an antigen-binding fragment thereof, including (a) culturing the cell, and (b) recovering the antibody or an antigen-binding fragment thereof from the cultured cell.

In accordance with another aspect of the present disclosure, provided is a composition for preventing or treating cancer or infectious diseases containing, as an active ingredient, the antibody or an antigen-binding fragment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present disclosure will be more clearly understood from the following detailed description taken in conjunction with the accompanying drawings, in which:

FIG. 1 is a schematic diagram showing a PD-L1 expression vector;

FIGS. 2A-2D show a result of PD-L1 protein purification;

FIG. 2A shows a result of protein identification with regard to PD-L1-hFc on 10% SDS-PAGE gel under RE (reducing) and NR (non-reducing) conditions;

FIG. 2B shows a result of G-3000 SWXL SEC-HPLC at a flow rate of 1 ml/min and using PBS as a development solvent;

FIG. 2C shows a result of protein identification with regard to PD-L1-mFc on 10% SDS-PAGE gel under RE (reducing) and NR (non-reducing) conditions;

FIG. 2D shows a result of G-3000 SWXL SEC-HPLC at a flow rate of 1 ml/min and using PBS as a development solvent;

FIG. 3 shows a result of an increase in binding capacity to a PD-L1 antigen depending on the number of times of panning;

FIG. 4 shows a result of ELISA to measure a binding capacity of monophages having a high binding capacity only to PD-L1-His;

FIG. 5 shows a result of SDS-PAGE analysis to identify selected PD-L1 antibodies;

FIG. 6 shows a result of evaluation of in vitro efficacy of PD-L1 antibodies;

FIG. 7 shows a result of concentration-dependent in vitro efficacy evaluation of PD-L1 antibodies;

FIG. 8 shows a result of measurement of binding capacities of PD-L1 antibodies in PD-L1 over-expressed cells;

FIG. 9 shows a result of measurement of kinetics between PD-L1-hFc and PD-L1-16E12;

FIG. 10 shows a result of screening of optimization monoclones;

FIG. 11 shows a result of evaluation of in vitro efficacy, with regard to the PD-L1 antibody according to the present disclosure;

FIG. 12 shows a result of concentration-dependent in vitro efficacy evaluation of the PD-L1 antibody according to the present disclosure;

FIG. 13 shows a result of measurement of binding capacities of antibodies in PD-L1 over-expressed cells;

FIG. 14 shows a result of identification using enzyme immunoadsorption with regard to an inhibitory activity of selected antibodies to prevent formation of a PD-1/PD-L2 complex;

FIG. 15 shows a result of measurement of kinetics between PD-L1-hFc and PD-L1-16E12-4F5;

FIG. 16 shows a result of measurement of binding of PD-L1 mutant proteins and monoclonal antibodies, wherein:

hPD-L1 has the sequence FTVTVPKDLYVVEYGSNM-TIECKFPVEKQLDLAALIVYWEMEDKNIIQFVH-GEEDLKVQ HSSYRQRARLLKDQLSLGNAALQ ITDVKLQDAGVYRCMISYGGADYKRITVKVNA (SEQ ID NO: 252);

M1 has the sequence FSITASKDLYVVEYGSNM-TIECKFPVEKQLDLAALIVYWEMEDKNIIQFVH-GEEDLKVQH SSYRQRARLLKDQLSLGNAALQIT DVKLQDAGVYRCMISYGGADYKRITVKVNA (SEQ ID NO: 253);

M2 has the sequence FTVTVPKDLYVVEYGSNVTLE-CRFPVEKQLDLAALIVYWEMEDKNIIQFVH-GEEDLKVQ HSSYRQRARLLKDQLSLGNAALQI TDVKLQDAGVYRCMISYGGADYKRITVKVNA (SEQ ID NO: 254);

M3 has the sequence FTVTVPKDLYVVEYGSNM-TIECKFPVERELNLLVLIVYWEMEDKNIIQFVH-GEEDLKVQ HSSYRQRARLLKDQLSLGNAALQIT DVKLQDAGVYRCMISYGGADYKRITVKVNA (SEQ ID NO: 255);

M4 has the sequence FTVTVPKDLYVVEYGSNM-TIECKFPVEKQLDLAALIVYWGKEDEQVIQFVH-GEEDLKVQ HSSYRQRARLLKDQLSLGNAALQIT DVKLQDAGVYRCMISYGGADYKRITVKVNA (SEQ ID NO: 256);

M5 has the sequence FTVTVPKDLYVVEYGSNM-TIECKFPVEKQLDLAALIVY-WEMEDKNIIQFVNGKEDPNPQ HSSYRQRARLLKDQLSLG-NAALQITDVKLQDAGVYRCMISYGGA-DYKRITVKVNA (SEQ ID NO: 257);

M6 has the sequence FTVTVPKDLYVVEYGSNM-TIECKFPVEKQLDLAALIVYWEMEDKNIIQFVH-GEEDLKVQ HSNFHGRAQLPKDQLSLGNAALQI TDVKLQDAGVYRCMISYGGADYKRITVKVNA (SEQ ID NO: 258);

M7 has the sequence FTVTVPKDLYVVEYGSNM-TIECKFPVEKQLDLAALIVYWEMEDKNIIQFVH-GEEDLKVQ HSSYRQRARLLKDQLLKGKAVLQIT DVKLQDAGVYRCMISYGGADYKRITVKVNA (SEQ ID NO: 259); and M8 has the sequence FTVTVPKDLYVVEYGSNM-TIECKFPVEKQLDLAALIVYWEMEDKNIIQFVH-GEEDLKVQ HSSYRQRARLLKDQLSLGNAAL QITDVKLQDAGVYCCIISYGGADYKRITVKVNA (SEQ ID NO: 260);

FIG. 17 shows a result of identification with regard to an increase in activity by PD-L1 monoclonal antibodies during heterogeneous MLR (mixed lymphocyte reaction);

FIG. 18 shows a result of evaluation of efficacy of selected PD-L1 monoclonal antibody in a syngeneic cancer animal model; and FIG. 19 shows a result of identification regarding binding between the anti-PD-L1 antibody according to the present disclosure, and PD-L2.

DETAILED DESCRIPTION OF THE INVENTION

Unless defined otherwise, all technical and scientific terms used herein have the same meaning as those appreciated by those skilled in the field to which the present disclosure pertains. In general, nomenclature used herein is well-known in the art and is ordinarily used.

In one aspect, the present disclosure is directed to an antibody binding to PD-L1 or an antigen-binding fragment thereof including: a heavy chain variable region including a heavy chain CDR1 including a sequence having a sequence identity of 90% or higher with a sequence selected from the group consisting of sequences as set forth in SEQ ID NOS: 1 to 7, a heavy chain CDR2 including a sequence having a sequence identity of 90% or higher with a sequence selected from the group consisting of sequences as set forth in SEQ ID NOS: 8 to 15, and a heavy chain CDR3 including a sequence having a sequence identity of 90% or higher with a sequence selected from the group consisting of sequences as set forth in SEQ ID NOS: 16 to 25; and a light chain variable region including a light chain CDR1 including a sequence having a sequence identity of 90% or higher with a sequence selected from the group consisting of sequences as set forth in SEQ ID NOS: 88 to 102, a light chain CDR2 including a sequence having a sequence identity of 90% or higher with a sequence selected from the group consisting of sequences as set forth in SEQ ID NOS: 103 to 119, and a light chain CDR3 including a sequence having a sequence identity of 90% or higher with a sequence selected from the group consisting of sequences as set forth in SEQ ID NOS: 120 to 144.

As used herein, the term "PD-L1" is a ligand for an immunosuppressive receptor "programmed death receptor 1 (PD-1)" that is predominantly expressed in activated T and B cells, which can negatively regulate antigen receptor signaling. The ligands (PD-L1 and PD-L2) for PD-1 may be constitutively expressed or may be derived into a number of cell types, including non-hematopoietic cell tissues and various tumor types. PD-L1 is expressed in B cells, T cells, bone marrow cells and dendritic cells (DCs), but also on non-lymphatic organs such as peripheral cells, pseudo-vascular endothelial cells and heart, lungs and the like. In contrast, PD-L2 is found only in macrophages and dendritic cells. The expression pattern of the PD-1 ligand suggests the role of PD-1 in maintaining peripheral tolerance and may contribute to the regulation of autoreactive T-cell and B-cell responses in the periphery. Both ligands are type I transmembrane receptors that contain both IgV- and IgC-like domains in the extracellular domain. Both ligands include a short cytoplasmic region having an unknown signaling motif.

A number of studies have shown that the interaction between PD-1 and ligands thereof inhibits lymphocyte proliferation in vitro and in vivo. Disruption of the PD-1/PD-L1 interaction is known to improve proliferation of T cells and production of cytokine and to block the progression of cell cycle. Blocking of the PD-1/PD-L1 interaction can lead to improved tumor-specific T-cell immunity, thus contributing to cleaning of tumor cells with the immune system. In addition, in chronic HIV infection, HIV-specific CD8+ T cells are functionally impaired, exhibiting a reduced ability to produce cytokine and effector molecules and a reduced ability to proliferate the same, and PD-1 is highly expressed in HIV-specific CD8+ T cells, which can improve T cell activity or anti-viral immune reactions by enhancing the ability to proliferate HIV-specific T cells and the ability to produce cytokines in response to HIV peptide stimuli through blocking the PD-1/PD-L1 interaction.

As used herein, the term "antibody" refers to an anti-PD-L1 antibody that specifically binds to PD-L1. The scope of the present disclosure includes not only a complete antibody specifically binding to PD-L1, but also an antigen-binding fragment of the antibody molecule.

The complete antibody refers to a structure having two full-length light chains and two full-length heavy chains, wherein each light chain is linked to the corresponding heavy chain by a disulfide bond. The heavy chain constant region has gamma ($\gamma$), mu ($\mu$), alpha ($\alpha$), delta ($\delta$) and epsilon ($\epsilon$) types and is subclassed into gamma 1 ($\gamma$1), gamma 2 ($\gamma$2), gamma ($\gamma$3), gamma 4 ($\gamma$4), alpha 1 ($\alpha$1) and alpha 2 ($\alpha$2). The constant region of the light chain has kappa ($\kappa$) and lambda ($\lambda$) types.

The antigen-binding fragment of an antibody or the antibody fragment refers to a fragment that at least has an antigen-binding capacity and includes Fab, F(ab'), F(ab')2, and Fv. Among the antibody fragments, Fab refers to a structure including a variable region of each of the heavy chain and the light chain, the constant domain of the light chain, and the first constant domain (CH1) of the heavy chain, each having one antigen-binding site. Fab' is different from Fab in that it further includes a hinge region including at least one cysteine residue at a C-terminus of the CH1 domain of the heavy chain. F(ab')2 is created by a disulfide bond between cysteine residues in the hinge region of Fab'. Fv is the minimal antibody fragment having only a heavy chain variable region and a light chain variable region, and recombinant technology for producing Fv, is disclosed in PCT International Publications such as WO88/01649, WO88/06630, WO88/07085, WO88/07086 and WO 88/09344. Two-chain Fv is a fragment wherein the variable region of the heavy chain and the variable region of the light chain are linked by a non-covalent bond, and single-chain Fv is a fragment wherein the variable region of the heavy chain and the variable region of the light chain are generally linked by a covalent bond via a peptide linker between, or are directly linked at the C-terminal, forming a dimer-like structure, like the two-chain Fv. Such antibody fragments may be obtained using proteases (e.g., Fabs can be obtained by restriction-cleaving the whole antibody with papain, and the F(ab') fragment can be obtained by restriction-cleaving the whole antibody with pepsin), and may be prepared by genetic recombination techniques.

In one embodiment, the antibody of the present disclosure is an Fv form (for example, scFv), Fab or a complete antibody form. In addition, the heavy chain constant region may be selected from the isotypes consisting of gamma ($\gamma$), mu (u), alpha ($\alpha$), delta ($\delta$) or epsilon (c). For example, the constant region may be gamma 1 (IgG1), gamma 3 (IgG3) or gamma 4 (IgG4). The light chain constant region may be kappa or lambda.

As used herein, the term "heavy chain" encompasses both a full-length heavy chain, which includes a variable domain (VH) containing an amino acid sequence having a sufficient variable region sequence for imparting a specificity to an antigen and three constant domains (CH1, CH2 and CH3), and a fragment thereof. As used herein, the term "light chain" encompasses both a full-length light chain, which includes a variable domain (VL) containing an amino acid sequence having a sufficient variable region sequence for imparting specificity to an antigen and a constant domain (CL), and a fragment thereof.

The antibody of the present disclosure includes, but is limited to, monoclonal antibodies, multispecific antibodies, human antibodies, humanized antibodies, chimeric antibodies, short chain Fvs (scFVs), short chain antibodies, Fab fragments, F(ab') fragments, disulfide-bond Fvs (sdFVs), anti-idiotypic (anti-Id) antibodies, or epitope-binding fragments of such antibodies, or the like.

The monoclonal antibody refers to the same antibody, excluding possible naturally occurring mutations where an antibody obtained from a population of substantially homogeneous antibodies, that is, each antibody constituting the population, may be present in a minor amount. Monoclonal antibodies are highly specific and are induced against a single antigenic site. In contrast to conventional (polyclonal) antibody preparations that typically contain different antibodies directed by different determinants (epitopes), each monoclonal antibody is directed by a single determinant on the antigen.

The term "epitope" means a protein determinant to which an antibody can specifically bind. An epitope is usually composed of chemically active surface molecule groups, for example, amino acids or sugar side chains, and generally has specific three dimensional structural characteristics as well as specific charge characteristics. The steric and non-steric epitopes are distinguished from each other in that binding to steric epitopes is lost in the presence of a denaturing solvent, but binding to non-steric epitopes is not lost.

The non-human (e.g., murine) antibody of the "humanized" form is a chimeric antibody containing a minimal sequence derived from non-human immunoglobulin. In most cases, the humanized antibody is a human immunoglobulin (receptor antibody) wherein a residue from the hypervariable region of a receptor is replaced with a residue from the hypervariable region of non-human species (donor antibody), such as a mouse, rat, rabbit or non-human primate having the desired specificity, affinity and ability.

The term "human antibody" means a molecule derived from human immunoglobulin, wherein all the amino acid sequences constituting the antibody including a complementarity-determining region and a structural region are composed of human immunoglobulin.

Some of the heavy chain and/or light chain is identical to or homologous with the corresponding sequence in an antibody derived from a particular species or belonging to a particular antibody class or subclass, while the remaining chain(s) include "chimeric" antibodies (immunoglobulins) which are identical to or homologous with corresponding sequences in an antibody derived from another species or belonging to another antibody class or subclass as well as fragments of such antibody exhibiting desired biological activity.

As used herein, the term "antibody variable domain" refers to the light and heavy chain regions of an antibody molecule including the amino acid sequences of a complementarity determining region (CDR; i.e., CDR1, CDR2, and CDR3) and a framework region (FR). $V_H$ refers to a variable domain of the heavy chain. $V_L$ refers to a variable domain of the light chain.

The term "complementarity determining region" (CDR; i.e., CDR1, CDR2, and CDR3) refers to an amino acid residue of the antibody variable domain, which is necessary for antigen binding. Each variable domain typically has three CDR regions identified as CDR1, CDR2, and CDR3.

In the present disclosure, the antibody binding to PD-L1 or an antigen-binding fragment thereof includes: a heavy chain variable region including a heavy chain CDR1 selected from the group consisting of SEQ ID NOS: 1 to 7, a heavy chain CDR2 selected from the group consisting of SEQ ID NOS: 8 to 15, and a heavy chain CDR3 selected from the group consisting of SEQ ID NOS: 16 to 25; and a light chain variable region including a light chain CDR1 selected from the group consisting of SEQ ID NOS: 88 to 102, a light chain CDR2 selected from the group consisting of SEQ ID NOS: 103 to 119, and a light chain CDR3 selected from the group consisting of SEQ ID NOS: 120 to 144.

Specifically, the antibody binding to PD-1 or an antigen-binding fragment thereof according to the present disclosure includes:

a heavy chain variable region including the heavy chain CDR1 of SEQ ID NO: 1, the heavy chain CDR2 of SEQ ID NO: 8 and the heavy chain CDR3 of SEQ ID NO: 16;

a heavy chain variable region including the heavy chain CDR1 of SEQ ID NO: 2, the heavy chain CDR2 of SEQ ID NO: 9 and the heavy chain CDR3 of SEQ ID NO: 17;

a heavy chain variable region including the heavy chain CDR1 of SEQ ID NO: 2, the heavy chain CDR2 of SEQ ID NO: 9 and the heavy chain CDR3 of SEQ ID NO: 18;

a heavy chain variable region including the heavy chain CDR1 of SEQ ID NO: 3, the heavy chain CDR2 of SEQ ID NO: 10 and the heavy chain CDR3 of SEQ ID NO: 19;

a heavy chain variable region including the heavy chain CDR1 of SEQ ID NO: 4, the heavy chain CDR2 of SEQ ID NO: 11 and the heavy chain CDR3 of SEQ ID NO: 20;

a heavy chain variable region including the heavy chain CDR1 of SEQ ID NO: 5, the heavy chain CDR2 of SEQ ID NO: 12 and the heavy chain CDR3 of SEQ ID NO: 21;

a heavy chain variable region including the heavy chain CDR1 of SEQ ID NO: 6, the heavy chain CDR2 of SEQ ID NO: 13 and the heavy chain CDR3 of SEQ ID NO: 22;

a heavy chain variable region including the heavy chain CDR1 of SEQ ID NO: 2, the heavy chain CDR2 of SEQ ID NO: 9 and the heavy chain CDR3 of SEQ ID NO: 23;

a heavy chain variable region including the heavy chain CDR1 of SEQ ID NO: 7, the heavy chain CDR2 of SEQ ID NO: 14 and the heavy chain CDR3 of SEQ ID NO: 24;

a heavy chain variable region including the heavy chain CDR1 of SEQ ID NO: 2, the heavy chain CDR2 of SEQ ID NO: 15 and the heavy chain CDR3 of SEQ ID NO: 25; or a heavy chain variable region including the heavy chain CDR1 of SEQ ID NO: 2, the heavy chain CDR2 of SEQ ID NO: 9 and the heavy chain CDR3 of SEQ ID NO: 17.

In addition, the antibody binding to PD-1 or an antigen-binding fragment thereof includes:

a light chain variable region including the light chain CDR1 of SEQ ID NO: 88, the light chain CDR2 of SEQ ID NO: 103 and the light chain CDR3 of SEQ ID NO: 120;

a light chain variable region including the light chain CDR1 of SEQ ID NO: 89, the light chain CDR2 of SEQ ID NO: 104 and the light chain CDR3 of SEQ ID NO: 121;

a light chain variable region including a light chain CDR1 of SEQ ID NO: 90, the light chain CDR2 of SEQ ID NO: 105 and the light chain CDR3 of SEQ ID NO: 122;

a light chain variable region including the light chain CDR1 of SEQ ID NO: 91, the light chain CDR2 of SEQ ID NO: 106 and the light chain CDR3 of SEQ ID NO: 123;

a light chain variable region including the light chain CDR1 of SEQ ID NO: 89, the light chain CDR2 of SEQ ID NO: 107 and the light chain CDR3 of SEQ ID NO: 124;

a light chain variable region including the light chain CDR1 of SEQ ID NO: 92, the light chain CDR2 of SEQ ID NO: 108 and the light chain CDR3 of SEQ ID NO: 122;

a light chain variable region including the light chain CDR1 of SEQ ID NO: 93, the light chain CDR2 of SEQ ID NO: 109 and the light chain CDR3 of SEQ ID NO: 125;

a light chain variable region including the light chain CDR1 of SEQ ID NO: 94, the light chain CDR2 of SEQ ID NO: 110 and the light chain CDR3 of SEQ ID NO: 126;

a light chain variable region including the light chain CDR1 of SEQ ID NO: 95, the light chain CDR2 of SEQ ID NO: 111 and the light chain CDR3 of SEQ ID NO: 127;

a light chain variable region including the light chain CDR1 of SEQ ID NO: 96, the light chain CDR2 of SEQ ID NO: 112 and the light chain CDR3 of SEQ ID NO: 128;

a light chain variable region including the light chain CDR1 of SEQ ID NO: 89, the light chain CDR2 of SEQ ID NO: 108 and the light chain CDR3 of SEQ ID NO: 129;

a light chain variable region including the light chain CDR1 of SEQ ID NO: 89, the light chain CDR2 of SEQ ID NO: 105 and the light chain CDR3 of SEQ ID NO: 130;

a light chain variable region including the light chain CDR1 of SEQ ID NO: 89, the light chain CDR2 of SEQ ID NO: 113 and the light chain CDR3 of SEQ ID NO: 131;

a light chain variable region including the light chain CDR1 of SEQ ID NO: 97, the light chain CDR2 of SEQ ID NO: 104 and the light chain CDR3 of SEQ ID NO: 132;

a light chain variable region including the light chain CDR1 of SEQ ID NO: 89, the light chain CDR2 of SEQ ID NO: 104 and the light chain CDR3 of SEQ ID NO: 133;

a light chain variable region including the light chain CDR1 of SEQ ID NO: 97, the light chain CDR2 of SEQ ID NO: 114 and the light chain CDR3 of SEQ ID NO: 134;

a light chain variable region including the light chain CDR1 of SEQ ID NO: 92, the light chain CDR2 of SEQ ID NO: 115 and the light chain CDR3 of SEQ ID NO: 135;

a light chain variable region including the light chain CDR1 of SEQ ID NO: 98, the light chain CDR2 of SEQ ID NO: 104 and the light chain CDR3 of SEQ ID NO: 130;

a light chain variable region including the light chain CDR1 of SEQ ID NO: 89, the light chain CDR2 of SEQ ID NO: 116 and the light chain CDR3 of SEQ ID NO: 121;

a light chain variable region including the light chain CDR1 of SEQ ID NO: 89, the light chain CDR2 of SEQ ID NO: 108 and the light chain CDR3 of SEQ ID NO: 136;

a light chain variable region including the light chain CDR1 of SEQ ID NO: 99, the light chain CDR2 of SEQ ID NO: 105 and the light chain CDR3 of SEQ ID NO: 137;

a light chain variable region including the light chain CDR1 of SEQ ID NO: 89, the light chain CDR2 of SEQ ID NO: 117 and the light chain CDR3 of SEQ ID NO: 138;

a light chain variable region including the light chain CDR1 of SEQ ID NO: 89, the light chain CDR2 of SEQ ID NO: 118 and the light chain CDR3 of SEQ ID NO: 133;

a light chain variable region including the light chain CDR1 of SEQ ID NO: 89, the light chain CDR2 of SEQ ID NO: 119 and the light chain CDR3 of SEQ ID NO: 139;

a light chain variable region including the light chain CDR1 of SEQ ID NO: 100, the light chain CDR2 of SEQ ID NO: 104 and the light chain CDR3 of SEQ ID NO: 140;

a light chain variable region including the light chain CDR1 of SEQ ID NO: 89, the light chain CDR2 of SEQ ID NO: 108 and the light chain CDR3 of SEQ ID NO: 141;

a light chain variable region including the light chain CDR1 of SEQ ID NO: 89, the light chain CDR2 of SEQ ID NO: 105 and the light chain CDR3 of SEQ ID NO: 139;

a light chain variable region including the light chain CDR1 of SEQ ID NO: 89, the light chain CDR2 of SEQ ID NO: 104 and the light chain CDR3 of SEQ ID NO: 142;

a light chain variable region including the light chain CDR1 of SEQ ID NO: 89, the light chain CDR2 of SEQ ID NO: 105 and the light chain CDR3 of SEQ ID NO: 143;

a light chain variable region including the light chain CDR1 of SEQ ID NO: 101, the light chain CDR2 of SEQ ID NO: 104 and the light chain CDR3 of SEQ ID NO: 141; or a light chain variable region including the light chain CDR1 of SEQ ID NO: 102, the light chain CDR2 of SEQ ID NO: 104 and the light chain CDR3 of SEQ ID NO: 144.

In one embodiment of the present disclosure, the antibody or an antigen-binding fragment thereof according to the present disclosure may include the following heavy chain variable regions and light chain variable regions:

a heavy chain variable region including the heavy chain CDR1 of SEQ ID NO: 1, the heavy chain CDR2 of SEQ ID NO: 8 and the heavy chain CDR3 of SEQ ID NO: 16, and a light chain variable region including the light chain CDR1 of SEQ ID NO: 88, the light chain CDR2 of SEQ ID NO: 103 and the light chain CDR3 of SEQ ID NO: 120;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 104 and the light chain CDR3 of SEQ ID NO: 121;

a heavy chain variable region including the heavy chain CDR1 of SEQ ID NO: 2, the heavy chain CDR2 of SEQ ID NO: 9 and the heavy chain CDR3 of SEQ ID NO: 18, and a light chain variable region including the light chain CDR1 of SEQ ID NO: 90, the light chain CDR2 of SEQ ID NO: 105 and the light chain CDR3 of SEQ ID NO: 122;

a heavy chain variable region including the heavy chain CDR1 of SEQ ID NO: 3, the heavy chain CDR2 of SEQ ID NO: 10 and the heavy chain CDR3 of SEQ ID NO: 19, and a light chain variable region including the light chain CDR1 of SEQ ID NO: 91, the light chain CDR2 of SEQ ID NO: 106 and the light chain CDR3 of SEQ ID NO: 123;

a heavy chain variable region including the heavy chain CDR1 of SEQ ID NO: 4, the heavy chain CDR2 of SEQ ID NO: 11 and the heavy chain CDR3 of SEQ ID NO: 20, and a light chain variable region including the light chain CDR1 of SEQ ID NO: 89, the light chain CDR2 of SEQ ID NO: 107 and the light chain CDR3 of SEQ ID NO: 124;

a heavy chain variable region including the heavy chain CDR1 of SEQ ID NO: 5, the heavy chain CDR2 of SEQ ID NO: 12 and the heavy chain CDR3 of SEQ ID NO: 21, and a light chain variable region including the light chain CDR1 of SEQ ID NO: 92, the light chain CDR2 of SEQ ID NO: 108 and the light chain CDR3 of SEQ ID NO: 122;

a heavy chain variable region including the heavy chain CDR1 of SEQ ID NO: 6, the heavy chain CDR2 of SEQ ID NO: 13 and the heavy chain CDR3 of SEQ ID NO: 22, and a light chain variable region including the light chain CDR1 of SEQ ID NO: 93, the light chain CDR2 of SEQ ID NO: 109 and the light chain CDR3 of SEQ ID NO: 125;

a heavy chain variable region including the heavy chain CDR1 of SEQ ID NO: 2, the heavy chain CDR2 of SEQ ID NO: 9 and the heavy chain CDR3 of SEQ ID NO: 23, and a light chain variable region including the light chain CDR1 of SEQ ID NO: 94, the light chain CDR2 of SEQ ID NO: 110 and the light chain CDR3 of SEQ ID NO: 126;

a heavy chain variable region including the heavy chain CDR1 of SEQ ID NO: 7, the heavy chain CDR2 of SEQ ID NO: 14 and the heavy chain CDR3 of SEQ ID NO: 24, and a light chain variable region including the light chain CDR1 of SEQ ID NO: 95, the light chain CDR2 of SEQ ID NO: 111 and the light chain CDR3 of SEQ ID NO: 127; or a heavy chain variable region including the heavy chain CDR1 of SEQ ID NO: 2, the heavy chain CDR2 of SEQ ID NO: 15 and the heavy chain CDR3 of SEQ ID NO: 25, and a light chain variable region including the light chain CDR1 of SEQ ID NO: 96, the light chain CDR2 of SEQ ID NO: 112 and the light chain CDR3 of SEQ ID NO: 128.

According to one embodiment of the present disclosure, the antibody is further screened through an optimization procedure, and the antibody or an antigen-binding fragment thereof according to the invention may include the following heavy chain variable regions and light chain variable regions:

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 108 and the light chain CDR3 of SEQ ID NO: 129;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 130;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 113 and the light chain CDR3 of SEQ ID NO: 131;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 97, the light chain CDR2 of SEQ ID NO: 104 and the light chain CDR3 of SEQ ID NO: 132;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 104 and the light chain CDR3 of SEQ ID NO: 133;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 97, the light chain CDR2 of SEQ ID NO: 114 and the light chain CDR3 of SEQ ID NO: 134;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 92, the light chain CDR2 of SEQ ID NO: 115 and the light chain CDR3 of SEQ ID NO: 135;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 98, the light chain CDR2 of SEQ ID NO: 104 and the light chain CDR3 of SEQ ID NO: 130;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 116 and the light chain CDR3 of SEQ ID NO: 121;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 108 and the light chain CDR3 of SEQ ID NO: 136;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 99, the light chain CDR2 of SEQ ID NO: 105 and the light chain CDR3 of SEQ ID NO: 137;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 117 and the light chain CDR3 of SEQ ID NO: 138;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including and the light chain CDR1 of SEQ ID NO: 89, the light chain CDR2 of SEQ ID NO: 118 and the light chain CDR3 of SEQ ID NO: 133;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 119 and the light chain CDR3 of SEQ ID NO: 139;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 100, the light chain CDR2 of SEQ ID NO: 104 and the light chain CDR3 of SEQ ID NO: 140;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 108 and the light chain CDR3 of SEQ ID NO: 141;

a heavy chain variable region including heavy chain CDR1 of SEQ ID NO: 2, heavy chain CDR2 of SEQ ID NO: 9 and heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 139;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 104 and the light chain CDR3 of SEQ ID NO: 142;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 143;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 101, the light chain CDR2 of SEQ ID NO: 104 and the light chain CDR3 of SEQ ID NO: 141; or a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 102, the light chain CDR2 of SEQ ID NO: 104 and the light chain CDR3 of SEQ ID NO: 144.

Specifically, the antibody or an antigen-binding fragment thereof according to the invention may include the following heavy chain variable regions and light chain variable regions:

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 104 and the light chain CDR3 of SEQ ID NO: 121;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 130;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 104 and the light chain CDR3 of SEQ ID NO: 133;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 108 and the light chain CDR3 of SEQ ID NO: 136;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 119 and the light chain CDR3 of SEQ ID NO: 139;

a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 139; or a heavy chain variable region including the heavy chain CDR1 of SEQ ID NO: 2, the heavy chain CDR2 of SEQ ID NO: 9 and the heavy chain CDR3 of SEQ ID NO: 17, and a light chain variable region including the light chain CDR1 of SEQ ID NO: 89, the light chain CDR2 of SEQ ID NO: 105 and the light chain CDR3 of SEQ ID NO: 143.

The "framework region" (FR) refers to a variable domain residue other than a CDR residue. Each variable domain typically has four FRs identified as FR1, FR2, FR3, and FR4.

According to one embodiment of the present disclosure, the antibody or an antigen-binding fragment thereof may include:

a heavy chain variable region FR1 selected from the group consisting of SEQ ID NOS: 26 to 34;

a heavy chain variable region FR2 selected from the group consisting of SEQ ID NOS: 35 to 41;

a heavy chain variable region FR3 selected from the group consisting of SEQ ID NOS: 42 to 49; or a heavy chain variable region FR4 selected from the group consisting of SEQ ID NOS: 50 to 54.

In addition, the antibody or an antigen-binding fragment thereof may include:

a light chain variable region FR1 selected from the group consisting of SEQ ID NOS: 145 to 163;

a light chain variable region FR2 selected from the group consisting of SEQ ID NOS: 164 to 184;

a light chain variable region FR3 selected from the group consisting of SEQ ID NOS: 185 to 210; or a light chain variable region FR4 selected from the group consisting of SEQ ID NOS: 211 to 216.

The "Fv" fragment is an antibody fragment containing complete antibody recognition and binding sites. Such region includes a dimmer, for example, scFv, that consists of one heavy chain variable domain and one light chain variable domain substantially tightly covalently connected to each other.

A "Fab" fragment contains the variable and constant domains of the light chain, and a variable and first constant domain (CH1) of the heavy chain. A F(ab')2 antibody fragment generally includes a pair of Fab fragments covalently linked via a hinge cysteine located therebetween near the carboxyl end thereof.

The "single chain Fv" or "scFv" antibody fragment includes $V_H$ and $V_L$ domains of the antibody, wherein these domains are present in a single polypeptide chain. The Fv polypeptide may further include a polypeptide linker between the $V_H$ domain and the $V_L$ domain in order for the scFv to form a desired structure for antigen binding.

The PD-L1 antibody is monovalent or divalent, and includes short or double chains. Functionally, the binding affinity of PD-L1 antibody ranges from $10^{-5}$ M to $10^{-12}$ M. For example, the binding affinity of the PD-L1 antibody is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-5}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M, or $10^{-5}$ M to $10^{-6}$ M.

The antibody binding to PD-L1 or an antigen-binding fragment thereof may include a heavy chain variable region including a sequence having a sequence identity of 90% or higher with a sequence selected from the group consisting of sequences as set forth in SEQ ID NOS: 57 to 87. The antibody binding to PD-L1 or an antigen-binding fragment thereof may include a heavy chain variable region selected from the group consisting of sequences as set forth in SEQ ID NOS: 57 to 87. In one embodiment of the present disclosure, the antibody binding to PD-L1 or an antigen-binding fragment thereof may include a heavy chain variable region of SEQ ID NO: 58, 68, 71, 76, 80, 83 or 85.

In addition, the antibody binding to PD-L1 or an antigen-binding fragment thereof may include a light chain variable region including a sequence having a sequence identity of 90% or higher with a sequence selected from the group consisting of sequences as set forth in SEQ ID NOS: 217 to 247. The antibody binding to PD-L1 or an antigen-binding fragment thereof may include a light chain variable region selected from the group consisting of sequences as set forth in SEQ ID NOS: 217 to 247. In one embodiment of the present disclosure, the antibody binding to PD-L1 or an antigen-binding fragment thereof may include a light chain variable region of SEQ ID NO: 218, 228, 231, 236, 240, 243 or 245.

In a specific embodiment according to the present disclosure, the antibody binding to PD-L1 or an antigen-binding fragment thereof may include: ???

a heavy chain variable region of SEQ ID NO: 58 and a light chain variable region of SEQ ID NO: 218;

a heavy chain variable region of SEQ ID NO: 68 and a light chain variable region of SEQ ID NO: 228;

a heavy chain variable region of SEQ ID NO: 71 and a light chain variable region of SEQ ID NO: 231;

a heavy chain variable region of SEQ ID NO: 76 and a light chain variable region of SEQ ID NO: 236;

a heavy chain variable region of SEQ ID NO: 80 and a light chain variable region of SEQ ID NO: 240;

a heavy chain variable region of SEQ ID NO: 83 and a light chain variable region of SEQ ID NO: 243; or a heavy chain variable region of SEQ ID NO: 85 and a light chain variable region of SEQ ID NO: 245.

"Phage display" is a technique for displaying a mutant polypeptide as a fusion protein with at least a part of a coat protein, for example, on the surface of the particle of a protein, for example, a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for generating and screening novel proteins that bind to specific ligands (e.g., antigens). Using the phage display technology, large libraries of protein mutants can be generated, and sequences binding with high affinity to target antigens can be rapidly classified. The nucleic acid encoding mutant polypeptides is fused with the sequence of nucleic acid encoding viral coat proteins, e.g., gene III proteins or gene VIII proteins. A monophasic phage display system, in which a nucleic acid sequence encoding protein or polypeptide is fused with a nucleic acid sequence encoding a part of the gene III protein, has been developed. In the monophasic display system, a fused gene is expressed at a low level, a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody- or antigen-binding polypeptides are prepared by a number of methods, for example, of modifying a single gene by inserting a random DNA sequence, or cloning a related gene sequence. The libraries can be screened for the expression of antibody- or antigen-binding proteins with desired characteristics.

Phage display technology has several advantages over conventional hybridomas and recombinant methods for producing antibodies with desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from non-immunized humans, germline sequences, or naive B cell Ig repertoires that have been immunized using phage display libraries can be used. Various lymphatic tissues can be used to prepare native or non-immunogenic antigen-binding libraries.

Techniques for identifying and separating high-affinity antibodies from phage display libraries are important for the separation of new therapeutic antibodies. The separation of high-affinity antibodies from the libraries can depend on the size of the libraries, the production efficiency in bacterial cells and the variety of libraries. The size of the libraries is reduced by inefficient folding of the antibody- or antigen-binding protein and inefficient production due to the presence of the stop codon. Expression in bacterial cells can be inhibited when the antibody- or antigen-binding domain is not properly folded. The expression can be improved by alternately mutating residues on the surface of the variable/constant interfaces or the selected CDR residues. The sequence of the framework region is an element to provide appropriate folding when generating antibody phage libraries in bacterial cells.

It is important to generate various libraries of antibody- or antigen-binding proteins in the separation of high-affinity antibodies. CDR3 regions have been found to often participate in antigen binding. Since the CDR3 region on the heavy chain varies considerably in terms of size, sequence and structurally dimensional morphology, various libraries can be prepared using the same.

Also, diversity can be created by randomizing the CDR regions of variable heavy and light chains using all 20 amino acids at each position. The use of all 20 amino acids results in antibody sequences with an increased diversity and an increased chance of identifying new antibodies.

The antibody or antibody fragment according to the present disclosure may include sequences of the anti-PD-L1 antibody of the present disclosure described herein as well as biological equivalents thereto so long as the antibody or antibody fragment can specifically recognize PD-L1. For example, an additional variation can be made to the amino acid sequence of the antibody in order to further improve the binding affinity and/or other biological properties of the antibody. Such a variation include, for example, deletion, insertion and/or substitution of amino acid sequence residues of the antibody. Such an amino acid variation are made, based on the relative similarity (identity) of amino acid side chain substituent, such as hydrophobicity, hydrophilicity, charge or size. Analysis of the size, shape and type of amino acid side chain substituent, demonstrates that all of arginine, lysine and histidine are positively charged residues, alanine, glycine and serine have similar sizes, and phenylalanine, tryptophan and tyrosine have similar shapes. Thus, based on these considerations, arginine, lysine and histidine; and alanine, glycine and serine; and phenylalanine, tryptophan and tyrosine are considered to be biologically functional equivalents.

When considering variations having the biologically equivalent activity, the antibody or nucleic acid encoding the same according to the present disclosure is also interpreted to include a sequence showing a substantial identity with the sequence set forth in the corresponding SEQ ID NO. The term "sequence showing a substantial identity" means a sequence that shows a identity of at least 90%, most preferably, at least 95%, 96% or more, 97% or more, 98% or more, or 99% or more, when aligning the sequence of the present disclosure so as to correspond to any other sequence as much as possible and analyzing the aligned sequence using an algorithm commonly used in the art. Alignment methods for sequence comparison are well-known in the art. The NCBI basic local alignment search tool (BLAST) is accessible from NBCI and can be used in conjunction with sequence analysis programs such as blastp, blasm, blastx, tblastn and tblastx on the Internet. BLSAT is available at www.ncbi.nlm.nih.gov/BLAST/. A method for comparing a sequence identity using this program can be found at ncbi.nlm.nih.gov/BLAST/blast_help.html.

Based on this, the antibody or an antigen-binding fragment thereof according to the present disclosure can have a sequence identity (homology) of 90%, 91%, 92%, 93%, 94%, 95%, 96%, 97%, 98%, or 99% or more. Such an identity can be determined by the comparison and/or alignment of sequences by methods known in the art. For example, the percent sequence identity of the nucleic acid or protein according to the present disclosure can be determined using a sequence comparison algorithm (i.e., BLAST or BLAST 2.0), manual alignment or visual inspection.

In another aspect, the present disclosure is directed to a nucleic acid encoding the antibody or an antigen-binding fragment thereof.

The antibody or antigen-binding fragment thereof can be recombinantly produced by isolating the nucleic acid encoding the antibody or antigen-binding fragment thereof according to the present disclosure. The nucleic acid is isolated and inserted into a replicable vector to conduct further cloning (amplification of DNA) or further expression. Based on this, in another aspect, the present disclosure is directed to a vector containing the nucleic acid.

The term "nucleic acid" is intended to encompass both DNA (gDNA and cDNA) and RNA molecules, and nucleotides, which are basic constituent units of the nucleic acid, include naturally derived nucleotides as well as analogues wherein sugar or base moieties are modified. The sequence of the nucleic acid encoding heavy and light chain variable regions of the present disclosure can be varied. Such a variation include addition, deletion, or non-conservative substitution or conservative substitution of nucleotides.

The DNA encoding the antibody can be easily separated or synthesized using conventional procedures (for example, using an oligonucleotide probe specifically binding to DNA encoding heavy and light chains of the antibody). A variety of vectors are obtainable. Vector components generally include, but are not limited to, one or more of the following components: signal sequences, replication origins, one or more marker genes, enhancer elements, promoters and transcription termination sequences.

As used herein, the term "vector" refers to a means for expressing target genes in host cells and includes: plasmid vectors; cosmid vectors; and viral vectors such as bacteriophage vectors, adenovirus vectors, retroviral vectors and adeno-associated viral vectors. The nucleic acid encoding the antibody in the vector is operatively linked to a promoter.

The term "operatively linked" means a functional linkage between a nucleic acid expression regulation sequence (e.g., promoter, signal sequence or array of transcription regulator binding site) and another nucleic acid sequence, and is regulated by transcription and/or translation of the nucleic acid sequence.

When a prokaryotic cell is used as a host, the vector generally includes a potent promoter capable of conducting transcription (such as tac promoter, lac promoter, lacUV5 promoter, lpp promoter, pLλ promoter, pRλ promoter, rac5 promoter, amp promoter, recA promoter, SP6 promoter, trp promoter, or T7 promoter), a ribosome binding site to initiate translation, and a transcription/translation termination sequence. In addition, for example, when a eukaryotic cell is used as a host, the vector includes a promoter (e.g., a metallothionein promoter, a β-actin promoter, a human hemoglobin promoter and a human muscle creatine promoter) derived from the genome of mammalian cells, or a promoter derived from animal virus such as adenovirus late promoter, vaccinia virus 7.5K promoter, SV40 promoter, cytomegalovirus (CMV) promoter, HSV tk promoter, mouse breast tumor virus (MMTV) promoter, HIV LTR promoter, Moloney virus promoter, Epstein Barr virus (EBV) promoter, and Rous sarcoma virus (RSV) promoter), and generally has a polyadenylation sequence as a transcription termination sequence.

Optionally, the vector may be fused with another sequence to facilitate purification of the antibody expressed therefrom. The sequence to be fused includes, for example, glutathione S-transferase (Pharmacia, USA), maltose-binding protein (NEB, USA), FLAG (IBI, USA), 6×His (hexahistidine; Quiagen, USA) and the like.

The vector includes antibiotic-resistant genes commonly used in the art as selectable markers and examples thereof include genes resistant to ampicillin, gentamycin, carbenicillin, chloramphenicol, streptomycin, kanamycin, geneticin, neomycin and tetracycline.

In another aspect, the present disclosure is directed to a cell transformed with the above-mentioned vector. The cell used to produce the antibody of the present disclosure may be a prokaryote, yeast or higher eukaryotic cell, but is not limited thereto.

Strains of the genus Bacillus such as Escherichia coli, Bacillus subtilis and Bacillus tuligensis, Streptomyces, Pseudomonas (for example, Pseudomonas putida), and prokaryotic host cells such as Proteus mirabilis and Staphylococcus (for example, Staphylococcus carnosus) can be used.

The interest in animal cells is the largest and examples of useful host cell lines include, but are not limited to, COS-7, BHK, CHO, CHOK1, DXB-11, DG-44, CHO/−DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

In another aspect, the present disclosure is directed to a method for producing the antibody or antigen-binding fragment thereof including: (a) culturing the cells; and (b) recovering the antibody or an antigen-binding fragment thereof from the cultured cells.

The cells can be cultured in various media. Any commercially available medium can be used as a culture medium without limitation. All other essential supplements well-known to those skilled in the art may be included in appropriate concentrations. Culture conditions such as temperature and pH have already been used with selected host cells for expression, which will be apparent to those skilled in the art.

The recovery of the antibody or antigen-binding fragment thereof can be carried out, for example, by centrifugation or ultrafiltration to remove impurities, and purification of the resulting product, for example, using affinity chromatography. Additional other purification techniques such as anion or cation exchange chromatography, hydrophobic interaction chromatography, hydroxyl apatite chromatography and the like may be used.

In another aspect, the present disclosure is directed to a composition for preventing or treating cancer containing the antibody as an active ingredient.

The present disclosure provides, for example, a composition for preventing or treating cancer or infectious disease containing: (a) a pharmaceutically effective amount of the antibody to PD-L1 or antigen-binding fragment thereof according to the invention; and (b) a pharmaceutically acceptable carrier. The present disclosure also relates to a method for preventing or treating cancer or infectious disease including administering the antibody to PD-L1 or antigen-binding fragment thereof according to the present disclosure in an effective amount required for a patient.

Since the composition uses, as an active ingredient, the anti-PD-L1 antibody or antigen-binding fragment thereof according to the present disclosure described above, repeated description thereof is omitted.

The binding of PD-L1 to PD-1 negatively regulates T cell antigen-specific responses important for tolerance and prevention of autoimmunity and immunopathology. However, excessive PD-L1/PD-1 interaction, which may be induced by chronic antigen stimulation, may cause inhibition of T cell antigen-specific responses and loss of T cells, which are characteristics of T cell depletion. T cell depletion is a condition of T cell dysfunction that may occur in chronic infections and cancers. T cell depletion is defined as a poor effector function, continuous expression of inhibitory receptors, or a transcriptional state different from functional effectors or memory T cells. Depletion interferes with the progression of infections and tumors.

As demonstrated in the following examples, the antibody or an antigen-binding fragment thereof according to the invention binds with high affinity to PD-L1 to inhibit formation of the PD-1 and PD-L1 complex, thereby being useful for the treatment of cancer inducing T cell depletion that evades anti-tumor T cell activity.

In some cases, an anti-cancer therapeutic agent other than the aforementioned antibody may be used in combination to effectively target tumor cells overexpressing PD-L1, to enhance the anti-tumor T cell activity and thereby to improve the immune response targeting tumor cells. The aforementioned antibody may be used in combination with other anti-neoplastic or immunogenic agents [for example, weaken cancer cells, tumor antigens (including recombinant proteins, peptides and carbohydrate molecules)], antigen-presenting cells such as dendritic cells pulsed with tumor-derived antigens or nucleic acid, cells transfected with immunostimulatory cytokine (e.g., IL-2, IFNα2, GM-CSF), and genes encoding immunostimulatory cytokine (including, but not limited to, GM-CSF); standard cancer therapy (e.g., chemotherapy, radiation therapy or surgery), or other antibodies (including, but not limited to, VEGF, EGFR, Her2/neu, VEGF receptors, other growth factor receptors, CD20, CD40, CTLA-4, OX-40, 4-IBB and ICOS).

Anti-PD-L1 antibodies can induce apoptosis (cell death). Apoptosis is induced by direct or indirect mechanisms. For example, binding of anti-PD-L1 antibodies to PD-L1 can cause complement dependent cytotoxicity (CDC). In some cases, the anti-PD-L1 antibody binds to PD-L1 and causes the mobilization of secondary cell types to kill PD-L1-expressing target cells. Representative mechanisms, by which anti-PD-L1 antibodies mediate apoptosis by the mobilization of secondary cell types, include, but are not limited to, antibody-dependent cytotoxicity (ADCC) and antibody-dependent cellular cytotoxicity (ADCP). Target PD-L1-expressing cell types include tumors and T cells such as activated T cells.

In addition, the antibody or an antibody fragment thereof according to the present disclosure can be used to prevent or treat infections and infectious diseases.

As used herein, the term "prevention" means any action that inhibits cancer or infectious diseases or delays the progress of the same by administration of a composition and, as used herein, the term "treatment" means inhibition of the development of cancer, or alleviation or elimination of cancer, or inhibition, alleviation or elimination of infectious diseases.

Cancer, the disease to which the composition is applied, typically includes cancer that responds to immunotherapy, and cancer that has been not involved in immunotherapy to date. Non-limiting examples of preferred cancer in need of treatment include, but are not limited to, melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, head and neck squamous cell carcinoma, liver cancer, ovarian cancer, cervical cancer, thyroid cancer, glioblastoma, glioma, leukemia, lymphoma, and other neoplastic carcinomas. In addition, the present disclosure includes refractory or recurrent cancers growth of which can be inhibited using the antibodies of the invention.

The antibody or antibody fragment may be used alone or in combination with a vaccine to stimulate an immune response to pathogens, toxins and auto-antigens. The antibody or an antigen-binding fragment thereof can be used to stimulate immune responses to human-infecting viruses, including, but not limited to, human immunodeficiency virus, hepatitis viruses A, B and C, Epstein-Barr virus, human cytomegalovirus, human papilloma and Herpes virus. The antibody or an antigen-binding fragment thereof can be used to stimulate immune responses to infection with bacterial or fungal parasites and other pathogens.

The pharmaceutically acceptable carriers, which are contained in the composition of the present disclosure, include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, water, syrup, methyl cellulose, methyl hydroxybenzoate, propyl hydroxybenzoate, talc, magnesium stearate, mineral oil and the like, which are conventionally used for drug preparation. In addition to the above components, the composition of the present disclosure may further contain a lubricant, a wetting agent, a sweetener, a flavor, an emulsifier, a suspending agent, a preservative or the like.

The pharmaceutical composition of the present disclosure can be administered orally or parenterally. In the case of parenteral administration, the pharmaceutical composition can be administered by intravenous injection, subcutaneous injection, intramuscular injection, intraperitoneal injection, endothelial administration, topical administration, intranasal administration, intrapulmonary administration, rectal administration and the like.

When administered orally, the protein or peptide may be digested. For this reason, the oral composition should be formulated to coat the active agent or protect the protein or peptide from digestion in the stomach. In addition, the pharmaceutical composition may be administered by any device enabling the active agent to be transferred to the target cell.

The appropriate dosage of the composition according to the present disclosure may vary depending on factors such as formulation method, administration method, age, body weight, gender, pathological condition and food of a patient, administration time, administration route, excretion rate and responsiveness. A skilled physician can readily determine and prescribe a dosage effective for desired treatment or prevention. For example, the daily dosage of the pharmaceutical composition of the present disclosure is 0.0001 to 100 mg/kg. As used herein, the term "pharmaceutically effective amount" means an amount sufficient to prevent or treat cancer.

The pharmaceutical composition of the present disclosure may be prepared into a unit dose form or incorporated into a multi-dose vial by formulating using a pharmaceutically acceptable carrier and/or excipient according to a method which can be easily carried out by a person having ordinary skill in the technical field to which the present disclosure pertains. The formulation may be in the form of a solution, suspension or emulsion in oil or aqueous media, or in the form of an excipient, powder, suppository, powder, granule, tablet or capsule, and may further contain a dispersant or a stabilizing agent.

The composition of the present disclosure may be administered as an individual therapeutic agent or in combination with other therapeutic agents, and may be administered sequentially or simultaneously with conventional therapeutic agents.

In another aspect, the present disclosure is directed to a composition for diagnosing cancer containing the antibody to PD-L1 or an antigen-binding fragment thereof according to the present disclosure. Also, the present disclosure is directed to a method for diagnosing cancer by treatment with the antibody to PD-L1 or an antigen-binding fragment thereof according to the present disclosure.

Cancer can be diagnosed by measuring the level of PD-L1 expression in a sample through the antibody to PD-L1 according to the present disclosure. The level of expression can be measured by a conventional immunoassay method that includes, but is not limited to, radioimmunoassay, radioimmunoprecipitation, immunoprecipitation, immunohistochemical staining, enzyme-linked immunosorbent assay (ELISA), captured-ELISA, inhibition or competition analysis, sandwich analysis, flow cytometry, immunofluorescent staining and immunoaffinity purification using the antibody to PD-L1.

Cancer can be diagnosed by analyzing the intensity of the final signal by the immunoassay process. That is, when protein of a marker according to the present disclosure is highly expressed in a biological sample and thus the signal of biological sample is stronger than that of a normal biological sample (for example, normal stomach tissue, blood, plasma or serum), cancer is diagnosed.

In another aspect, the present disclosure is directed to a kit for diagnosing cancer containing the composition for diagnosing cancer. The kit according to the present disclosure includes the antibody to PD-L1 according to the present disclosure and can diagnose cancer by analyzing a signal generated upon reaction between a sample and the antibody. The signal may include, but is not limited to, an enzyme coupled to an antibody such as alkaline phosphatase, β-galactosidase, horseradish peroxidase, luciferase or cytochrome P450. In this case, when alkaline phosphatase is used as an enzyme, as a substrate for the enzyme, a chromogenic reaction substrate such as bromochloroindole phosphate (BCIP), nitroblue tetrazolium (NBT), naphthol-AS-B1-phosphate and ECF (enhanced chemifluorescence) are used, and when horseradish peroxidase is used, a substrate such as chloronaphthol, aminoethylcarbazole, diaminobenzidine, D-luciferin, lucigenin (Bis-N-methyl acridinium nitrate), resorufin benzyl ether, luminol, Amplex Red reagent (10-acetyl-3,7-dihydroxy phenoxazine), HYR (p-phenylenediamine-HCl and pyrocatechol), TMB (tetramethylbenzidine), ABTS (2,2'-Azine-di[3-ethylbenzthiazoline sulfonate]), o-phenylenediamine (OPD) and naphthol/pyronin, glucose oxidase, t-NBT (nitroblue tetrazolium) or m-PMS (phenzaine methosulfate) is used, but the present disclosure is not limited thereto.

In addition, the kit according to the present disclosure may also include a label for generating a detectable signal and the label may include a chemical (e.g., biotin), an enzyme (alkaline phosphatase, β-galactosidase, horseradish peroxidase and cytochrome P450), a radioactive substance (such as C14, I125, P32 and S35), a fluorescent substance (such as fluorescein), a luminescent substance, a chemiluminescent substance and FRET (fluorescence resonance energy transfer), but is not limited thereto.

Measurement of the activity of the enzyme used for cancer diagnosis or measurement of the signal can be carried out by a variety of methods known in the art. Thus, PD-L1 expression can be qualitatively or quantitatively analyzed.

EXAMPLE

Hereinafter, the present disclosure will be described in more detail with reference to examples. However, it is obvious to those skilled in the art that these examples are provided only for illustration of the present disclosure and should not be construed as limiting the scope of the present disclosure.

Example 1: Expression and Purification of PD-L1 Antigen

1. Production of PD-1 Protein Expression Vectors

For cloning of PD-L1, amplification was conducted through polymerase chain reaction (PCR) using primers for PD-L1 containing restriction enzyme SfiI sites at 5' and 3' (Table 1) in order to obtain only an extracellular domain using Jurkat cell cDNA libraries (Stratagene, USA). The amplified PCR product was prepared by fusing human Fc (SEQ ID NO: 248) and mouse Fc (SEQ ID NO: 249) to a carboxyl terminal using N293F vector (FIG. 1).

TABLE 1

| Primers for PD-L1 expression vectors | | |
|---|---|---|
| Name | 5'->3' sequence | SEQ ID NO |
| PD-L1-F | ccaggatggttcttagactcccc | 250 |
| PD-L1-R | caccagggtttggaactggc | 251 |

2. Expression and Purification of PD-L1 Antigen

In order to express an antigen in animal cells, HEK-293F cells were transfected with plasmid DNA. The polyplex reaction solution for transfection was prepared by mixing 25 µg of plasmid DNA with 3 ml of a Freestyle 293 expression medium and further mixing 2 mg/ml of PET (polyethylenimine, polyplusA-transfection, USA) with the resulting mixture again. The polyplex reaction solution was reacted at room temperature for 15 minutes and then cultured in 40 ml of the culture medium ($1 \times 10^6$ cells/ml) for 24 hours at 37° C. and 8% $CO_2$ at 120 rpm. After 24 hours of transfection, Soytone (BD, USA), as a supplement, is added to a final concentration of 10 g/L. Antibodies were produced using a transient expression system using HEK-293F for 7 days. Affinity chromatography was performed to obtain the antigen from the culture medium. The supernatant was obtained by centrifugation at 5,000 rpm for 10 minutes to remove cells and cell debris from the culture medium recovered on the 7$^{th}$ day. The supernatant was reacted with a recombinant protein A agarose resin washed with DPBS at 4° C. for 16 hours.

When the recombinant protein A agarose resin was used, the protein was eluted with 0.1M glycine and neutralized with 500 µl of 1M Tris-HCl to perform primary purification. The primarily purified protein was secondarily purified using Superdex 200 (1.5 cm*100 cm) gel filtration chromatography.

The purity of the purified protein was identified by SDS-PAGE gel and size exclusion chromatography [TSK-GEL G-3000 SWXL size-exclusion chromatography (SEC) (Tosoh)].

As a result, it was confirmed that the purified PD-L1 protein had a purity of 95% or more, as shown in FIGS. 2A to 2D.

Example 2: Screening of PD-L1 Human Antibodies

1. Antigen Preparation

PD-L1-hFc and PD-L1-mFc prepared in Example 1 and PD-L1-his (Catalog Number, 10084-H08H) purchased from Sino Biological Inc. as protein antigens were coated in a dose of 50 ug on an immunosorbent tube and then blocked.

2. Bio-Panning

A human antibody library phage was obtained by infecting a human scFv library with a variety of $2.7 \times 10^{10}$ with bacteria and then culturing at 30° C. for 16 hours. After culturing, the culture solution was centrifuged, and the supernatant was concentrated with PEG, and then dissolved in PBS buffer to prepare a human antibody library. The human antibody library phage was charged into an immune tube, followed by reaction at room temperature for 2 hours. After washing with 1×PBS/T and 1×PBS, only the scFv-phages specifically bound to the antigen were eluted. The eluted phages were infected with *E. coli* again and amplified (panning process) to obtain a pool of positive phages. The second and third round panning processes were conducted using the phages amplified in the first round of panning in the same manner as above, except that only the number of times of the PBST washing step was increased. As a result, as shown in Table 2, it was seen that the number of phages bound to the antigen (output) during the third round panning was slightly increased, as compared to the input phages.

TABLE 2

Comparison in titer of antibodies depending on number of times of panning

| Number of (times) of panning | Number of input phages | Number of output phages |
| --- | --- | --- |
| 1 | $3 \times 10^{13}$ | $6 \times 10^{7}$ |
| 2 | $2 \times 10^{13}$ | $2 \times 10^{6}$ |
| 3 | $2.3 \times 10^{13}$ | $3 \times 10^{8}$ |

3. Polyphage ELISA

The cell stock frozen after the first to third panning processes was added to a medium containing 5 ml of 2×YTCM, 2% glucose and 5 mM MgCl$_2$ to OD$_{600}$ of 0.1 and then cultured at 37° C. for 2 to 3 hours (OD$_{600}$=0.5 to 0.7). M1 helper phages were infected and cultured in a medium containing 2×YTCMK, 5 mM MgCl$_2$, and 1 mM IPTG at 30° C. for 16 hours. The cultured cells were centrifuged (4,500 rpm, 15 min, 4° C.), and the supernatant was transferred to a new tube (first to third-panned poly scFv-phages). Two kinds of antigens were each coated at a density of 100 ng/well on 96-well immuno-plates (NUNC 439454) with coating buffer at 4° C. for 16 hours, and each well was blocked using 4% skim milk dissolved in PBS.

Each well was washed with 0.2 ml of PBS/T, and 100 µl of the first to third-panned poly scFv-phage was added to each well, followed by reaction at room temperature for 2 hours. Again, each well was washed 4 times with 0.2 ml of PBS/T, and the secondary antibody, anti-M13-HRP (Amersham 27-9421-01) was diluted at 1:2000 and reacted at room temperature for 1 hour. After washing with PBS/T, OPD tablets (Sigma. 8787-TAB) were dissolved in PC buffer, and the resulting solution was added at a concentration of 100 µl/well to induce color development for 10 minutes. Then, absorbance was measured at 490 nm with a spectrophotometer (Molecular Device).

The results are shown in FIG. 3. As can be seen from FIG. 3, ELISA showed that binding capacity to two PD-L1 antigens was enriched in the third poly scFv-phages.

4. Screening of Positive Phages

Colonies obtained from the polyclonal phage antibody group (third panning) with high binding capacity were cultured in a 1 ml 96-deep well plate (Bioneer 90030) at 37° C. for 16 hours. 100 to 200 µl of the cells grown thus were added to a medium containing 2×YTCM, 2% glucose and 5 mM MgCl$_2$, to OD$_{600}$ of 0.1, and were added to a medium containing 1 ml of 2×YTCM, 2% glucose and 5 mM MgCl$_2$, and then cultured in a 96-deep well plate at 37° C. for 2 to 3 hours to OD$_{600}$ of 0.5 to 0.7. M1 helper phages were infected at an MOI of 1:20 and cultured in a medium containing 2×YTCMK, 5 mM MgCl$_2$, 1 mM IPTG at 30° C. for 16 hours.

The antigen PD-L1 was coated at a density of 100 ng/well on a 96-well immunoplate at 4° C. for 16 hours and each well was blocked using 4% skim milk dissolved in PBS. Each monoclonal scFv-phage (100 scFv-phage) washed with 0.2 ml PBS/T and cultured for 16 hours was added in a dose of 100 µl to each well and reacted at room temperature for 2 hours. Again, each well was washed 4 times with 0.2 ml of PBS/T, and the secondary antibody, anti-M13-HRP, was diluted to ½000 and reacted at room temperature for 1 hour. After washing with 0.2 ml of PBS/T, color development was performed and absorbance was measured at 490 nm.

As a result, as shown in FIG. 4, a total of several tens of single-phage clones for PD-L1 were obtained as single-phage clones having high binding capacity to each antigen.

5. Base Sequence Analysis of Positive Phage Antibodies

The selected single clones were subjected to DNA-prep using a DNA purification kit (Qiagen, Germany) to obtain DNAs, and sequence analysis for DNAs was requested (Solgent). The CDR regions of V$_H$ and V$_L$ of the selected antibodies were identified, based on results of sequence analysis and the similarity (identity) between these antibodies and germ line antibody groups was investigated using an Ig BLAST program on the NCBI website at ncbi.nlm.nih.gov/igblast/. As a result, 10 species of phage antibodies specific to PD-L1 were obtained and are summarized in Table 3 below.

TABLE 3

Characteristics of PD-L1 monoclones

| Clone Name | VH | Identities | VL | Identities2 | Group |
|---|---|---|---|---|---|
| PDL1-11A7 | IGHV1-24 | 98.00% | IGKV1-12 | 93.70% | 1 |
| PDL1-16E12 | IGHV1-69 | 92.90% | IGLV1-40 | 89.90% | 2 |
| PDL1-22B10 | IGHV1-69 | 93.90% | IGLV1-40 | 90.90% | 3 |
| PDL1-23E5 | IGHV1-69 | 83.70% | IGLV1-40 | 79.80% | 4 |
| PDL1-23E10 | IGHV1-69 | 81.60% | IGLV1-40 | 96.00% | 5 |
| PDL1-27F8 | IGHV1-69 | 85.70% | IGLV1-40 | 90.90% | 6 |
| PDL1-30B1 | IGHV3-30 | 95.90% | IGKV2D-29 | 93.00% | 7 |
| PDL1-31B7 | IGHV1-69 | 93.90% | IGLV1-51 | 93.90% | 8 |
| PDL1-31D9 | IGHV3-64 | 90.80% | IGKV2-40 | 93.10% | 9 |
| PDL1-31E6 | IGHV1-69 | 99.00% | IGKV3-11 | 89.50% | 10 |

Antibodies including the heavy and light-chain CDRs and FR sequences of the selected antibodies, and heavy chain variable regions and light chain variable regions including the same are shown in Tables 4 and 5 below.

TABLE 4

Heavy chain variable regions of PD-L1 clones

| NAME | FR1 | CDR1 | FR2 | CDR2 | FR3 | CDR3 | FR4 |
|---|---|---|---|---|---|---|---|
| PDL1-11A7 | QVQLVQSGAEVKKPGASVKVSCKVS | GYTLTELS | MHWVRQAPGKGLEWMGG | FDPEDGET | IYAQKFQGRVTMTEDTSTDTAYMELSSLRSEDTAVYYC | ARDPWGGYYGMDV | WGQGTTVTVSS |
| SEQ ID NO | 26 | 1 | 35 | 8 | 42 | 16 | 50 |
| PDL1-16E12 | QMQLVQSGAEVKKPGSSVKVSCKVS | GGTFSSYA | ISWVRQAPGQGLEWMGR | IIPILGIA | NYAQKFQGRVTITADKSTSTAYMELSSLRSEDTAVYYC | ARDFVLSGSATVFDP | WGQGTLVTVSS |
| SEQ ID NO | 27 | 2 | 36 | 9 | 43 | 17 | 51 |
| PDL1-22B10 | QVQLVQSGAEVKKPGSSVKVSCRAS | GGTFSSYA | ISWVRQAPGQGLEWMGR | IIPILGIA | NYAQKFQGRVTITADKSTSTAYMELSSLRSEDTAVYYC | ARDFVLSGSATVFDP | WGQGTLVTVSS |
| SEQ ID NO | 28 | 2 | 36 | 9 | 43 | 18 | 52 |
| PDL1-23E5 | QVQLVQSGAEVKKPGSSVKVSCKAS | GDTFSRYA | ISWVRQAPGQAPEWMGR | IIPVLGA | NYARKFQDRVTITADISTTTAFMELTSLRSEDTAVYYC | ARSLSGYSLGAFDV | WGPGTLVTVSS |
| SEQ ID NO | 29 | 3 | 37 | 10 | 44 | 19 | 53 |
| PDL1-23E10 | QMQLVESGAEVKKPGSSVKVSCKVS | GENFRSHA | ISWVRQAPGQGLEWMGR | IIPVVGLA | DYPQKFQGRVTISADESTGTAYMDLSSLRSEDTAVYYC | VTGRPPWH | WGQGILITVSS |
| SEQ ID NO | 30 | 4 | 36 | 11 | 45 | 20 | 54 |
| PDL1-27F8 | QVQLVQSGAEVKKPGSSVKVSCKAS | GGTFSSSA | FSWVRQAPGHGLEWMGR | IIPMFDMT | DYAQRFQGRLTIIADESSSTAYMELSSLRSEDTAVYYC | ARSNPHYMDV | WGQGTTVTVSS |
| SEQ ID NO | 31 | 5 | 38 | 12 | 46 | 21 | 50 |
| PDL1-30B1 | QVQLVESGGGVVQPGRSLRLSCAAS | GFTFSSYA | MHWVRQGPGKGLEWVAV | ISYDGSNE | FYADSVKGRFTISRDNSKNTLYLQMNSLRAEDTAVYYC | ARGDYNGVYMDV | WGQGTTVTVSS |
| SEQ ID NO | 32 | 6 | 39 | 13 | 47 | 22 | 50 |

TABLE 4-continued

Heavy chain variable regions of PD-L1 clones

| NAME | FR1 | CDR1 | FR2 | CDR2 | FR3 | CDR3 | FR4 |
|---|---|---|---|---|---|---|---|
| PDL1-31B7 | QVQLVES GAEVKKP GSSVKVSC KAS | GGT FSS YA | ISWVRQA PGQGLEW MGR | IIPIL GIA | NYAQKFQGRVTITAD KSTSTAYMELSSLRSE DTAVYYC | ARASSGYS VGAFDI | WGQG TMVT VSS |
| SEQ ID NO | 33 | 2 | 36 | 9 | 43 | 23 | 51 |
| PDL1-31D9 | QMQLVES GGGLVQP GGSLRLSC SAS | GFT FSS YV | MHWVRQ APGKGLE YVSA | ISSN GGS T | YYADSVKGRFTISRDN SKNTLYLQMSSLRSED TAVYYC | AREHFSTY SYGVDV | WGPG TTVT VSS |
| SEQ ID NO | 34 | 7 | 40 | 14 | 48 | 24 | 55 |
| PDL1-31E6 | QVQLVQS GAEVKKP GSSVKVSC KAS | GGT FSS YA | ISWVRQA PGQGLEW MGG | IIPIF GTA | NYAQKFQGRVTITADE STSTAYMELSSLRSED TAVYYC | ARGGRSFG AFDS | WGQG ALVT VSS |
| SEQ ID NO | 31 | 2 | 41 | 15 | 49 | 25 | 56 |

TABLE 5

Light chain variable regions of PD-L1 clones

| NAME | FR1 | CDR1 | FR2 | CDR2 | FR3 | CDR3 | FR4 |
|---|---|---|---|---|---|---|---|
| PDL1-11A7 | DIQMTQSPSS VSASVGDRV TINCRAS | QGIRT W | LAWYQQK PGKAPKLL IY | AAS | NLQSGVPSRFSGS GSGTDFTLTIASLQ PEDFATYYC | QQANS FPLT | FGGG TKVEI K |
| SEQ ID NO | 145 | 88 | 164 | 103 | 185 | 120 | 211 |
| PDL1-16E12 | QLVLTQPPSV SGAPGQTVTI SCTGS | SSNIG AGYD | VHWYQQL PGTAPKLL IY | GNN | NRPSGVPDRFSGS KSGALASLAITGL QAEDGADYHC | QSYDN SLSAH AV | FGTG TKVT VL |
| SEQ ID NO | 146 | 89 | 165 | 104 | 186 | 121 | 212 |
| PDL1-22B10 | QFVLTQPPSV SGAPGQRVTI SCTGS | STNIG AGYD | VHWYQQL VIY | GNS | NRPSGVLDRFSAS KSATSASLAITGL QAEDEADYYC | QSYDS SLSGY V | FGTG TKVT VL |
| SEQ ID NO | 147 | 90 | 166 | 105 | 187 | 122 | 212 |
| PDL1-23E5 | QLVLTQPPSV SGAPGQSVSI SCIGS | NSNIG TPYD | VHWYQQI PGEAPKLL IY | GST | NRPSGVPDRFSGS RSGSSASLDITGLQ ADDEAYYYC | QSYDR SLGVS DVV | FGGG TKLT VL |
| SEQ ID NO | 148 | 91 | 167 | 106 | 188 | 123 | 213 |
| PDL1-23E10 | QLVLTQPPSV SGAPGQRVTI SCTGS | SSNIG AGYD | VHWYQQL PGTAPKLL IY | SNR | NRPSGVPDRFSGS KSGTSASLAITGL QAEDEADYYC | QSYDS SLSGP NYV | FGTG TKVT VL |
| SEQ ID NO | 149 | 89 | 165 | 107 | 189 | 124 | 212 |
| PDL1-27F8 | QLVLTQPPSV SGAPGQRVTI SCTGS | NSDIG AGHD | VHWYQQI PGTAPKVL IY | GNT | DRPSGVPDRFSGS KSGTSASLAITGL QAEDEADYYC | QSYDS SLSGY V | FGTG TKVT VL |
| SEQ ID NO | 149 | 92 | 168 | 108 | 190 | 122 | 212 |
| PDL1-30B1 | DIVMTQTPLS LSVTPGQPAS ISCKSS | QSLLH SDGKT Y | LYWYLQK PGQSPQLL IY | EVS | KRFSGVPDRFSGS GSGTDFTLKIGRV EAEDVGVYYC | MQGL HLPYT | FGQG TKLEI K |
| SEQ ID NO | 150 | 93 | 169 | 109 | 191 | 125 | 214 |

TABLE 5-continued

Light chain variable regions of PD-L1 clones

| NAME | FR1 | CDR1 | FR2 | CDR2 | FR3 | CDR3 | FR4 |
|---|---|---|---|---|---|---|---|
| PDL1-31B7 | QLVLTQPPSV SAPPGQKVTI SCSGS | SSNIG NNY | VSWYQQL PGTAPKLL IY | DNN | ERPSGIPDRFSASK SGTSATLGISGLQT GDEADYYC | GTWDS SLSAG V | FGGG TKLT VL |
| SEQ ID NO | 151 | 94 | 170 | 110 | 192 | 126 | 213 |
| PDL1-31D9 | DIVMTQTPLS LTVTPGEPAS ISCRSS | QSLLD SDDGN TY | LDWYLQK PGQSPQLL IY | MIS | FRASGVPDRFSGS GSGTDFTLKISRVE AEDSGIYYC | MQRV EFPYT | FGQG TKLEI K |
| SEQ ID NO | 152 | 95 | 171 | 111 | 193 | 127 | 214 |
| PDL1-31E6 | DIQMTQSPA TLSLSPGERA TLSCTAS | QSISSY | LAWYQQK PGQAPRLL IY | DSS | NRATGIPARFSGS GSGTAFTLTISSLE PEDFAVYFC | QQRGQ WPLT | FGGG TKVD IK |
| SEQ ID NO | 153 | 96 | 172 | 112 | 194 | 128 | 215 |

Example 3: Production of PD-L1 Human Antibody

1. Conversion of scFv Form to IgG Form

PCR (iCycler iQ, BIO-RAD) was performed on the heavy and light chains to convert the selected 10 species of monoclonal phage antibodies to PD-L1 from phages to IgG whole vector. As a result, heavy and light chains were obtained, and the vectors and the heavy and light chains of each of the clones were cut (digested) with restriction enzymes. DNAs were eluted from each of the vector and heavy chain with a DNA-gel extraction kit (Qiagen). Ligation was performed by mixing 1 μl (10 ng) of the vector, 15 μl (100-200 ng) of the heavy chain, 2 μl of 10× buffer, 1 μl of ligase (1 U/μl) and distilled water, allowing the mixture to stand at room temperature for 1 to 2 hours, injecting the resulting mixture into transformed cells (competent cells, XL1-blue), placing the cells on ice for 5 minutes and subjecting the cells to heat-shock at 42° C. for 90 seconds.

After the heat shock, 1 ml of the medium was added to the cells, and then the cells were grown at 37° C. for 1 hour, spread on an LB Amp plate and incubated at 37° C. for 16 hours. The colony thus obtained was inoculated with 5 ml of LB Amp medium, cultured at 37° C. for 16 hours and subjected to DNA-prep using a DNA-prep kit (Nuclogen). Sequence analysis of the obtained DNAs was requested (Solgent).

As a result, it was confirmed that the sequences of heavy chains and light chains of 11 clones for PD-L1 converted into the whole IgG corresponded to the sequences of phage antibodies. In order to transfect into HEK 293F cells, the heavy and light chains of respective clones converted into whole IgG were grown in 100 ml of LB Amp medium, and DNAs were obtained using a Midi-prep kit (QIAgen).

2. Human Antibody Production

The cloned pNATVH and pNATVL vectors were co-transfected at a ratio of 6:4 into HEK293F cells and the supernatant was collected on the 7$^{th}$ day, the cells and debris were removed through centrifugation and a 0.22 μm top filter, and the supernatant was collected and subjected to protein A affinity chromatography to purify the IgG antibody. After purification, the antibody was separated through a glycine buffer, and buffer was changed such that the final resuspension buffer was PBS. Purified antibodies were quantitated by BCA and nano drop, and each of 15 species of antibodies was loaded in a dose of 5 ug under reducing and non-reducing conditions, and analyzed by SDS-PAGE to determine purity and mobility of the purified protein (FIG. 5).

As a result, as shown in FIG. 5, all of the 10 antibodies were detected at a molecular weight of 150 kDa or more under non-reducing conditions.

Example 4: Characteristics of PD-L1 Monoclonal Antibody

1. Evaluation of Antibody Activity

Testing for activity of the selected antibodies was carried out using a PD1/PD-L1 blockade bioassay kit (promega, J1250). A CHO cell line highly expressing PD-L1 was spread on a 96-well plate, cultured for 16 hours or longer, treated with each antibody serially diluted at a constant concentration and then cultured together with a Jurkat cell line highly expressing human PD-1, for 6 hours. The degree of recovery of the inhibition of the antibody was determined with a spectrophotometer (SpectraMax M5 spectrophotometer, Molecular Devices, USA), which was determined from a luminescent intensity resulting from degradation of the substrate by luciferase. The activity of 10 species of PD-L1 antibodies was found based on the value to recover a reduced signal by formation of a PD-1/PD-L1 complex, and 16E12 exhibited similar activity to the control antibody (FIG. 6).

In order to measure activity of the PD-L1 antibody, 16E12 in a concentration-dependent manner, serial dilution and PD-1/PD-L1 blockade bioassay were performed again to recover the reduced signal in a concentration gradient dependent manner. The degree of recovery can be expressed as EC50 (effective concentration of mAb at 50% level of recovery signal), analyzed using Graphpad Prism6, and in vitro efficacy inhibition recovery ability of EC50 is shown in FIG. 7.

2. Affinity of PD-L1 Antibody to Overexpressed Cells

Regarding transformation cell pools highly expressing PD-L1, HEK293E was transformed with a plasmid pcDNA3.1 containing human PD-L1 and screened in a selective medium containing 150 ug/ml Zeocin (#R25001, Thermo Fisher). Each cell pool was identified and selected by fluorescence activated cell sorting (FACS) analysis using anti-PD-L1 and used for functional assays such as FACS binding assays or FACS competition assays.

0.5 to 1×10⁶ cells per sample were each prepared from the transformation cell pools highly expressing human PD-L1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer. As a result, the PD-L1 antibody, 16E12, was specifically bound and the binding capacity thereof was determined from an equilibrium dissociation constant (Kd) obtained through an analysis function of Graphpad Prism6.

As a result, as can be seen from FIG. 8, the binding capacity of antibody bound in a concentration-dependent manner to human PD-L1 over-expressed on the cell surface can be found by MFI (mean fluorescence intensity).

3. Affinity of PD-L1 Antibody Using ProteOn XPR36

A ProteOn XPR36 (BioRad) instrument was used. The GLC sensor chip (BioRad) was mounted on the instrument and washed with PBST buffer, and the carboxymethyldextran surface was activated with an EDC/sulfo-NHS mixed solution. PD-L1-hFc dissolved at a concentration of 5 ug/ml in a 10 mM sodium acetate buffer solution (pH 5.0) was injected and immobilized on the GLC sensor chip.

In order to deactivate the activated carboxyl groups that remain unreacted with the PD-L1 protein, 1 M ethanolamine was flowed and 10 mM glycine (pH 2.0) was injected in order to wash proteins that remain unbound to the sensor chip. Then, sensogram data were collected during binding and dissociation over time while allowing the antibodies to flow at a flow rate of 30 μL/min (30 nM to 0.123 nM) for 10 min using PBST buffer.

The equilibrium dissociation constant ($K_D$) was calculated by plotting and fitting the sensogram data in the equilibrium state depending on concentration. As a result, 16E12 exhibited $K_D$ of 0.045 nM, indicating high affinity to the PD-L1 antigen (FIG. 9).

Example 5: Antibody Optimization for PD-L1 Antibody, 16E12

1. Production of Libraries for Optimization of PD-L1-16E12 Antibody

For antibody optimization, new LC shuffling libraries were produced by immobilizing the heavy chain and injecting a 10⁵-10⁶ light chain (LC) pool owned by Ybiologics, Inc. Also, antibody optimization was conducted by the following three methods: LC shuffling; core packing+LC shuffling including comparatively analyzing the residues of structurally important sites such as hydrophobic cores of heavy chains, exposed residues, charge clusters, salt bridges, mutating the same into conserved residues and then conducting LC shuffling; and CDR hotspot+LC shuffling, in the case of DNAs in antibody variable regions, including randomly mutating mutational hot spots that can be mutated frequently in the process of in vivo affinity maturation and then conducting LC shuffling.

In order to produce LC shuffling libraries, LC genes of the 16E12 antibody were cut (digested) with BstX I and then used as vectors and the library pools owned by Ybiologics, Inc. were cut (digested) into BstX I and used as inserts. After ligation with a ligase, transformation was carried out using cells for electroporation transformation. The antibody libraries were produced by collecting the transformed cells on a square plate. As a result, about 1.5×10⁷ various libraries were obtained. The result of sequence analysis showed that all HC sequences were identical and LC sequences were different from each other.

In order to produce the core packing+LC shuffling libraries, the framework (FR) sites of the 16E12 antibody were replaced with conserved amino acid sequences, the LC genes were cut with BstX I and then used as vectors, and the library pools owned by Ybiologics, Inc. were cut with BstX I and then used as inserts. After ligation with a ligase, transformation was carried out using cells for electroporation transformation. The antibody libraries were produced by collecting the transformed cells on a square plate. As a result, about 8.4×10⁶ various libraries were obtained. The result of sequence analysis showed that the FR sites of HC were replaced with conserved amino acid sequences and LC sequences were different from each other.

In order to produce the core hot spot+LC shuffling libraries, the framework (FR) sites of the 16E12 antibody were replaced with conserved amino acid sequences, the hot spot libraries of CDR1 were cut with Sfi I and used as inserts, and the library pools owned by Ybiologics, Inc. were cut with Sfi I and then used as vectors. After ligation with a ligase, transformation was carried out using cells for electroporation transformation. The antibody libraries were produced by collecting the transformed cells on a square plate. As a result, about 5.6×10⁶ various libraries were obtained. The result of sequence analysis showed that the FR sites of HC were replaced with conserved amino acid sequences, the hot spot sequences of CDR1 were randomly mutated and LC sequences were different from each other.

Example 6: Screening of PD-L1 Human Antibodies

1. Antigen Preparation

PD-L1-hFc and PD-L1-mFc produced by Ybiologics, Inc, and PD-L1-his (Catalog Number, 10377-H08H) purchased from Sino Biological Inc. as protein antigens were coated in a dose of 50 ug on an immunosorbent tube and then blocked.

2. Bio-Panning

A human antibody library phage was obtained by infecting a human scFv library with a variety of 2.7×10¹⁰ with bacteria and then culturing at 30° C. for 16 hours. After culturing, the culture solution was centrifuged, and the supernatant was concentrated with PEG, and then dissolved in PBS buffer to prepare a human antibody library. The human antibody library phage was charged into an immune tube, followed by reaction at room temperature for 2 hours. After washing with 1×PBS/T and 1×PBS, only the scFv-phages specifically bound to the antigen were eluted.

The eluted phages were infected with *E. coli* again and amplified (panning process) to obtain a pool of positive phages. For antibody optimization, only the first round of panning was conducted. As a result, as shown in Table 6, it was seen that the number of phages bound to the antigen (output) during the first round of panning was slightly increased, as compared to the input phages.

TABLE 6

Comparison in titer of antibodies in optimization panning

| Sample | Number of input phages | Number of output phages |
| --- | --- | --- |
| 16E12 (LS) | 1.3 × 10¹³ | 2.8 × 10⁷ |
| 16E12 (Core packing + LS) | 1.1 × 10¹³ | 1.8 × 10⁶ |
| 16E12 (CDR hotspot + LS) | 1.1 × 10¹³ | 1.6 × 10⁶ |

3. Screening of Positive Phages

Colonies obtained from panning were cultured in a 1 ml 96-deep well plate (Bioneer 90030) at 37° C. for 16 hours.

100 to 200 µl of the cells grown thus were added to a medium containing 2×YTCM, 2% glucose and 5 mM MgCl$_2$, to OD$_{600}$ of 0.1, and were added to a medium containing 1 ml of 2×YTCM, 2% glucose and 5 mM MgCl$_2$, and then cultured in a 96-deep well plate at 37° C. for 2 to 3 hours to OD$_{600}$ of 0.5 to 0.7. M1 helper phages were infected at an MOI of 1:20 and cultured in a medium containing 2×YTCMK, 5 mM MgCl$_2$, and 1 mM IPTG at 30° C. for 16 hours.

The antigen PD-L1 was coated at a density of 100 ng/well on a 96-well immunoplate at 4° C. for 16 hours and each well was blocked using 4% skim milk dissolved in PBS. Each monoclonal scFv-phage (100 scFv-phage) washed with 0.2 ml of PBS/T and cultured for 16 hours was added in a dose of 1 µl to each well and reacted at room temperature for 2 hours. Again, each well was washed 4 times with 0.2 ml of PBS/T, and the secondary antibody, anti-M13-HRP, was diluted to ½000 and reacted at room temperature for 1 hour. After washing with 0.2 ml of PBS/T, color development was performed and absorbance was measured at 490 nm.

As a result, single-phage clones having higher binding capacity to each antigen than the parent antibody (16E12, red-marked, 6D) were obtained and results are shown in FIG. 10.

4. Base Sequence Analysis of Positive Phage Antibodies

The selected single clones were subjected to DNA-prep using a DNA purification kit (Qiagen, Germany) to obtain DNA, and sequence analysis for DNA was requested (Solgent). The CDR regions of VH and VL of the selected antibodies were identified, based on results of sequence analysis and the similarity (identity) between these antibodies and germ line antibody groups was investigated using an Ig BLAST program on the NCBI website at ncbi.nlm.nih.gov/igblast/. As a result, 21 species of phage antibodies having higher binding capability than the parent antibody were obtained and are summarized in Table 7 below.

TABLE 7

Characteristics of optimized PD-L1 monoclones

| Clone name | VH | Identity | VL | Identity 2 | Group |
|---|---|---|---|---|---|
| PDL1-16E12 (LS/4A6) | IGHV1-69 | 92.86% | IGLV1-40 | 90.91% | 1 |
| PDL1-16E12 (LS/4A7) | IGHV1-69 | 92.86% | IGLV1-40 | 88.89% | 2 |
| PDL1-16E12 (LS/4A8) | IGHV1-69 | 92.86% | IGLV1-40 | 85.86% | 3 |
| PDL1-16E12 (LS/4A10) | IGHV1-69 | 92.86% | IGLV1-40 | 87.88% | 4 |
| PDL1-16E12 (LS/4A11) | IGHV1-69 | 92.86% | IGLV1-40 | 90.91% | 5 |
| PDL1-16E12 (LS/4B7) | IGHV1-69 | 92.86% | IGLV1-40 | 88.89% | 6 |
| PDL1-16E12 (LS/4B8) | IGHV1-69 | 92.86% | IGLV1-40 | 84.85% | 7 |
| PDL1-16E12 (LS/4B11) | IGHV1-69 | 92.86% | IGLV1-40 | 86.87% | 8 |
| PDL1-16E12 (LS/4B12) | IGHV1-69 | 92.86% | IGLV1-40 | 89.90% | 9 |
| PDL1-16E12 (LS/4C9) | IGHV1-69 | 92.86% | IGLV1-40 | 88.89% | 10 |
| PDL1-16E12 (LS/4D4) | IGHV1-69 | 92.86% | IGLV1-40 | 92.93% | 11 |
| PDL1-16E12 (LS/4E5) | IGHV1-69 | 92.86% | IGLV1-40 | 90.91% | 12 |
| PDL1-16E12 (LS/4E12) | IGHV1-69 | 92.86% | IGLV1-40 | 86.87% | 13 |
| PDL1-16E12 (LS/4F5) | IGHV1-69 | 92.86% | IGLV1-40 | 93.94% | 14 |
| PDL1-16E12 (LS/4F11) | IGHV1-69 | 92.86% | IGLV1-40 | 94.95% | 15 |
| PDL1-16E12 (LS/4G1) | IGHV1-69 | 92.86% | IGLV1-40 | 89.90% | 16 |
| PDL1-16E12 (LS/4H5) | IGHV1-69 | 92.86% | IGLV1-40 | 97.98% | 17 |
| PDL1-16E12 (LS/4H6) | IGHV1-69 | 92.86% | IGLV1-40 | 88.89% | 18 |
| PDL1-16E12 (LS/4H8) | IGHV1-69 | 92.86% | IGLV1-40 | 96.97% | 19 |
| PDL1-16E12 (LS/4H9) | IGHV1-69 | 92.86% | IGLV1-40 | 90.91% | 20 |
| PDL1-16E12 (LS/4H11) | IGHV1-69 | 92.86% | IGLV1-40 | 91.92% | 21 |

Antibodies including the heavy and light-chain CDRs and FR sequences of the selected antibodies, and heavy chain variable regions and light chain variable regions including the same are shown in Tables 8 and 9 below.

TABLE 8

Heavy chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4A6) | QMQLVQSGA EVKKPGSSVK VSCKAS | GGT FSS YS | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4A7) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |

TABLE 8-continued

Heavy chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4 A8) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-1612 (LS/4 A10) | QMQLVQSGA EKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 A11) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 B7) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 B8) | QMQLVQSGA EVKKPGSSVK VSCKAS | GGT GSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 B11) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 B12) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 C9) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 D4) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 E5) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 E12) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |

TABLE 8-continued

Heavy chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4 F5) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 F11) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 G1) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 H5) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 H6) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 H8) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 H9) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |
| PDL1-16E12 (LS/4 H11) | QMQLVQSGA EVKKPGSSVK VSCKAS | GGT FSS YA | ISWVRQA PGQGLE WMGR | IIPI LG IA | NYAQKFQGRVTITA DKSTSTAYMELSSLR SEDTAVYYC | AKPRD GYNLV AFDI | WGQ GTMV TVSS |
| SEQ ID NO | 27 | 2 | 36 | 9 | 43 | 17 | 51 |

TABLE 9

Light chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4A 6) | QLVLTQPTSV SGAPGQRVIIS CTGS | SSNI GAG YD | VHWYQQ LPGTAPK LLIY | GNT | NRPSGVPDRFSGSKS GTAASLAITGLQAED EADYYC | QSFDR SRSGS NV | FGTG TKVT VL |
| SEQ ID NO | 154 | 89 | 165 | 108 | 195 | 129 | 212 |

TABLE 9-continued

Light chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4A 7) | QLVLTQPPSV SGAPGQRVTI SCTGS | SSNI GAG YD | VHWYQS LPGTVPK LLIS | GNS | NRPPGVPDRFSGSKS GTSASLAITSLQSEDE ADYYC | HSYD GSLSE GV | FGTG TKVT VL |
| SEQ ID NO | 149 | 89 | 173 | 105 | 196 | 130 | 212 |
| PDL1-16E12 (LS/4A 8) | QLVLTQPPSV SGAPGQRVTI SCTGS | SSNI GAG YD | VHWYQH RPGKAPQ LLIY | GDN | NRPSGIPDRFSGSKSG TSASLAITGLQPEDEA DYYC | QSFDS RLGV V | FGGG TKLT VL |
| SEQ ID NO | 149 | 89 | 174 | 113 | 197 | 131 | 213 |
| PDL1-16E12 (LS/4A 10) | QLVLTQPPSV SGAPGQRVTI SCTGS | NSNI GAG YD | VHWYQQ LPGTAPK LLIH | GNN | IRPSGVPDRFSGSRSG TSASLAITGLQADDE ANYFC | QSYD NSLRG SV | FGTG TKVT VL |
| SEQ ID NO | 149 | 97 | 175 | 104 | 198 | 132 | 212 |
| PDL1-16E12 (LS/4A 11) | QLVLTQPPSV SGAPGQRVIIS CTGS | SSNI GAG YD | VHWYQQ VPGTAPK LLIY | GNN | HRPSGVPDRFSGSKS GTSASLAITGLQAED ETDYYC | QSYD NRLSG SL | FGGG TKLT VL |
| SEQ ID NO | 155 | 89 | 176 | 104 | 199 | 133 | 213 |
| PDL1-16E12 (LS/4B 7) | QLVLTQPPSV SGAPGQRVTI SCTGT | NSNI GAG YD | VHWYQQ LPGTAPK LLIV | TNH | NRPSGVPDRFSGSKS DTSASLALTGLQAED EATYYC | QSYDS RLSGP V | FGTG TKVT VL |
| SEQ ID NO | 156 | 97 | 177 | 114 | 200 | 134 | 212 |
| PDL1-16E12 (LS/4B 8) | QLVLTQPPSV SGAPGQSVTIS CTGS | NSDI GAG HD | VHWYQQ LPGAAPK LLIH | GDR | DRPSGVPDRFSGSKS GTSASLAITGLQPEDE ADYYC | QSYN NSLRG SV | FGTG TKVT VL |
| SEQ ID NO | 158 | 92 | 178 | 115 | 201 | 135 | 212 |
| PDL1-16E12 (LS/4B 11) | QLVLTQPPSV SGAPGQRVTI SCTGT | NSNI GAG HD | VQWYQQ IPGTAPKL LIY | GNN | NRPSGVPDRFSGSKS GTLASLAITGLQSED EADYYC | HSYD GSLSE GV | FGTG TKVT VL |
| SEQ ID NO | 157 | 98 | 179 | 104 | 202 | 130 | 212 |
| PDL1-16E12 (LS/4B 12) | QLVLTQPPSV SGAPGQRVTI SCTGS | SSNI GAG YD | VHWYQQ LPGTAPK LIIY | GDT | KRASGVPDRFSGSKS GTSASLAITGLQAED GADYYC | QSYD NSLSA HAV | FGTG TKVT VL |
| SEQ ID NO | 149 | 89 | 180 | 116 | 203 | 121 | 212 |
| PDL1-16E12 (LS/4C 9) | QLVLTQPPSV SGAPGQRVTI SCTGG | SSNI GAG YD | VHWYQQ LPGTAPK LLLF | GNT | NRPSGVPGRFSGSKS GSSASLAITGLQSDD EADYYC | QSYDS SLGGS V | IGTG TKVT VL |
| SEQ ID NO | 159 | 89 | 181 | 108 | 204 | 136 | 216 |
| PDL1-16E12 (LS/4D 4) | QLVLTQPSSV SGAPGQRVTI SCTGS | SSNL GAP YD | VHWYQQ LPGTAPK LLIY | GNS | NRPSGVPDRFSVSKS GTSASLAITGLQAED EADYYC | QSYDS SLSSS V | FGGG TKLT VL |
| SEQ ID NO | 160 | 99 | 165 | 105 | 205 | 137 | 213 |
| PDL1-16E12 (LS/4E 5) | QLVLTQPPSV SGAPGQGVTI SCTGD | SSNI GAG YD | VHWYQQ FPGTAPK LLIY | ENS | NRPSGVPDRFSGSKS GTSASLAITGLQAED EADYYC | QSYDS RLGA V | FGGG TKLT VL |
| SEQ ID NO | 161 | 89 | 182 | 117 | 189 | 138 | 213 |

TABLE 9-continued

Light chain variable regions of PD-L1 human antibodies

| NAME | FR1 | CDR1 | FR2 | CDR2 | FR3 | CDR3 | FR4 |
|---|---|---|---|---|---|---|---|
| PDL1-16E12 (LS/4E12) | QLVLTQPPSV SAAPGQKVTF SCTGS | SSNI GAG YD | VHWYQH LPGAAPR LLIY | ANT | NRPLGVPDRFSGSKS GTSASLAITGLQAED EADYYC | QSYD NRLSG SL | FGGG TKLT VL |
| SEQ ID NO | 162 | 89 | 183 | 118 | 206 | 133 | 213 |
| PDL1-16E12 (LS/4F5) | QLVLTQPPSV SGAPGQRVTI SCTGS | SSNI GAG YD | VHWYQQ LPGAAPK LLIY | GDI | NRPSGVPDRFSGSKS GISASLAITGLQAEDE ADYYC | QSYDS SLSGG V | FGGG TKLT VL |
| SEQ ID NO | 149 | 89 | 184 | 119 | 207 | 139 | 213 |
| PDL1-16E12 (LS/4F11) | QFVLTQPPSV SGAPGQRVTI SCTGS | SSNI GAG SD | VHWYQQ LPGTAPK LLIY | GNN | NRPSGVPDRFSGSKS GTSASLAITGLQAED EADYYC | QSYDS SLNGV V | FGGG TKLT VL |
| SEQ ID NO | 147 | 100 | 165 | 104 | 189 | 140 | 213 |
| PDL1-16E12 (LS/4G1) | QLVLTQPPSV SGAPGQRVTI SCTGG | SSNI GAG YD | VHWYQQ LPGTAPK LLLF | GNT | NRPSGVPGRFSGSKS GSSASLAITGLQSDD EADYYC | QSYDS SLSGS V | FGTG TKVT VL |
| SEQ ID NO | 159 | 89 | 181 | 108 | 204 | 141 | 212 |
| PDL1-16E12 (LS/4H5) | QLVLTQPPSV SGAPGQRVTI SCTGS | SSNI GAG YD | VHWYQQ LPGTAPK LLIY | GNS | NRPSGVPDRFSGSKS GTSASLAITGLQAED EADYYC | QSYDS SLSGG V | FGGG TKLT VL |
| SEQ ID NO | 149 | 89 | 165 | 105 | 189 | 139 | 213 |
| PDL1-16E12 (LS/4H6) | QLVLTQPPSV SAAPGQTVTIS CTGS | SSNI GAG YD | VHWYQQ FPGTAPK LLIY | GNN | NRPSGVPDRFSGSKS GTSASLAITGLQTDD EADYFC | QSYDS SLRVS SV | FGTG TKVT VL |
| SEQ ID NO | 163 | 89 | 182 | 104 | 208 | 142 | 212 |
| PDL1-16E12 (LS/4H8) | QLVLTQPSSV SGAPGQRVTI SCTGS | SSNI GAG YD | VHWYQQ LPGTAPK LLIY | GNS | NRPSGVPDRFSGSKS GTSASLAITGLQAED EADYYC | QSYDS SLSGS GV | FGTG TKVT VL |
| SEQ ID NO | 160 | 89 | 165 | 105 | 189 | 143 | 212 |
| PDL1-16E12 (LS/4H9) | QFVLTQPPSV SGAPGQRVTI SCTGS | RSNF GAG HD | VHWYQQ LPGTAPK LLIY | GNN | NRPSGVPDRFSGSKS GTSASLAIAGLQSDD EADYYC | QSYDS SLSGS V | FGTG TKVT VL |
| SEQ ID NO | 147 | 101 | 165 | 104 | 209 | 141 | 212 |
| PDL1-16E12 (LS/4H11) | QLVLTQPPSV SGAPGQRVTI SCTGS | SSNV GAG YD | VHWYQQ LPGTAPK LLIY | GNN | NRPSGVPARFSGSKS GTSASLAITGLQAED EADYYC | QSYDS RLGV V | FGGG TKLT VL |
| SEQ ID NO | 149 | 102 | 165 | 104 | 210 | 144 | 213 |

Example 7: Production of PD-L1 Human Antibody

1. Conversion of scFv Form to IgG Form

PCR (iCycler iQ, BIO-RAD) was performed on the heavy and light chains to convert the selected 21 species of monoclonal phage antibodies to PD-L1 from phages to IgG whole vector. As a result, heavy and light chains were obtained, and the vectors and the heavy and light chains of each of the clones were cut (digested) with restriction enzymes. DNAs were eluted from each of the vector and heavy chain with a DNA-gel extraction kit (Qiagen). Ligation was performed by mixing 1 µl (10 ng) of the vector, 15 µl (100-200 ng) of the heavy chain, 2 µl of 10× buffer, 1 µl of ligase (1 U/µl) and distilled water, allowing the mixture to stand at room temperature for 1 to 2 hours, injecting the resulting mixture into transformed cells (competent cells, XL1-blue), placing the cells on ice for 5 minutes and subjecting the cells to heat-shock at 42° C. for 90 seconds.

After the heat shock, 1 ml of the medium was added to the cells, and then the cells were grown at 37° C. for 1 hour, spread on an LB Amp plate and incubated at 37° C. for 16 hours. The colony thus obtained was inoculated with 5 ml of LB Amp medium, cultured at 37° C. for 16 hours and subjected to DNA-prep using a DNA-prep kit (Nuclogen). Sequence analysis of the obtained DNAs was requested (Solgent).

As a result, it was confirmed that the sequences of heavy chains and light chains of 21 clones for PD-L1 converted into the whole IgG corresponded to the sequences of the phage antibodies. In order to transfect into HEK 293F cells, the heavy and light chains of respective clones converted into whole IgG were grown in 100 ml of LB Amp medium, and DNAs were obtained using a Midi-prep kit (QIAgen).

2. Human Antibody Production

The cloned pNATVH and pNATVL vectors were co-transfected at a ratio of 6:4 into HEK293F cells and the supernatant was collected on the 7$^{th}$ day, the cells and debris were removed through centrifugation and a 0.22 μm top filter, and the supernatant was collected and subjected to protein A affinity chromatography to purify the IgG antibody. After purification, the antibody was separated through a glycine buffer, and buffer was changed such that the final resuspension buffer was PBS. Purified antibodies were quantitated by BCA and nano drop, and each of 21 species of antibodies was loaded in a dose of 5 ug under reducing and non-reducing conditions, and analyzed by SDS-PAGE to determine purity and mobility of the purified protein. In addition, some of the supernatants were loaded on SDS-PAGE to compare the expression rates with the parent antibody, the majority of the antibodies were more expressed than the parent antibody.

Example 8: Characteristics of PD-L1 Monoclonal Antibody

1. Evaluation of Antibody Activity

Testing for activity of the selected antibodies was carried out using a PD-1/PD-L1 blockade bioassay kit (promega, J1250). A CHO cell line highly expressing PD-L1 was spread on a 96-well plate, cultured for 16 hours or longer, treated with each antibody serially diluted at a constant concentration, and then cultured together with a Jurkat cell line highly expressing human PD-1, for 6 hours. The degree of recovery of the inhibition of the antibody was determined with a spectrophotometer (SpectraMax M5 spectrophotometer, Molecular Devices, USA), which was determined from a luminescent intensity resulting from degradation of the substrate by luciferase. The activity of 21 species of PD-L1 antibodies was found based on the value to recover a reduced signal by formation of a PD-1/PD-L1 complex, and 4A7, 4A11, 4C9, 4F5, 4H5 and 4H8 exhibited higher activity than the parent antibody and similar activity to the control antibody (FIG. 11 and Table 10).

TABLE 10

Activity of monoclones of selected PD-L1 antibody mutants

| Name | Average *EC50 [nM] |
|---|---|
| PD-L1-11A7 | 3.25 |
| PD-L1-16E12 (WT/Lambda) | |
| PD-L1-16E12 (WT/Lambda) | 0.96 |
| PD-L1-16E12-4A6 | 0.48 |
| PD-L1-16E12-4A7 | 0.37 |

TABLE 10-continued

Activity of monoclones of selected PD-L1 antibody mutants

| Name | Average *EC50 [nM] |
|---|---|
| PD-L1-16E12-4A8 | 0.83 |
| PD-L1-16E12-4A10 | 0.45 |
| PD-L1-16E12-4A11 | 0.34 |
| PD-L1-16E12-4B8 | 188.40 |
| PD-L1-16E12-4B11 | 0.63 |
| PD-L1-16E12-4B12 | 0.46 |
| PD-L1-16E12-4C9 | 0.39 |
| PD-L1-16E12-4D4 | 0.57 |
| PD-L1-16E12-4E5 | 0.45 |
| PD-L1-16E12-4E12 | 0.49 |
| PD-L1-16E12-LS-4F5 (Kappa) | 0.25 |
| PD-L1-16E12-4F11 | 1.68 |
| PD-L1-16E12-4G1 | 0.47 |
| PD-L1-16E12-4H5 | 0.33 |
| PD-L1-16E12-4H6 | 0.51 |
| PD-L1-16E12-4H8 | 0.36 |
| PD-L1-16E12-4H9 | 0.63 |
| PD-L1-16E12-4H11 | 1.02 |
| PD-L1-16E12-Kappa | 0.47 |
| PD-L1-16E12-FR-LS-4F5 (Kappa) | 13.67 |
| PD-L1-16E12-LS-4F5 (Lambda) | 0.25 |
| PD-L1-16E12-FR-LS-4F5 (Lambda) | 14.19 |
| PD-L1-16E12-FR-C-LS-4F5 (Kappa) | 5.93 |
| PD-L1-16E12-FR-C-LS-4F5 (Lambda) | 4.92 |
| PD-L1-23E5 | 1.61 |
| PD-L1-27F8 | 1.10 |
| PD-L1-31B7 | 1.74 |

In order to measure activity of 6 species of PD-L1 antibodies (4A7, 4A11, 4C9, 4F5, 4H5, 4H8) in a concentration-dependent manner, serial dilution and PD-1/PD-L1 blockade bioassay were performed again to recover the reduced signal in a concentration gradient dependent manner. The degree of recovery can be expressed as EC50 (effective concentration of mAb at 50% level of recovery signal), analyzed using Graphpad Prism6, and 4F5 exhibited the highest in vitro efficacy inhibition recovery ability of EC50 (FIG. 12).

2. Affinity of PD-L1 Antibody to Overexpressed Cells

Regarding transformation cell pools highly expressing human PD-1, HEK293E was transformed with a pcDNA3.1 plasmid containing human PD-1 (NM_005018.2) or human PD-L1 (NM_014143.2) and screened in a selective medium containing 400 ug/ml Zeocin (#R25001, Thermo Fisher). Each cell pool was identified and selected by fluorescence activated cell sorting (FACS) analysis using anti-PD-1 (#557860, BD) and used for functional assays such as FACS binding assays or FACS competition assays. 0.5 to 1×10$^6$ cells per sample were prepared from the transformation cell pools highly expressing human PD-L1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer (Table 11).

TABLE 11

Binding of selected PD-L1 antibody mutants to PD-L1 expressed on cell surface

|  | Binding at 0.9~10 ug/ml<br>Y/N<br>human PD-L1+ |
|---|---|
| Atezolizumab | Y |
| Avelumab | Y |
| PD-L1-11A7 | Y |
| PD-L1-16E12 | Y |
| PD-L1-16E12 (LS/4A11) | Y |
| PD-L1-16E12 (LS/4A7) | Y |
| PD-L1-16E12 (LS/4C9) | Y |
| PD-L1-16E12 (LS/4F5) | Y |
| PD-L1-16E12 (LS/4H5) | Y |
| PD-L1-16E12 (LS/4H8) | Y |
| PD-L1-16E12 (WT/kappa) | Y |
| PD-L1-16E12 (WT/Lambda) | Y |
| PD-L1-16E12-FR-LS-4F5 (Kappa) | Y |
| PD-L1-16E12-FR-LS-4F5 (Lambda) | Y |
| PD-L1-16E12-LS-4F5 (Kappa) | Y |
| PD-L1-16E12-LS-4F5 (Lambda) | Y |
| PD-L1-22B10 | Y |
| PD-L1-22E10 | Y |
| PD-L1-22E5 | Y |
| PD-L1-27F8 | Y |
| PD-L1-30B1 | N |
| PD-L1-31B7 | Y |
| PD-L1-31D9 | N |
| PD-L1-31E6 | Y |

0.5 to 1×10⁶ cells per sample were each prepared from the transformation cell pools highly expressing human PD-L1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer (FIG. 13).

3. Inhibitory Ability of Antibody Against Formation of PD-1/PD-L1 Complex by Enzyme Immunoadsorption Human PD-1-Fc (S1420, Y-Biologics) was added to wells of a 96-well immuno microplate (#439454, Thermo) and then washed three times with PBS containing 0.05% tween-20 (#P9416, Sigma-Aldrich), followed by washing with 4% skim milk (#232120, Becton, Dickinson and Company) and allowing to stand at room temperature for 1 hour to block non-specific binding. At the same time, human PD-L1-His (S1479, Y-Biologics) was reacted with antibodies serially diluted at a constant dilution rate at room temperature for 1 hour, followed by allowing to stand in the prepared microplate at room temperature for 1 hour. After the resulting product was subjected to the same washing method as above, the anti-biotin-His antibody (#MA1-21315-BTIN, Thermo) diluted to 1:2000 was added to the well of microplate, allowed to react at room temperature for 1 hour, and Streptavidin poly-HRP antibody (#21140, Pierce) diluted to 1:5000 was added to the well of microplate, reacted at room temperature for 1 hour and then washed in the same manner. 100 ul of a TMB substrate solution (#T0440, Sigma-Aldrich) was added to the reaction product, light was shielded, and the reaction product was allowed to stand at room temperature for 3 minutes, 50 µL of 2.5 M sulfuric acid (#S1478, Samchun) was added to stop the reaction, and absorbance was measured at 450 nm using a spectrophotometer (#GM3000, Glomax® Discover System Promega). The results are shown in FIG. 14.

4. Affinity of PD-L1 Antibody Using ProteOn XPR36

A ProteOn XPR36 (BioRad) instrument was used. The GLC sensor chip (BioRad) was mounted on the instrument and washed with PBST buffer, and the carboxymethyldextran surface was activated with an EDC/sulfo-NHS mixed solution. PD-L1-hFc dissolved at a concentration of 5 ug/ml in a 10 mM sodium acetate buffer solution (pH 5.0) was injected and immobilized on the GLC sensor chip.

In order to deactivate the activated carboxyl groups that remain unreacted with the PD-L1 protein, 1 M ethanolamine was flowed and 10 mM glycine (pH 2.0) was injected in order to wash proteins that remain unbound to the sensor chip. Then, sensogram data were collected during binding and dissociation over time while allowing the antibodies to flow at a flow rate of 30 µL/min (30 nM to 0.123 nM) for 10 min using PBST buffer.

The equilibrium dissociation constant ($K_D$) was calculated by plotting and fitting the sensogram data in the equilibrium state depending on concentration. As a result, 16E12(4F5) exhibited $K_D$ of 0.001 nM, indicating high affinity to the PD-L1 antigen (FIG. 15).

Comparison in affinity of PDL1-16E12, LS and 4F5 to human, monkey and mouse PD-L1 proteins is as shown in Table 12.

TABLE 12

Binding capacity of monoclonal antibody of selected PD1 monoclonal antibody (16E12-4F5) to human, monkey and mouse

| PD-L1 Origin | KD (M) | Ka (1/Ms) | Kd (1/s) |
|---|---|---|---|
| human | $1.0 \times 10^{-12}$ | $3.100 \times 10^5$ | $1.0 \times 10^{-7}$ |
| mouse | $8.082 \times 10^{-10}$ | $8.327 \times 10^5$ | $6.730 \times 10^{-4}$ |
| cynomolgus | $1.0 \times 10^{-12}$ | $2.869 \times 10^5$ | $1.0 \times 10^{-7}$ |

Example 9: Determination of Epitope of PD-L1 Monoclonal Antibody

An antigen PD-L1 wild type (WT) or several mutants were coated at a density of 100 ng/well on a 96-well immunoplate at 4° C. for 16 hours and the wells were blocked with 4% skim milk dissolved in PBS. Each well was washed with 0.2 ml of PBS/T, and then a single clone scFv-phage (each 100 scFv-phage) cultured for 16 hours was added in a dose of 100 µl to each well and reacted at room temperature for 2 hours. Again, each well was washed 4 times with 0.2 ml of PBS/T, and then the second antibody, anti-Fab, was diluted to 1/2000 and reacted at room temperature for 1 hour. After washing with 0.2 ml of PBS/T, color development was performed and absorbance was measured at 490 nm.

Figure 16:
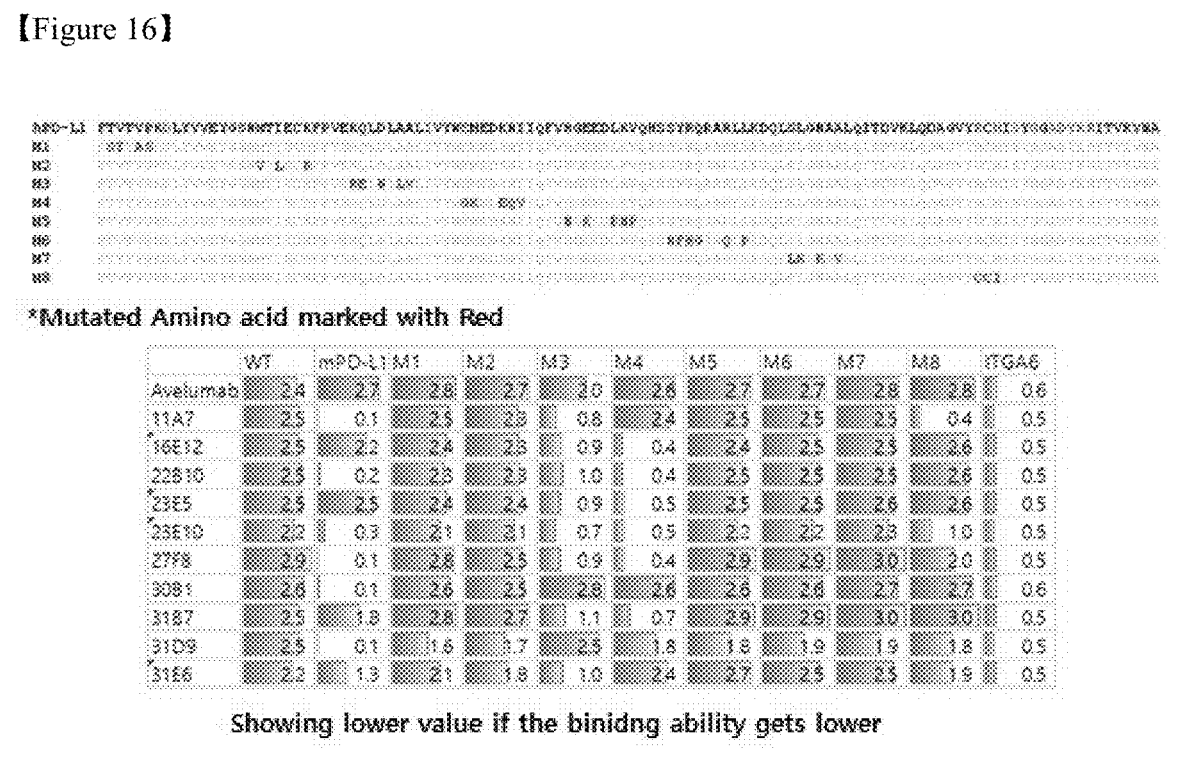

As a result, it was confirmed that the control antibody and PD-L1 mutants had different binding behaviors and thus different epitopes (FIG. 16).

Example 10: Activity Increase of PD-L1 Monoclonal Antibody in Allogenic MLR Reaction T cells were mixed with monocyte-derived dendritic cells separated from different humans at a ratio of 1:10 and cultured for 5 days, and the amount of interferon gamma in the culture medium was measured. As a result, culture media containing the parent antibody of 16E12 exhibited a concentration-dependent increase in amount of interferon gamma (FIG. 17).

Example 11: Evaluation of Efficacy of PD-L1 Monoclonal Antibody in Syngeneic Cancer Animal Model In order to identify the in vivo efficacy of 16E12-2B9 PD-L1 monoclonal antibody, $8 \times 10^6$ CT-26 cells as colon cancer cells were subcutaneously injected into the flank of BALb/C mice, and tumor growth was observed, while administering the monoclonal antibody at a dose of 5 mg/kg twice a week over 3 weeks, from the time when the size of tumor was similar to that of a millet. As a result, a significant decrease in tumor size was observed in the PD-L1 monoclonal antibody-administered group (FIG. 18).

Example 11: Thermal Stability Test of PD-L1 Monoclonal Antibody

The antibody protein was diluted in DPBS to 3 uM, 45 ul, mixed with 5 ul of 200×Sypro orange dye (#S6650, Thermo) and then aliquoted in a dose of 50 ul into a qPCR Tube (#B77009, B57651, bioplastics). QPCR was performed using a Biorad CFX96 real time PCR system. The qPCR conditions were given as follows: reaction at 25° C. for 30 seconds, elevation of the temperature by 1° C. up to 99° C. and at the same time, reaction at each temperature for 1 min, and final reaction at 25° C. for 10 seconds. Tm (melting temperature) was used as a rate constant at which the antibody structure was un-bound. The results are shown in Table 13 below.

TABLE 13

Thermodynamic stability of antibody

| Sample | Tm |
| --- | --- |
| Avelumab | 61 |
| Atezolizumab | 67 |
| 16E12 (WT/kappa) | 67 |
| 16E12-LS-4F5 (K) | 67 |
| 16E12-LS-4F5 (L) | 67 |

Example 13: Determination of Binding to PD-L2

In order to identify binding of the anti-PD-L1 antibody to PD-L2, human PD-L2-Fc (#10292-H02H, Sino) was immobilized on wells of a 96-well immuno microplate (#439454, Thermo) at 4° C. for 16 hours, and then washed three times with PBS containing 0.05% tween-20 (#P9416, Sigma-Aldrich), followed by allowing to stand in a cleaning solution containing 4% skim milk (#232120, Becton, Dickinson and Company) at room temperature for 1 hour to block non-specific binding. At the same time, each antibody serially diluted at a constant dilution rate or human PD-1-His (S1352, Y-Biologics) used as a positive control was reacted with at room temperature for 1 hour, followed by allowing to stand in the prepared microplate at room temperature for 1 hour. After the resulting product was subjected to the same washing method as above, the anti-biotin-His antibody (#MA1-21315-BTIN, Thermo) diluted to 1:2000 was added to the well of microplate, allowed to react at room temperature for 1 hour, and the streptavidin poly-HRP antibody (#21140, Pierce) diluted to 1:5000 was added to the well of microplate, reacted at room temperature for 1 hour and then washed in the same manner. 100 ul of a TMB substrate solution (#T0440, Sigma-Aldrich) was added to the reaction product, light was shielded, and the reaction product was allowed to stand at room temperature for 3 minutes, 50 µL of 2.5 M sulfuric acid (#S1478, Samchun) was added to stop the reaction, and absorbance was measured at 450 nm using a spectrophotometer (#GM3000, Glomax® Discover System Promega). The results are shown in FIG. 19.

INDUSTRIAL AVAILABILITY

The novel antibodies binding to PD-L1 or antigen-binding fragments thereof according to the present disclosure can bind to PD-1 with high affinity, and inhibit the formation of the PD-1/PD-L1 complex, thereby inhibiting T cell depletion that evades PD-1/PD-L1-mediated T cell activity. Accordingly, the antibodies binding to PD-L1 or antigen-binding fragments thereof according to the present disclosure are useful for the prevention or treatment of target cancer or infectious diseases.

Although specific configurations of the present disclosure have been described in detail, those skilled in the art will appreciate that this description is provided as preferred embodiments for illustrative purposes and should not be construed as limiting the scope of the present disclosure. Therefore, the substantial scope of the present disclosure is defined by the accompanying claims and equivalents thereto.

The invention claimed is:

1. An antibody binding to PD-L1 or an antigen-binding fragment thereof, comprising:

a heavy chain variable region comprising the heavy chain CDR1 of SEQ ID NO: 1, the heavy chain CDR2 of SEQ ID NO: 8 and the heavy chain CDR3 of SEQ ID NO: 16, a light chain variable region comprising the light chain CDR1 of SEQ ID NO: 88, the light chain CDR2 of SEQ ID NO: 103 and the light chain CDR3 of SEQ ID NO: 120;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 104 and the light chain CDR3 of SEQ ID NO: 121;

a heavy chain variable region comprising the heavy chain CDR1 of SEQ ID NO: 2, the heavy chain CDR2 of SEQ ID NO: 9 and the heavy chain CDR3 of SEQ ID NO: 18, a light chain variable region comprising the light chain CDR1 of SEQ ID NO: 90, the light chain CDR2 of SEQ ID NO: 105 and the light chain CDR3 of SEQ ID NO: 122;

a heavy chain variable region comprising the heavy chain CDR1 of SEQ ID NO: 3, the heavy chain CDR2 of SEQ ID NO: 10 and the heavy chain CDR3 of SEQ ID NO: 19, a light chain variable region comprising the light chain CDR1 of SEQ ID NO: 91, the light chain CDR2 of SEQ ID NO: 106 and the light chain CDR3 of SEQ ID NO: 123;

a heavy chain variable region comprising the heavy chain CDR1 of SEQ ID NO: 4, the heavy chain CDR2 of SEQ ID NO: 11 and the heavy chain CDR3 of SEQ ID NO: 20, a light chain variable region comprising the light chain CDR1 of SEQ ID NO: 89, the light chain CDR2 of SEQ ID NO: 107 and the light chain CDR3 of SEQ ID NO: 124;

a heavy chain variable region comprising the heavy chain CDR1 of SEQ ID NO: 5, the heavy chain CDR2 of SEQ ID NO: 12 and the heavy chain CDR3 of SEQ ID NO: 21, a light chain variable region comprising the light chain CDR1 of SEQ ID NO: 92, the light chain CDR2 of SEQ ID NO: 108 and the light chain CDR3 of SEQ ID NO: 122;

a heavy chain variable region comprising the heavy chain CDR1 of SEQ ID NO: 6, the heavy chain CDR2 of SEQ ID NO: 13 and the heavy chain CDR3 of SEQ ID NO: 22, a light chain variable region comprising the light chain CDR1 of SEQ ID NO: 93, the light chain CDR2 of SEQ ID NO: 109 and the light chain CDR3 of SEQ ID NO: 125;

a heavy chain variable region comprising the heavy chain CDR1 of SEQ ID NO: 2, the heavy chain CDR2 of SEQ ID NO: 9 and the heavy chain CDR3 of SEQ ID NO: 23, a light chain variable region comprising the light chain CDR1 of SEQ ID NO: 94, the light chain CDR2 of SEQ ID NO: 110 and the light chain CDR3 of SEQ ID NO: 126;

a heavy chain variable region comprising the heavy chain CDR1 of SEQ ID NO: 7, the heavy chain CDR2 of SEQ ID NO: 14 and the heavy chain CDR3 of SEQ ID NO: 24, a light chain variable region comprising the light chain CDR1 of SEQ ID NO: 95, the light chain CDR2 of SEQ ID NO: 111 and the light chain CDR3 of SEQ ID NO: 127;

a heavy chain variable region comprising the heavy chain CDR1 of SEQ ID NO: 2, the heavy chain CDR2 of SEQ ID NO: 15 and the heavy chain CDR3 of SEQ ID NO: 25, a light chain variable region comprising the light chain CDR1 of SEQ ID NO: 96, the light chain CDR2 of SEQ ID NO: 112 and the light chain CDR3 of SEQ ID NO: 128;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 108 and the light chain CDR3 of SEQ ID NO: 129;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 105 and the light chain CDR3 of SEQ ID NO: 130;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 113 and the light chain CDR3 of SEQ ID NO: 131;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 97, the light chain CDR2 of SEQ ID NO: 104 and the light chain CDR3 of SEQ ID NO: 132;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 104 and the light chain CDR3 of SEQ ID NO: 133;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 97, the light chain CDR2 of SEQ ID NO: 114 and the light chain CDR3 of SEQ ID NO: 134;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 92, the light chain CDR2 of SEQ ID NO: 115 and the light chain CDR3 of SEQ ID NO: 135;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 98, the light chain CDR2 of SEQ ID NO: 104 and the light chain CDR3 of SEQ ID NO: 130;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 116 and the light chain CDR3 of SEQ ID NO: 121;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 108 and the light chain CDR3 of SEQ ID NO: 136;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 99, the light chain CDR2 of SEQ ID NO: 105 and the light chain CDR3 of SEQ ID NO: 137;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 117 and the light chain CDR3 of SEQ ID NO: 138;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 118 and the light chain CDR3 of SEQ ID NO: 133;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 119 and the light chain CDR3 of SEQ ID NO: 139;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 100, the light chain CDR2 of SEQ ID NO: 104 and the light chain CDR3 of SEQ ID NO: 140;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 108 and the light chain CDR3 of SEQ ID NO: 141;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 105 and the light chain CDR3 of SEQ ID NO: 139;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 104 and the light chain CDR3 of SEQ ID NO: 142;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 89, the light chain CDR2 of SEQ ID NO: 105 and the light chain CDR3 of SEQ ID NO: 143;

a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 101, the light chain CDR2 of SEQ ID NO: 104 and the light chain CDR3 of SEQ ID NO: 141; or a heavy chain variable region comprising the heavy chain CDR1 of SEQ ID NO: 2, the heavy chain CDR2 of SEQ ID NO: 9 and the heavy chain CDR3 of SEQ ID NO: 17, a light chain variable region comprising the light chain CDR1 of SEQ ID NO: 102, the light chain CDR2 of SEQ ID NO: 104 and the light chain CDR3 of SEQ ID NO: 144.

2. The antibody or an antigen-binding fragment thereof according to claim 1, comprising:
   a heavy chain variable region FR1 selected from the group consisting of SEQ ID NOS: 26 to 34;
   a heavy chain variable region FR2 selected from the group consisting of SEQ ID NOS: 35 to 41;
   a heavy chain variable region FR3 selected from the group consisting of SEQ ID NOS: 42 to 49; or
   a heavy chain variable region FR4 selected from the group consisting of SEQ ID NOS: 50 to 54.

3. The antibody or an antigen-binding fragment thereof according to claim 1, comprising:
   a light chain variable region FR1 selected from the group consisting of SEQ ID NOS: 145 to 163;
   a light chain variable region FR2 selected from the group consisting of SEQ ID NOS: 164 to 184;
   a light chain variable region FR3 selected from the group consisting of SEQ ID NOS: 185 to 210; or
   a light chain variable region FR4 selected from the group consisting of SEQ ID NOS: 211 to 216.

4. The antibody or an antigen-binding fragment thereof according to claim 1, comprising:
   a heavy chain variable region comprising a sequence selected from the group consisting of sequences as set forth in SEQ ID NOS: 57 to 87.

5. The antibody or an antigen-binding fragment thereof according to claim 1, comprising:
   a light chain variable region comprising a sequence selected from the group consisting of sequences as set forth in SEQ ID NOS: 217 to 247.

6. A nucleic acid encoding the antibody or an antigen-binding fragment thereof according to claim 1.

7. An expression vector comprising the nucleic acid according to claim 6.

8. A cell transformed with the expression vector according to claim 7.

9. A method for producing an antibody binding to PD-L1 or an antigen-binding fragment thereof, comprising:
   (a) culturing the cell according to claim 8; and
   (b) recovering the antibody or antigen-binding fragment thereof from the cultured cell.

10. A composition for preventing or treating cancer or infectious diseases which expresses PD-L1 comprising, as an active ingredient, the antibody or an antigen-binding fragment thereof according to claim 1.

* * * * *